US010960037B2

(12) United States Patent
Addington et al.

(10) Patent No.: US 10,960,037 B2
(45) Date of Patent: *Mar. 30, 2021

(54) METHOD OF TREATING NEUROLOGICAL CONDITIONS WITH EXTRACT OF *NERIUM* SPECIES OR *THEVETIA* SPECIES

(71) Applicant: PHOENIX BIOTECHNOLOGY, INC., San Antonio, TX (US)

(72) Inventors: Otis C. Addington, San Antonio, TX (US); Robert A. Newman, Surry, ME (US)

(73) Assignee: PHOENIX BIOTECHNOLOGY, INC., San Antonio, TX (US)

(*) Notice: Subject to any disclaimer, the term of this patent is extended or adjusted under 35 U.S.C. 154(b) by 104 days.

This patent is subject to a terminal disclaimer.

(21) Appl. No.: 16/387,263

(22) Filed: Apr. 17, 2019

(65) Prior Publication Data
US 2019/0240277 A1 Aug. 8, 2019

Related U.S. Application Data

(60) Division of application No. 15/704,212, filed on Sep. 14, 2017, which is a continuation-in-part of application No. 15/617,257, filed on Jun. 8, 2017, now Pat. No. 10,226,497, which is a continuation of application No. 14/658,652, filed on Mar. 16, 2015, now abandoned, which is a division of application No. 13/288,559, filed on Nov. 3, 2011, now Pat. No. 9,011,937, which is a continuation-in-part of application No. 12/987,693, filed on Jan. 10, 2011, now Pat. No. 8,481,086, and a continuation-in-part of application No. PCT/US2011/020672, filed on Jan. 10, 2011, said application No. 15/704,212 is a continuation-in-part of application No. 15/143,973, filed on May 2, 2016, now Pat. No. 9,877,979, which is a continuation of application No. 13/909,613, filed on Jun. 4, 2013, now Pat. No. 9,358,293, and a continuation of application No. 13/909,562, filed on Jun. 4, 2013, now Pat. No. 9,220,778, which is a continuation of application No. 12/987,693.

(60) Provisional application No. 61/415,945, filed on Nov. 22, 2010, provisional application No. 61/293,812, filed on Jan. 11, 2010.

(51) Int. Cl.
A61K 36/00 (2006.01)
A61K 36/24 (2006.01)
A61K 31/704 (2006.01)
A61K 45/06 (2006.01)
A61K 31/7048 (2006.01)
A61K 31/19 (2006.01)
A61K 31/56 (2006.01)

(52) U.S. Cl.
CPC .............. *A61K 36/24* (2013.01); *A61K 31/19* (2013.01); *A61K 31/56* (2013.01); *A61K 31/704* (2013.01); *A61K 31/7048* (2013.01); *A61K 45/06* (2013.01)

(58) Field of Classification Search
None
See application file for complete search history.

(56) References Cited

U.S. PATENT DOCUMENTS

| | | |
|---|---|---|
| 5,977,174 A | 11/1999 | Bradley |
| 6,217,874 B1 | 4/2001 | Johannsen |
| 7,402,325 B2 | 7/2008 | Addington |
| 8,187,644 B2 | 5/2012 | Addington |
| 8,394,434 B2 | 3/2013 | Addington |
| 8,481,086 B2 | 7/2013 | Addington |
| 9,011,937 B2 | 4/2015 | Addington |
| 9,220,778 B2 | 12/2015 | Addington |
| 9,358,293 B2 | 6/2016 | Addington |
| 2006/0135443 A1 | 6/2006 | Khodadoust |
| 2006/0234955 A1 | 10/2006 | Pollard |
| 2007/0154573 A1 | 7/2007 | Rashan |
| 2007/0249711 A1 | 10/2007 | Choi |
| 2008/0200401 A1 | 8/2008 | Addington |
| 2009/0074660 A1* | 3/2009 | Korman ................. C07K 16/30 424/1.49 |
| 2013/0267475 A1 | 10/2013 | Addington |
| 2015/0283191 A1 | 10/2015 | Addington |
| 2016/0243143 A1 | 8/2016 | Addington |
| 2017/0274031 A1 | 9/2017 | Addington |

FOREIGN PATENT DOCUMENTS

| | | | |
|---|---|---|---|
| CN | 1686425 A | * | 10/2005 |
| CN | 1301774 A1 | | 2/2016 |
| EP | 2260851 A1 | | 12/2010 |
| WO | 9932097 A2 | | 7/1999 |

(Continued)

OTHER PUBLICATIONS

Chen et al, Inhibition of *Escherichia coli* heat-labile enterotoxin-induced diarrhea by Chaenomeles speciosa. Journal of Ethnopharmacology, (Sep. 5, 2007) vol. 113, No. 2, pp. 233-239 (Year: 2007).*
Bai et al. ("Studies on Chemical Constituents of Japanese Nerium indicum Mill and Their Cytotoxicity in vitro" in J. Anhui Agri. Sci. (2009), 37(20), 9480-9488).
Wang et al. ("LC/MS/MS Analyses of an Oleander Extract for Cancer Treatment" in Anal. Chem. (2000), 72, 3547-3552).
Wang et al. ("Cardiac glycosides provide neuroprotection against ischemic stroke: discovery by a brain slice-based compound screening platform"). Proc. Natl. Acad. Sci. (Jul. 5, 2006), 103:27, pp. 10461-10466.

(Continued)

Primary Examiner — Qiuwen Mi
(74) Attorney, Agent, or Firm — Innovar, L.L.C.; Rick Matos

(57) ABSTRACT

A method of treating neurological condition in a subject by administration of a neuroprotective composition of a mixture of two or more triterpenes. Alzheimer's disease, Huntington's disease, stroke or Parkinson's disease are treated by administering a therapeutically effective amount of the neuroprotective composition to a subject.

23 Claims, 32 Drawing Sheets

(56) References Cited

FOREIGN PATENT DOCUMENTS

| WO | 0064921 A2 | 11/2000 |
|---|---|---|
| WO | 03099011 A1 | 12/2003 |
| WO | 2009/064657 A1 | 5/2009 |

OTHER PUBLICATIONS

Yu et al. ("New Polysaccharide from Nerium indicum protects neurons via stress kinase signaling pathway") Brain Research, (2007), 1153, pp. 221-230.
Rodan et al. ("Stroke recurrence in children with congenital heart disease", Annals of Neurology (Jul. 2012), 72(1), 103-111).
Riikonen et al. ("Hereditary and acquired risk factors for childhood stroke", Neuropediatrics (Oct. 1994), 25(5), 227-233).
Dominiczak et al. ("Genetics of common polygenic stroke". Nature Genetics (Oct. 2003), 35(2), 116-117).
Grubb et al. ("Risks of stroke and current indications for cerebral revascularization in patients with carotid occlusion", Neurosurgery Clinics of North America (Jul. 2001), 12(3), 473-487).
Jensen et al. ("The promise and potential pitfalls of serum biomarkers for ischemic stroke and transient ischemic attack", The Neurologist (Jul. 2008), 14(4), 243-6).
Lasek-Bal et al. ("Cardiogenic stroke in the young", Postepy w Kardiologii Inerwencyjnej (2012), 8(2), 131-137).
Rizos et al. ("Evolution of stroke diagnosis in the emergency room—a prospective observational study", Cerebrovascular diseases (Basel, Switzerland), (2009), 28(5), 448-453).
Siddiqui et al. ("Oleanderol, a new pentacyclic triterpene from the leaves of Nerium oleander", J. Natur. Prod. (1988), 51(2), 229-233).
Jaeger et al. ("Pentacyclic triterpene distribution in various plants—rich sources for a new group of multi-potent plant extracts", Molecules (2009), 14(6), 2016-2031).
Karawya et al. ("Phytochemical study of Nerium oleander growing in Egypt. Preliminary investigation", United Arab Republic J. Pharm. Sci. (1970), 11(2), 193-209.
Lo et al. ("Dual activities of the anti-cancer drug candidate PBI-05204 provide neuroprotection in brain slice models for neurodegenerative diseases and stroke", Scientific Reports (2016), 6, 25626; doi:10.1038/srep25626).
Rong et al. ("Protective effects of oleanolic acid on cerebral ischemic damage in vivo and H(2)O(2)-induced injury in vitro"; Pharm. Bio. (2011), 49(1), 78-85) (abstract).
So et al. ("Anti-ischemic activities of aralia cordata and its active component, oleanolic acid"; Arch. Pharm. Res. (2009), 32(6), 923-932) (abstract).
Li et al. ("Ursolic acid promotes the neuroprotection by activating Nrf2 pathway after cerebral ischemia in mice"; Brain Res. (2013), 1497, 32-39) (abstract).
Garcia-Morales et al. ("Anti-inflammatory, antioxidant and anti-acetylcholinesterase activities of Bouvardia ternifolia: potential implications in Alzheimer's disease"; Arch. Pharm. Res. (2015), 38(7), 1369-1379).
Zhang et al. ("Ursolic acid reduces oxidative stress to alleviate early brain injury following experimental subarachnoid hemorrhage"; Neuroscience Letters (2014), 579, 12-17) (abstract).
Qian et al. ("Maslinic acid, a natural triterpenoid compound from Olea europaea, protects cortical neurons against oxygen-glucose deprivation-induced injury"; Eur. J. Pharmacol. (2011), 670(1), 148-153).
Yoo et al. ("Terpenoids as potential anti-Alzheimer's disease therapeutics"; Molecules (2012), 17(3), 3524-3538) (abstract).
Heo et al. ("Ursolic acid of *Origanum majorana* L. reduces Abeta-induced oxidative injury"; Mol. Cells (2002), 13(1), 5-11).
Chung et al. ("Inhibitory effect of ursolic acid purified from *Origanum majoma* L on the acetylcholinesterase"; Mol. Cells (2001), 11(2), 137-143).
Siddiqui et al. ("Cardenolides and triterpenoids of the leaves of Thevetia neriifolia"; Phytochem. (1992), 3(10), 3541-3546).

* cited by examiner

Oleandrin striatal

Oleandrin cortical

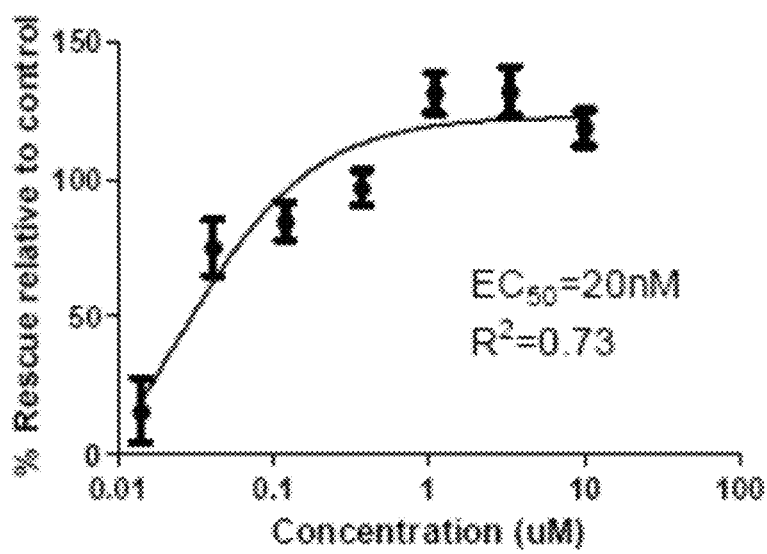
FIG. 3C Oleandrin pncsb0075 striatal
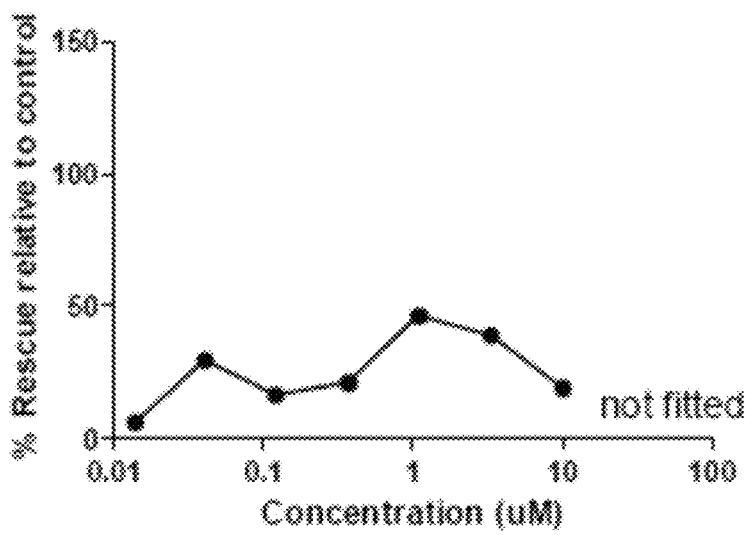
FIG. 3D Oleandrin pncsb0075 cortical

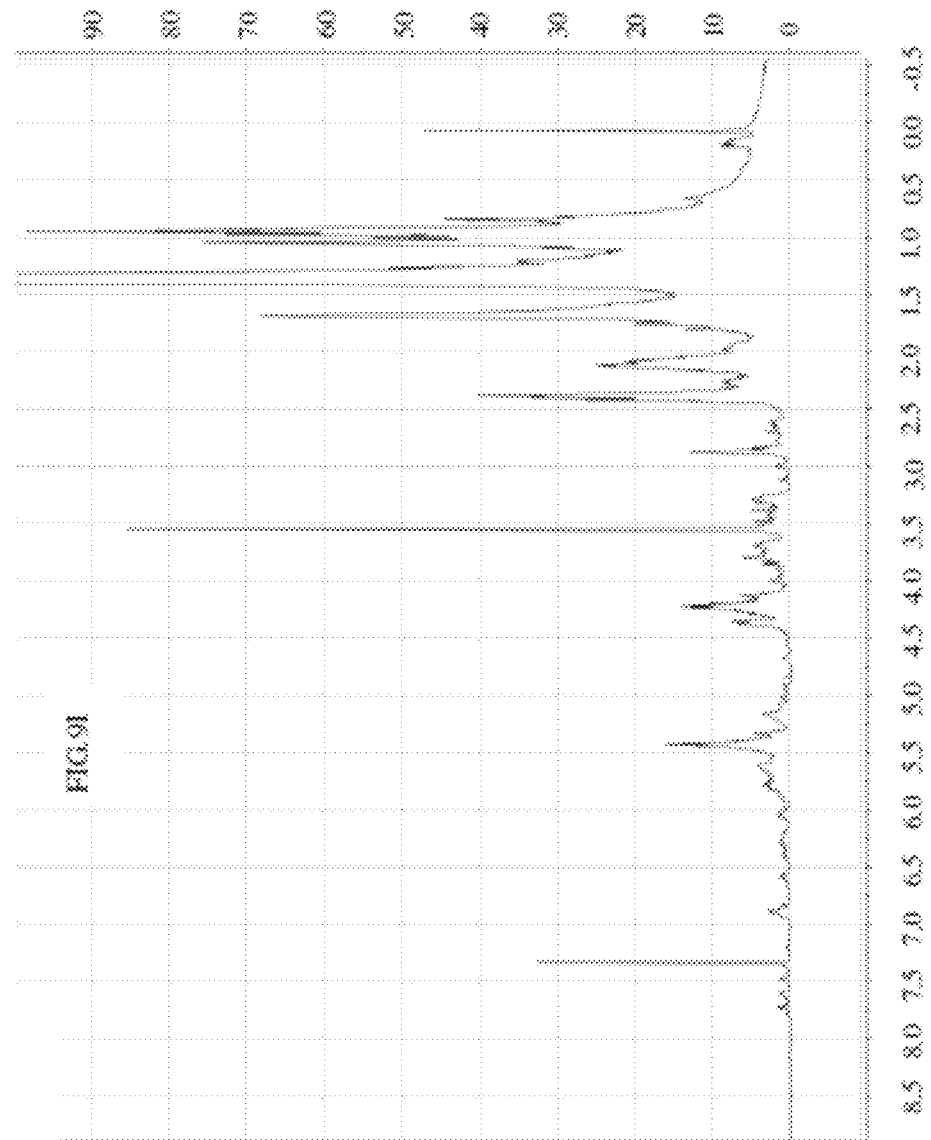

7 h treatment 24 h treatment

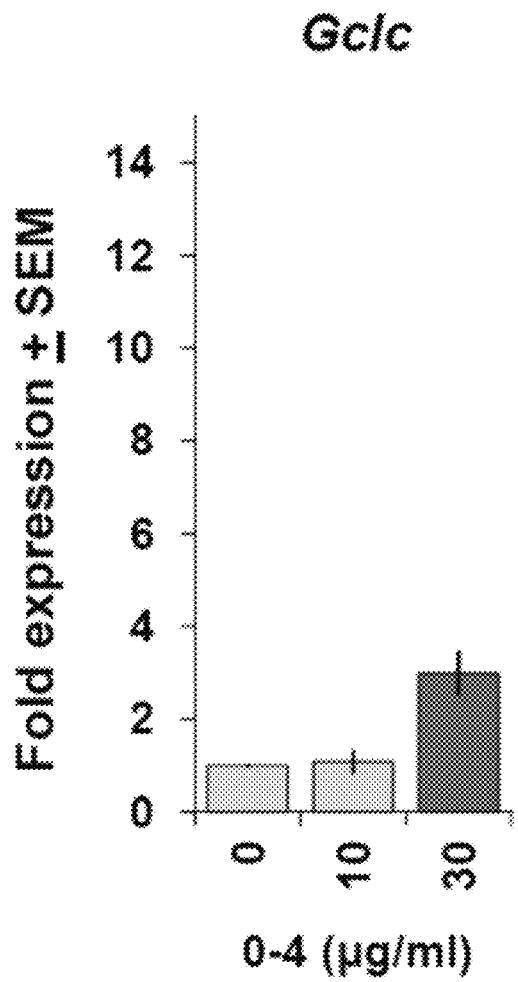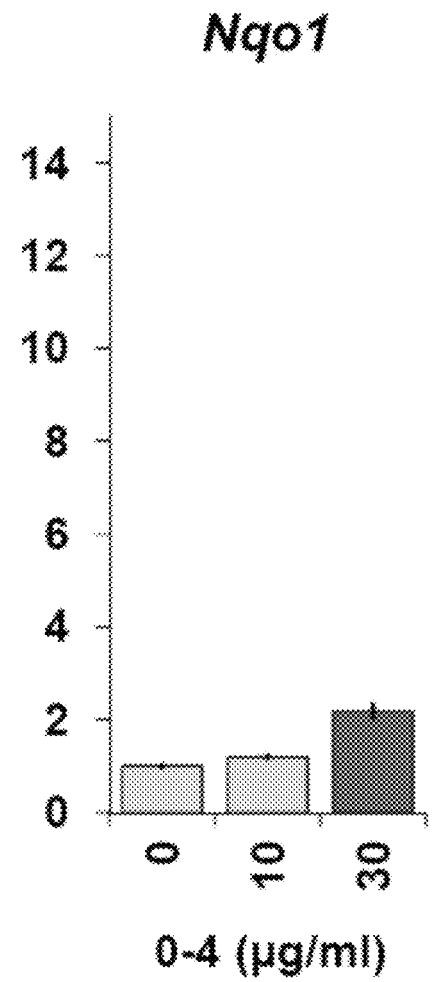
FIG. 15A  *Gclc*
FIG. 15B  *Nqo1*

*Srx*

0-4 (µg/ml)

*Hmox1*

0-4 (µg/ml)

METHOD OF TREATING NEUROLOGICAL CONDITIONS WITH EXTRACT OF *NERIUM* SPECIES OR *THEVETIA* SPECIES

CROSS-REFERENCE TO EARLIER FILED APPLICATIONS

The present invention application claims the benefit of and is a division of application Ser. No. 15/704,212 filed Sep. 14, 2017, which is a continuation-in-part of application Ser. No. 15/617,257 filed Jun. 8, 2017, now U.S. Ser. No. 10/226,497 issued Mar. 12, 2019, which is a continuation of application Ser. No. 14/658,652, filed Mar. 16, 2015, which is a division of application Ser. No. 13/288,559, filed Nov. 3, 2011, now U.S. Pat. No. 9,011,937 issued Apr. 21, 2015, which claims the benefit of provisional application 61/415,945, filed Nov. 22, 2010, and said application Ser. No. 13/288,559 is a continuation-in-part of application Ser. No. 12/987,693 filed Jan. 10, 2011, now U.S. Pat. No. 8,481,086 issued Jul. 9, 2013, which claim the benefit of provisional application No. 61/293,812, filed Jan. 11, 2010, and said application Ser. No. 13/288,559 is also a continuation-in-part of PCT International application No. PCT/US11/20672 filed Jan. 10, 2011, which also claim the benefit of said provisional application No. 61/293,812, and said application Ser. No. 15/704,212 is a continuation-in-part of application Ser. No. 15/143,973 filed May 2, 2016, now U.S. Pat. No. 9,877,979 issued Jan. 30, 2018, which is a continuation of application Ser. No. 13/909,613, filed Jun. 4, 2013, now U.S. Pat. No. 9,358,293 issued Jun. 7, 2016, and said application Ser. No. 15/143,973 is also a continuation of application Ser. No. 13/909,562, filed Jun. 4, 2013, now U.S. Pat. No. 9,220,778 issued Dec. 29, 2015, which is a continuation of said application Ser. No. 12/987,693, the entire disclosures of which are hereby incorporated by reference.

FIELD OF THE INVENTION

The present invention concerns a method of treating neurological conditions with a neuroprotective composition comprising two or more triterpenes. For example, the neuroprotective composition is an extract, or fraction thereof, of *Nerium* species or *Thevetia* species, or preparations (compositions, formulations) containing them. In particular, the invention concerns a method for treating neurological disease or disorder by administration of the neuroprotective composition to a subject in need thereof. The invention also includes pharmaceutical neuroprotective compositions containing fractions or sub-fractions of the extract as well as their methods of use and preparation. The invention also includes neuroprotective compositions consisting essentially of at least two or at least three triterpenes as the primary or sole neuroprotective agents.

BACKGROUND OF THE INVENTION

Neurological diseases and disorders affect brain function. Many efforts have been made to develop curative or ameliorative therapies for these diseases and disorders; however, no comprehensive or universally curative therapy has been developed, even though there are numerous pharmacotherapeutic approaches that have been proven to be effective against various diseases and disorders.

Huntington's disease (HD) is an inherited disease of the brain that affects the nervous system. It is caused by a defective gene that is passed from parent to child. The HD gene interferes with the manufacture of a particular protein known as 'Huntington' which appears to be crucial for proper brain development. The classic signs of HD include emotional, cognitive and motor disturbances. Huntington's is characterized by jerky involuntary movements (chorea), but sometimes causes rigidity without abnormal movements, changes in using the limbs (apraxia), loss of control of bodily functions and dementia, including a progressive deterioration of memory, speed of thought, judgment, and lack of awareness of problems and planning. There is no known cure for Huntington's disease. Although there are a number of medications to help control symptoms associated with HD such as emotional and movement problems, there is no treatment to stop or reverse the course of the disease. Huntington's disease has been recognized as a disease with a general membrane abnormality. A significantly elevated level and activity (10 fold increase) of Na,K-ATPase has been observed in membranes of erythrocytes and basal ganglia of Huntington's patients compared to that of normal (Butterfield D A, Oeswein J Q, Prunty M E, Hisle K C, Markesbery W R). Increased sodium, potassium adenosine triphosphatase activity in erythrocyte membranes in Huntington's disease. Ann Neurology, 4:60-62, 1978) fibroblast membranes obtained from the skin of Huntington's disease patients (Schroeder F, Goetz I E, Roberts E, Membrane anomalies in Huntington's disease fibroblasts. J. Neurochem. 43: 526-539, 1984).

Alzheimer's disease is a form of dementia—a neurodegenerative disease that damages the brain's intellectual functions (memory, orientation, calculation, etc.), but usually preserves its motor functions. In Alzheimer's disease, the mind gradually deteriorates, causing memory loss, confusion, disorientation, impaired judgment and other problems that may affect a person's ability to perform normal daily activities. The type, severity, sequence and progression of mental changes vary greatly. There is no known cure for Alzheimer's disease and no known way to slow its progression. For some people in the early or middle stages of the disease, medication such as tacrine may alleviate some cognitive symptoms. Aricept (donepezil) and Exelon (rivastigmine) are reversible acetylcholinesterase inhibitors that are indicated for the treatment of mild to moderate dementia of the Alzheimer's type. These drugs (called cholinesterase inhibitors) work by increasing the brain's levels of the neurotransmitter acetylcholine, helping to restore communication between brain cells. Some medications may help control behavioral symptoms such as sleeplessness, agitation, wandering, anxiety, and depression. These treatments are aimed at making the patient more comfortable. Although no medication is known to cure Alzheimer's disease, cholinesterase inhibitors may improve performance of daily activities, or lessen behavioral problems. Medications for the treatment of Alzheimer's disease currently being tested include estrogens, nonsteroidal anti-inflammatory agents, vitamin E, selegiline (Carbex, Eldepryl) and the botanical product gingko *biloba*.

*Nerium oleander* is an ornamental plant widely distributed in subtropical Asia, the southwestern United States, and the Mediterranean. Its medical and toxicological properties have long been recognized. It has been used, for example, in the treatment of hemorrhoids, ulcers, leprosy, snake bites, and even in the induction of abortion. Oleandrin, an important component but not the sole component of *oleander* extract, is a cardiac glycoside.

Extraction of glycosides from plants of *Nerium* species has provided pharmacologically/therapeutically active ingredients from *Nerium oleander*. Among these are oleandrin, neriifolin (nerifolin), and other cardiac glycoside compounds. Oleandrin extracts obtained by hot-water extraction of *Nerium oleander*, sold under the trademark ANVIRZEL™, contain the concentrated form or powdered form of a hot-water extract of *Nerium oleander*. A Phase I trial of a hot water *oleander* extract (i.e. Anvirzel™) has been completed (Mekhail et al., *Am. Soc. Clin. Oncol.*, vol. 20, p. 82b, 2001). It was concluded that *oleander* extracts, which would provide about 57 ug oleandrin/day, can be safely administered at doses up to 1.2 ml/m²/d. No dose limiting toxicities were found.

Rong et al. (Pharm. Biol. (January 2011), 49(1), 78-85) suggest oleanolic acid might be suitable for attenuating ischemic stroke. So et al. (Arch. Pharm. Res. (June 2009), 32(6), 923-932) suggest oleanolic acid might be suitable for the prevention and treatment of neurodegeneration in stroke. Li et al. (Brain Res. (February 2013), 1497, 32-39) suggest ursolic acid might provide neuroprotection after cerebral ischemia in mice. Garcia-Morales et al. (Arch. Pharm. Res. (July 2015), 38(7), 1369-1379) suggest that an extract of *Bouvardia ternifolia* should be further studied for treating Alzheimer's disease. Zhang et al. (Neuroscience Letters (2014), 579, 12-17) report that ursolic acid reduces oxidative stress following experimental subarachnoid hemorrhage. Qian et al. (Eur. J. Pharmacol. (2011), 670(1), 148-153) report that maslinic acid protects cortical neurons against oxygen-glucose deprivation-induced injury in rats. EP 2260851 A1 to Consejo Superior de Investigaciones Cientificas (Madrid, ES) suggests the use of oleanolic acid for the treatment of multiple sclerosis. Yoo et al. (Molecules, (May 2012), 17(3), 3524-38) suggest the use of terpenoids as anti-Alzheimer's disease therapeutics. Heo et al. (Mol. Cells (February 2002), 13(1), 5-11) suggest ursolic acid reduces amyloid beta protein-induced oxidative cell death. Chung et al. (Mol. Cells (April 2001), 11(2), 137-143) suggest ursolic acid appears to be a potent inhibitor of acetylcholinesterase in Alzheimer's disease. US 2007/0249711 A1 (Pub. Date. Oct. 25, 2007) to Choi et al. suggests the use of oleanolic acid and ursolic acid for improving brain functions to prevent and treat mild cognitive impairment and dementia.

Oleanolic acid is in a class of triterpenoids typified by compounds such as bardoxolone which have been shown to be potent activators of the innate cellular phase 2 detoxifying pathway, in which activation of the transcription factor Nrf2 leads to transcriptional increases in programs of downstream antioxidant genes containing the antioxidant transcriptional response element (ARE). Bardoxolone itself has been extensively investigated in clinical trials in inflammatory conditions; however, a Phase 3 clinical trial in chronic kidney disease was terminated due to adverse events that may have been related to known cellular toxicities of certain triterpenoids including bardoxolone at elevated concentrations.

Compositions containing triterpenes in combination with other therapeutic components are found as plant extracts. Fumiko et al. (Biol. Pharm. Bull (2002), 25(11), 1485-1487) discloses the evaluation of a methanolic extract of *Rosmarimus officinalis* L. for treating trypanosomiasis. Addington et al. (U.S. Pat. Nos. 8,481,086, 9,220,778, 9,358,293, US 20160243143 A1) disclose a supercritical fluid (SCF) extract (PBI-05204) of *Nerium oleander* containing oleandrin and triterpenes for the treatment of neurological conditions. Addington et al. (U.S. Pat. No. 9,011,937, US 20150283191 A1) disclose a triterpene-containing fraction (PBI-04711) of the SCF extract of *Nerium oleander* containing oleandrin and triterpenes for the treatment of neurological conditions. Jager et al. (Molecules (2009), 14, 2016-2031) disclose various plant extracts containing mixtures of oleanolic acid, ursolic acid, betulinic acid and other components. Mishra et al. (PLoS One 2016 25; 11(7):e0159430. Epub 2016 Jul. 25) disclose an extract of *Betula utilis* bark containing a mixture of oleanolic acid, ursolic acid, betulinic acid and other components. Wang et al. (Molecules (2016), 21, 139) disclose an extract of *Alstonia scholaris* containing a mixture of oleanolic acid, ursolic acid, betulinic acid and other components. L. e Silva et al. (Molecules (2012), 17, 12197) disclose an extract of *Eriope blanchetti* containing a mixture of oleanolic acid, ursolic acid, betulinic acid and other components. Rui et al. (Int. J. Mol. Sci. (2012), 13, 7648-7662) disclose an extract of *Eucaplyptus globulus* containing a mixture of oleanolic acid, ursolic acid, betulinic acid and other components. Ayatollahi et al. (Iran. J. Pharm. Res. (2011), 10(2), 287-294) disclose an extract of *Euphorbia microsciadia* containing a mixture of oleanolic acid, ursolic acid, betulinic acid and other components. Wu et al. (Molecules (2011), 16, 1-15) disclose an extract of *Ligustrum* species containing a mixture of oleanolic acid, ursolic acid, betulinic acid and other components. Lee et al. (Biol. Pharm. Bull (2010), 33(2), 330) disclose an extract of *Forsythia viridissima* containing a mixture of oleanolic acid, ursolic acid, betulinic acid and other components.

None of the art suggests a neuroprotective composition containing a combination of two or three different triterpenes selected from oleanolic acid, ursolic acid and betulinic acid, nor use of such a composition for the treatment of neurological conditions, in particular wherein the neuroprotective composition excludes cardiac glycoside and excludes a pharmacologically active polysaccharide obtained from *Nerium* species or *Thevetia* species. None of the art recognizes the improvements provided by administration of a combination of triterpenes as compared to administration of the individual triterpenes, in particular wherein cardiac glycoside is absent.

SUMMARY OF THE INVENTION

The invention provides a method of treating a neurological condition comprising administering to a subject in need thereof a neuroprotective composition comprising (consisting essentially of) at least two triterpenes. The invention also provides neuroprotective compositions comprising (consisting essentially of) at least three triterpenes. The present inventors have determined that the molar ratio of triterpenes has an impact upon efficacy and safety of the neuroprotective composition(s). Embodiments of the invention include those wherein the molar ratio of triterpenes is as described herein. The neuroprotective composition(s) optionally further comprise(s) at least one steroid, at least one steroid ester, or at least one non-cardiac glycoside steroid. In some embodiments, the neuroprotective compositions contain triterpenes as the sole pharmacologically active ingredients. In some embodiments, the neuroprotective composition(s) excludes steroid, cardiac glycoside, non-cardiac glycoside steroid, and/or pharmacologically active polysaccharide.

In some embodiments, the neuroprotective composition comprises a fraction of extract of *Nerium* species or *Thevetia* species in an effective amount to treat said neurological condition. In some embodiments, the fraction excludes oleandrin, neriifolin and pharmacologically active polysaccharide obtained from *Nerium* species or *Thevetia* species.

In one aspect, the invention provides a method of treating, in a subject in need thereof, a neurological disease or disorder with a neuroprotective composition comprising a fraction of extract of *Nerium* species or *Thevetia* species, the method comprising:

determining that the subject has a neurological disease or disorder; and indicating administration to the subject a therapeutically effective amount of the neuroprotective composition.

In one aspect, the invention provides a method of treating, in a subject in need thereof, a neurological disease or disorder with a neuroprotective composition, the method comprising:

determining that the subject has a neurological disease or disorder; and indicating administration to the subject a therapeutically effective amount of the neuroprotective composition.

The invention also provides a method of treating, in a subject in need thereof, a neurological disease or disorder with a neuroprotective composition comprising a fraction of extract of *Nerium* species or *Thevetia* species, the method comprising administering to the subject the neuroprotective composition.

The invention also provides a method of treating, in a subject in need thereof, a neurological disease or disorder with a neuroprotective composition, the method comprising administering to the subject a therapeutically effective amount of the neuroprotective composition.

Some embodiments of the invention include those wherein: 1) the subject is prescribed and administered a therapeutically relevant dose of the neuroprotective composition; 2) the subject is administered the neuroprotective composition according to a prescribed dosing regimen; 3) the neuroprotective composition comprises an extract comprising one or more therapeutically effective agents extracted from the *Nerium* species or *Thevetia* species; 4) the neuroprotective composition further comprises one or more other therapeutically effective agents; 5) the neuroprotective composition comprises an extract obtained by extraction of *Nerium* species or *Thevetia* species with hot water, cold water, supercritical fluid, organic solvent or a combination thereof; 6) the neuroprotective composition excludes cardiac glycoside; 7) the neuroprotective composition excludes a therapeutically effective amount of cardiac glycoside; 8) the neuroprotective composition excludes oleandrin; 9) the neuroprotective composition comprises a fraction of an extract of *Nerium* species or *Thevetia* species; 10) the neuroprotective composition comprises a fraction of an extract of *Nerium* species or *Thevetia* species, wherein the fraction has been prepared by liquid chromatographic fractionation of the extract; 11) the *Nerium* species is *Nerium oleander* and the *Thevetia* species is *Thevetia nernfolia;* 12) the neuroprotective composition excludes neriifolin; 13) the neuroprotective composition comprises a sub-fraction of a fraction of an extract of *Nerium* species or *Thevetia* species, wherein the sub-fraction has been prepared by liquid chromatographic fractionation of a fraction of the extract, and the sub-fraction excludes oleandrin and neriifolin; 14) the neuroprotective composition excludes a pharmacologically active polysaccharide obtained from *Nerium* species or *Thevetia* species; 15) the neuroprotective composition comprises a mixture of triterpenes as the sole or primary pharmacologically active ingredient(s); or 16) a combination of any of the above.

The invention also provides a method of treating a neurological condition in a subject in need thereof comprising:

determining whether or not the neurological condition in the subject is Alzheimer's disease, Huntington's disease, stroke, Parkinson's disease or other neurological condition;

indicating administration of a neuroprotective composition;

administering an initial dose of the neuroprotective composition to the subject according to a prescribed initial dosing regimen for a period of time;

periodically determining the adequacy of the subject's clinical response and/or therapeutic response to treatment with the extract; and if the subject's clinical response and/or therapeutic response is adequate, then continuing treatment with neuroprotective composition as needed until the desired clinical endpoint is achieved; or if the subject's clinical response and/or therapeutic response are inadequate at the initial dose and initial dosing regimen, then escalating or deescalating the dose of neuroprotective composition until the desired clinical response and/or therapeutic response in the subject is achieved.

The invention also provides a method of preventing or reducing the incidence of occurrence of a neurological condition in a population of subjects at risk thereof, the method comprising:

administering an effective dose of neuroprotective composition on a recurring basis for an extended period of time to one or more subjects in a population of subjects at risk of suffering from a neurological condition such as Alzheimer's disease, Huntington's disease, Parkinson's disease, stroke or other neurological condition, thereby preventing or reducing the incidence of the neurological condition in the population.

The invention also includes embodiments wherein: a) the method further comprises indicating administration of the neuroprotective composition to the one or more subjects; b) the method further comprises administering an effective dose of the neuroprotective composition to the subject according to a prescribed dosing regimen for a period of time; c) the method further comprises periodically determining the adequacy of one or more subject's clinical response and/or therapeutic response to treatment with the neuroprotective composition; d) if the subject's clinical response and/or therapeutic response is adequate, then the method further comprises continuing treatment with the neuroprotective composition as needed until the desired clinical endpoint is achieved; e) if the subject's clinical response and/or therapeutic response are inadequate at the initial dose and initial dosing regimen, then the method further comprises escalating or deescalating the dose of neuroprotective composition until the desired clinical response and/or therapeutic response in the subject is achieved; f) the neuroprotective composition is administered to plural subjects in a population; g) the recurring basis is daily, every other day, every second day, every third day, every fourth day, every fifth day, every sixth day, weekly, every other week, every second week, every third week, monthly, bimonthly, semi-monthly, every other month every second month, quarterly, every other quarter, trimesterly, seasonally, semiannually and/or annually; h) the extended period is one or more weeks, one or more months, one or more quarters and/or one or more years; i) the effective dose is administered one or more times in a day; j) the method further comprises identifying a population of subjects at risk of suffering from a neurological condition such as Alzheimer's disease, Huntington's disease, Parkinson's disease, stroke or other neurological condition; k) the population of subjects at risk is characterized by advancing age of the subject, familial history of the neurological condition, genetic predisposition to occurrence of neurological condition, the presence and expression of ApoE4 gene in the subject, female gender (twice as many women get Alzheimer's disease than men), cardiovascular disease (e.g. high blood pressure and high cholesterol levels), diabetes (especially Type 2 or adult onset forms of this disease), Down's Syndrome, head injury, low levels of formal education, smoking, excessive alcohol consumption and/or drug abuse; 1) the neuroprotective composition excludes a therapeutically effective amount of cardiac glycoside; m) the neuroprotective composition excludes cardiac glycoside; n) the neuroprotective composition excludes a pharmacologically active polysaccharide obtained from *Nerium* species or *Thevetia* species; or o) a combination of any two or more of the above.

The invention also provides a time-delayed method of treating stroke in a subject comprising:

within a delay period after a subject has suffered the stroke, administering an initial dose of neuroprotective composition according to an initial dosing regimen;

determining the adequacy of subject's clinical response and/or therapeutic response to treatment with the neuroprotective composition; and if the subject's clinical response and/or therapeutic response is adequate, then continuing treatment with neuroprotective composition as needed until the desired clinical endpoint is achieved; or if the subject's clinical response and/or therapeutic response are inadequate at the initial dose and initial dosing regimen, then escalating or deescalating the dose of neuroprotective composition until the desired clinical response and/or therapeutic response in the subject is achieved.

Some embodiments of the invention include those wherein: 1) the delay period is 10 hours or less, 8 hours or less, 6 hours or less, 4 hours or less, 3 hours or less, 2 hours or less, 1 hour or less, 45 minutes or less, 30 minutes or less, 20 minutes or less or 10 min or less; 2) determining the adequacy of a subject's clinical and/or therapeutic response is done by assessments of any weakness of the face, arm and/or leg on one side of the body, numbness in the face, arm, and/or leg on one side of the body, inability to understand spoken language, inability to speak or speak clearly, inability to write, vertigo and/or gait imbalance, double vision and an unusually severe headache; or 3) a combination of any two or more of the above thereof.

The invention also provides use of a neuroprotective composition in the manufacture of a medicament for the treatment of a neurological condition in a subject. In some embodiments, the manufacture of such a medicament comprises: providing a neuroprotective composition; including a dose of neuroprotective composition, or a fraction thereof, in a pharmaceutical dosage form; and packaging the pharmaceutical dosage form. The invention also provides a pharmaceutical composition comprising a neuroprotective composition for the treatment of a neurological condition in a subject. In some embodiments, the manufacture can be conducted as described in PCT International Application No. PCT/US06/29061 filed Jul. 26, 22006, U.S. Pat. No. 7,402,325 issued Jul. 22, 2008, U.S. Pat. No. 8,187,644 issued May 29, 2012, or U.S. Pat. No. 8,394,434 issued Mar. 12, 2013, the entire disclosures of which are hereby incorporated by reference. The neuroprotective composition can also be manufactured by mixing the specified components to form a mixture thereof. The manufacture can also include one or more additional steps such as: delivering the packaged dosage form to a vendor (retailer, wholesaler and/or distributor); selling or otherwise providing the packaged dosage form to a subject having a neurological condition; including with the medicament a label and a package insert, which provides instructions on use, dosing regimen, administration, content and toxicology profile of the dosage form. In some embodiments, the treatment of a neurological condition comprises: determining that a subject has a neurological disease or disorder; indicating administration of a neuroprotective composition, or a fraction thereof, to the subject according to a dosing regimen; administering to the subject one or more pharmaceutical dosage forms containing the extract, wherein the one or more pharmaceutical dosage forms is administered according to the dosing regimen.

The invention also provides a neuroprotective composition, such as a fraction or sub-fraction of an extract of *Nerium* species or *Thevetia* species, or a composition, i.e. a pharmaceutical formulation or dosage form, comprising an extract of *Nerium* species or *Thevetia* species for the treatment of a neurological condition. In some embodiments, the extract can be obtained from *Nerium* species or *Thevetia* species as described herein or in U.S. Pat. No. 7,402,325, PCT International Application No. PCT/US06/29061, U.S. application Ser. No. 12/019,435, or Newman et al. (*Mol. Interven.* (2008), 8, 36-49), U.S. Pat. No. 7,402,325 issued Jul. 22, 2008, U.S. Pat. No. 8,187,644 issued May 29, 2012, or U.S. Pat. No. 8,394,434 issued Mar. 12, 2013, the entire disclosures of which are hereby incorporated by reference. In some embodiments, the extract comprises oleandrin and at least two or at least three triterpenes. The triterpenes in the extract can be selected from oleanolic acid, ursolic acid, betulinic acid and others discussed herein or known to be present in a plant mass comprising *Nerium* species or *Thevetia* species. The supercritical fluid extract PBI-05204 of *Nerium* species has been found to comprise oleandrin, oleanolic acid (O), ursolic acid (U) and betulinic acid (B), wherein the molar ratio of the triterpenes is about 7.8 O:about 7.4 U:about 1 B.

The invention also provides a method for preparing a fraction of extract of *Nerium* species or *Thevetia* species comprising: extracting a mass comprising *Nerium* species or *Thevetia* species to form an unfractionated extract thereof, the extract comprising one or more pharmacologically active (therapeutically effective) components for the treatment of a neurological condition; and fractionating the extract to form two or more fractions thereof, wherein at least one fraction comprises one or more non-cardiac glycoside pharmacologically active components. In some embodiments, a) at least one fraction excludes cardiac glycoside; b) at least one second fraction further comprises cardiac glycoside; c) the extraction is conducted with supercritical fluid, water, organic solvent or a combination thereof d) the fractionation is conducted by liquid chromatography or solvent extraction; e) the at least one fraction excludes pharmacologically active polysaccharide obtained from *Nerium* species or *Thevetia* species, excludes oleandrin and excludes neriifolin; f) the at least one fraction consists essentially of at least two or at least three triterpenes as detailed herein; or f) a combination of any two or more of the above.

The invention also provides a method of fractionating an extract of *Nerium* species or *Thevetia* species in order to provide one or more therapeutically effective fractions thereof. The method comprises: a) providing an extract of *Nerium* species or *Thevetia* species; b) fractionating the extract to provide two or more different fractions of the extract, a first extract fraction comprising one or more pharmacologically active agents, which is/are not a cardiac glycoside, and excluding cardiac glycoside (oleandrin and neriifolin), and a second extract fraction comprising one or more cardiac glycosides and one or more pharmacologically active agents, which is/are not a cardiac glycoside. The fractionation can also be performed as described herein. In some embodiments, the first or second extract fraction is subjected to further fractionation to provide two or more different sub-fractions, wherein a first sub-fraction comprises one or more steroids and a second sub-fraction comprises one or more triterpenes. In some embodiments, the fractionation is performed by liquid chromatography with a stationary phase and a mobile phase.

The invention also provides a neuroprotective composition comprising a fraction of an extract obtained from *Nerium* species or *Thevetia* species, whereby the fraction has been obtained by fractionation of the extract obtained from *Nerium* species or *Thevetia* species. In some embodiments, a fraction of extract comprises one or more steroids and one or more tritepenes and optionally excludes cardiac glycoside (oleandrin and neriifolin). In some embodiments, a fraction of extract comprises two or more tritepenes and excludes cardiac glycoside (oleandrin and neriifolin) and excludes pharmacologically active polysaccharide obtained from *Nerium* species or *Thevetia* species.

The invention also provides a neuroprotective composition comprising a sub-fraction of fraction of an extract obtained from *Nerium* species or *Thevetia* species, whereby the sub-fraction has been obtained by further fractionation of a fraction of the extract obtained from *Nerium* species or *Thevetia* species. In some embodiments, a sub-fraction of a fraction of extract comprises one or more steroids, cardiac glycosides, the associated aglycones of cardiac glycosides, e.g. oleandrigenin, cardenolides, or triterpenoids, and one or more tritepenes. In some embodiments, a sub-fraction of a fraction of extract comprises one or more triterpenes and excludes a steroid. Each sub-fraction independently optionally excludes cardiac glycoside (oleandrin and neriifolin). In some embodiments, the sub-fraction comprises at least two triterpenes, and excludes a non-cardiac glycoside steroid, cardiac glycoside and pharmacologically active polysaccharide obtained from *Nerium* species or *Thevetia* species.

In some embodiments: a) the extract further comprises at least two pharmacologically active agents obtained (extracted) from *Nerium* species or *Thevetia* species; b) the at least two pharmacologically active agents function additively or synergistically to contribute to the therapeutic efficacy of the extract when the extract is administered to a subject; c) none of the at least two pharmacologically active agents is a cardiac glycoside; and/or d) at least two pharmacologically active agents/components are selected from the group of cardiac glycosides, the associated aglycones of cardiac glycosides, e.g. oleandrigenin, cardenolides or triterpenoids.

In some embodiments: 1) the cardiac glycoside is selected from the group consisting of oleandrin, odoroside, neritaloside, ouabain, bufalin, digitoxin, cinobufatalin, cinobufagin, and resibufogenin; 2) the extract is present in a pharmaceutical formulation or composition; 3) the extract has been obtained from an *oleander* plant mass or *neriifolia* plant mass; 4) the plant mass comprises *Nerium* species, such as *Nerium oleander*, or *Thevetia* species, such as *Thevetia neriifolia* or *Thevetia peruviana* (otherwise known as yellow *oleander*); 5) the extract was prepared by supercritical fluid (SCF) extraction optionally in the presence of a modifier; 6) the cardiac glycoside is oleandrin; 7) the extract was prepared by hot water extraction, cold water extraction, organic solvent extraction or aqueous organic solvent extraction.

In some embodiments, the extract (or fraction or sub-fraction thereof) comprises less than 1% wt., less than 0.5% wt., less than 0.1% wt., less than 0.05% wt. or less than 0.01% wt. of or excludes pharmacologically active polysaccharide obtained from *Nerium* species or *Thevetia* species.

In some embodiments, the extract (or fraction or sub-fraction thereof) comprises betulin (urs-12-ene-3β,28-diol); 28-norurs-12-en-3β-ol; urs-12-en-3β-ol; 3β,3β-hydroxy-12-oleanen-28-oic acid; 3β,20α-dihydroxyurs-21-en-38-oic acid; 3β,27-dihydroxy-12-ursen-38-oic acid; 3β,13β-dihydroxyurs-11-en-28-oic acid; 3β,12α-dihydroxyoleanan-28, 13β-olide; and 3β,27-dihydroxy-12-oleanan-28-oic acid. In some embodiments, the extract (or fraction or sub-fraction thereof) comprises one or more cardiac glycoside precursors selected from a glycone constituent of a cardiac glycoside. In some embodiments, the glycone is selected from the group consisting of glucoside, fructoside, and glucuronide.

In some embodiments, the extract (or fraction or sub-fraction thereof) comprises oleandrigenin, ursolic acid, betulinic acid, odoroside, neritaloside, oleanolic acid and optionally one or more other triterpenes and excludes pharmacologically active polysaccharide obtained from *Nerium* species or *Thevetia* species.

Some embodiments of the invention provide a neuroprotective composition comprising (consisting essentially of) at least oleanolic acid (triterpene), betulinic acid (triterpene), and ursolic acid (triterpene). Some embodiments of the invention provide a neuroprotective composition comprising (consisting essentially of) at least oleanolic acid (triterpene) and ursolic acid (triterpene).

In some embodiments, the neuroprotective composition further comprises at least one of ursolic aldehyde (triterpene), uvaol (3β,28-dihydroxyurs-12-ene, triterpene), 3β,27-dihydroxy-12-ursen-28-oic acid (triterpene), or 27-(p-Coumaroyloxy)ursolic acid isomers (triterpene). In some embodiments, the neuroprotective composition excludes pharmacologically active polysaccharide obtained from *Nerium* species or *Thevetia* species, oleandrin and neriifolin. In some embodiments, the neuroprotective composition comprises at least three, at least four, at least five, at least six or at least seven triterpenes. In some embodiments, the fraction excludes a non-cardiac glycoside steroid.

In some embodiments, the subject having a neurological condition, i.e. the subject in need thereof, is part of a population of such subjects. The invention provides a method for improving the clinical status of a statistically significant number of subjects of in a population of subjects having a neurological condition, the method comprising: administering to the population of subjects a neuroprotective composition as described herein; and determining the clinical status of the subjects. In some embodiments, the statistically significant number is at least 5% of the population.

In some embodiments, the neurological condition is Alzheimer's disease, Huntington's disease, stroke, Parkinson's disease, a tauopathy or other neurological condition, such as described herein. The medicament can be manufactured by inclusion of the neuroprotective composition in a pharmaceutical dosage form containing one or more pharmaceutically acceptable excipients.

Treatment of the subject with neuroprotective composition is continued as needed. The dose or dosing regimen can be adjusted as needed until the patient reaches the desired clinical endpoint(s) such as a reduction or alleviation of specific neurological symptoms associated with the disease. Determination of the adequacy of clinical response and/or therapeutic response can be conducted by a clinician familiar with the neurological condition being treated.

In some embodiments, the neurological condition is selected from the group consisting of neurological disease, neurological disorder, tauopathy, and stroke. In some embodiments, the neurological disease is a neurodegenerative disease. In some embodiments, the neurodegenerative disease is selected from the group consisting of Huntington's disease, Alzheimer's disease, Parkinson's disease, stroke, amyotrophic lateral sclerosis, bovine spongiform encephalopathy, multiple sclerosis, diabetic neuropathy, autism and juvenile neuronal ceroid lipofuscinosis. In some embodiments, stroke is stroke-mediated ischemic injury. In some embodiments, the neurological condition is a tauopathy, which is a neurodegenerative disease having an etiology associated with an imbalance in the Tau3R/Tau4R ratio in a subject. Tauopathies are a class of neurodegenerative diseases resulting from the pathological aggregation of tau proteins in the human brain. In some embodiments, the tauopathy is Down's syndrome, Pick's disease, corticobasal degeneration, some variants of prions disease, Alzheimer's disease, progressive supranuclear palsy or frontotemporal dementia. The individual steps of the methods of the invention can be conducted at separate facilities or within the same facility.

In some embodiments, the neurons are in vitro, ex vivo or in vivo. In some embodiments, the neurons are CA-1 neurons.

In some embodiments, the invention provides an extract, or fraction thereof or sub-fraction thereof, of *Nerium* species or *Neriifolia* species, having a $^1$HNMR spectrum as described herein. In some embodiments, the invention provides a neuroprotective composition, e.g. an extract, or fraction thereof or sub-fraction thereof, of *Nerium* species or *Neriifolia* species, exhibiting therapeutic activity as described herein when administered to a subject. In some embodiments, the invention provides a neuroprotective composition e.g, an extract, or fraction thereof or sub-fraction thereof, of *Nerium* species or *Neriifolia* species, having a HPLC chromatogram as described herein. In some embodiments, the methods of the invention employ a neuroprotective composition as described herein. In some embodiments, the neuroprotective compositions of the invention comprise an extract, fraction thereof or sub-fraction thereof, as described herein.

In some embodiments, the neuroprotective composition of the invention comprises at least two triterpenes. The neuroprotective composition may or may not be a fraction or sub-fraction of the extract. For example, the invention provides a neuroprotective composition comprising (consisting essentially of) a combination of at least ursolic acid and oleanolic acid, or a combination of at least oleanolic acid and betulinic acid. In some embodiments, the composition of the invention comprises (consists essentially of) at least three triterpenes. In some embodiments, the composition of the invention comprises (consists essentially of) oleanolic acid, ursolic acid and at least one other triterpene. For example, the composition can further comprise betulinic acid or at least one other triterpene. The composition can further comprise one or more other pharmacologically active components ingredients extracted from *Nerium* species or *Thevetia* species. In some embodiments, the neuroprotective composition comprises (consists essentially of) the triterpenes ursolic acid, oleanolic acid and betulinic acid, wherein the molar ratio of triterpenes is as described herein.

In some embodiments, the neuroprotective composition comprises (consists essentially of) oleanolic acid, ursolic acid, and betulinic acid. In some embodiments, the neuroprotective composition further comprises at least one other therapeutically effective agent extracted from *Nerium* species or *Thevetia* species.

When oleanolic acid and ursolic acid are present, the molar ratio of oleanolic acid (O):ursolic acid (U) is about 4-2 O:3-1 U, or about 3-3.5 O:about 2-2.5 U, or about 3 O:about 2 U, or about 3.2 O:about 2.3 U, or about 7.8 O:about 7.4 U, or about 0.8-1.2 O:1.2-0.8 U, or about 7-8 O:about 7-8 U, or about 7.5 O:about 7.7 U, or about 4-2 O: 0.1-1.5 U, 3-3.5 O:about 0.8-1.2 U, or about 3 O:1 U, or about 3.2 O:about 1 U, or about 7.8 O:about 1 U, or about 7-8 O:1.2-0.8 U, or about 7-8 O:about 1.1-0.9 U, or about 7-8 O:about 1 U.

When oleanolic acid and betulinic acid are present, the molar ratio of oleanolic acid (O):betulinic acid (B) is about 4-2 O:3-1 B, or about 3-3.5 O:about 2-2.5 B, or about 3 O:about 2 B, or about 3.2 O:about 2.3 B, or about 7.8 O:about 7.4 B, or about 0.8-1.2 O:1.2-0.8 B, or about 7-8 O:about 7-8 B, or about 7.5 O:about 7.7 B, or about 4-2 O: 0.1-1.5 B, 3-3.5 O:about 0.8-1.2 B, or about 3 O:1 B, or about 3.2 O:about 1 B, or about 7.8 O:about 1 B, or about 7-8 O:1.2-0.8 B, or about 7-8 O:about 1.1-0.9 B, or about 7-8 O:about 1 B.

When oleanolic acid, ursolic acid and betulinic acid are present, the molar ratio of oleanolic acid (O):ursolic acid (U):betulinic acid (B) is about 4-2 O:3-1 U:0.1-1.5 B, or about 3-3.5 O:about 2-2.5 U:about 0.8-1.2 B, or about 3 O:2 U:1 B, or about 3.2 O:about 2.3 U:about 1 B, or about 7.8 O:about 7.4 U:about 0.8-1.2 B, or about 7-8 O:about 7-8 U:about 0.8-1.2 B, or about 7.8 O:about 7.4 U:about 0.9-1.1 B, or about 7.8 O:about 7.4 U:about 1 B, or about 3 O:2 U:1 B, or about 4-2 O:about 3-1 U:about 1 B.

The individually named triterpenes are independently selected upon each occurrence from their native (unmodified, free acid) form, salt form, derivative form, prodrug form, or a combination thereof.

The individual steps of the methods of the invention can be conducted at separate facilities or within the same facility.

In some embodiments, the neurons are in vitro, ex vivo or in vivo. In some embodiments, the neurons are CA-1 neurons.

Any of the methods of the invention described herein can be used in combination with any of the compositions of the invention described herein.

The invention includes all combinations of the aspects, embodiments and sub-embodiments of the invention disclosed herein. Unless otherwise specified herein, the term "extract" can refer to the unfractionated extract or fractionated extract, i.e. a fraction of the extract, or sub-fractionated extract, i.e. a sub-fraction of a fraction of the extract.

BRIEF DESCRIPTION OF THE FIGURES

The following figures form part of the present description and describe exemplary embodiments of the claimed invention. The skilled artisan will, in light of these figures and the description herein, be able to practice the invention without undue experimentation.

FIGS. 9A-9I depict $^1$HNMR spectra for various components present in the Fraction 0-4 Nerium oleander SCF extract. FIG. 9A depicts the $^1$HNMR spectrum of the Fraction 0-4 before sub-fractionation according to Example 17. FIGS. 9B-9I depict the $^1$HNMR spectra for various sub-fractions obtained by silica gel flash chromatography, according to Example 17, performed on the Fraction 0-4.

FIGS. 15A-15D depict the results of expression assays for Fraction 0-4: a) Gclc expression (FIG. 15A); b) Nqo1 expression (FIG. 15B); c) Srx expression (FIG. 15C); and d) Hmox1 expression (FIG. 15D). Fraction 0-4 induces robust upregulation of canonical ARE target genes, shown here for glutamate-cysteine ligase, catalytic subunit (Gclc); NAD(P)H:quinone oxidoreductase 1 (Nqo1); sulfiredoxin antioxidant protein (Srx); and heme oxygenase 1 (Hmox1)). Primary mouse corticostriatal co-cultures were treated with Fraction 0-4 at the concentrations indicated for 6 h, then harvested and processed for qPCR analysis of the ARE target genes shown. Quantitative RNA values are normalized to the GAPDH reference control and fold-expression changes are expressed relative to the DMSO-carrier only condition ("0") set to a value of 1.

DETAILED DESCRIPTION OF THE INVENTION

Figure 1A:
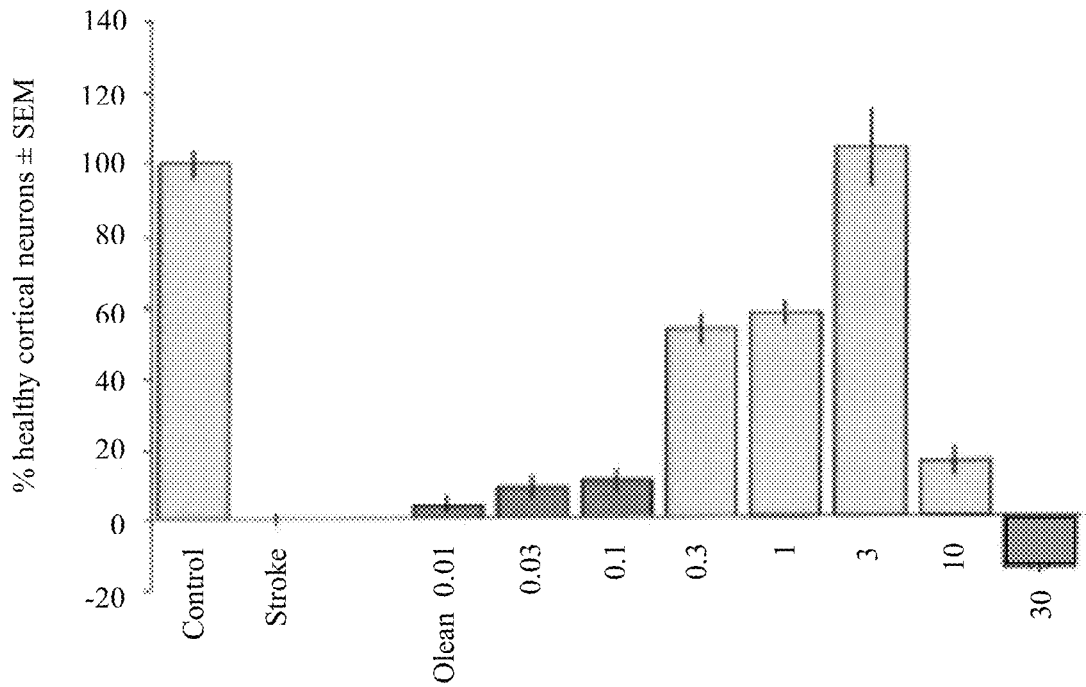
FIG. 1A depicts concentration-response data obtained from the comparative evaluation of the oleandrin versus no oxygen or glucose deprivation (OGD), the control, in a neuroprotection brain-slice-based "stroke" assay (Example 8), wherein the number of healthy cortical neurons is determined following 5-6 minutes of oxygen and glucose deprivation (OGD=stroke) in the presence or absence of oleandrin.

The invention provides a method of treating a neurological condition by administration of an effective dose (therapeutically effective dose) of neuroprotective composition to a subject in need thereof. The neuroprotective composition is administered according to a dosing regimen best suited for the subject, the suitability of the dose and dosing regimen to be determined clinically according to conventional clinical practices and clinical treatment endpoints for the neurological condition being treated.

In some embodiments, the neurodegenerative disorder or neurological condition being treated has an etiology associated with an over-expression of tau proteins and/or an imbalance in the Tau3R/Tau4R ratio in a subject. Such a condition is termed a tauopathy. Exemplary tauopathies include Down's syndrome, Pick's disease, some variants of prions disease, Alzheimer's disease, progressive supranuclear palsy or frontotemporal dementia, corticobasal degeneration, Guam parkinsonism dementia complex, dementia with argyrophilic grains, Niemann-Pick disease Type C, and dementia pugilistic.

In some embodiments, the neurodegenerative disorder or neurological condition being treated is Parkinson's disease.

In some embodiments, the neurodegenerative disorder or neurological condition being treated has an etiology associated with abnormal or atypical proteolysis of amyloid beta precursor protein, accumulation of amyloid beta protein in the synapses of the neurons, formation of amyloid fibrils in the synapses of the neurons, or formation of amyloid plaques in the synapses of the neurons. Exemplary of such disorders or conditions is Alzheimer's disease. A subject treated according to the invention will exhibit a therapeutic response. By "therapeutic response" is meant that a subject suffering from the disease or disorder will enjoy at least one of the following clinical benefits as a result of treatment with the neuroprotective composition: amelioration of the disease or disorder, reduction in the occurrence of symptoms associated with the disease or disorder, partial remission of the disease or disorder, full remission of the disease or disorder, or increased time to progression. In other words, the therapeutic response can be a full or partial therapeutic response.

A therapeutic response can also be described as one in which the quality of life of the patient afflicted with the neurodegenerative disease is improved. Improvement in quality of life may occur, for example, through a reduction in occurrence, frequency or severity of symptoms associated with the disease (e.g. tremors, involuntary muscle movements, loss or partial loss of nerve-muscle coordination, memory retention, etc.).

"Preventing occurrence of a neurological condition in a population of subjects at risk" means that the neurological condition will not occur during a predetermined time period in a demographically predetermined population of subjects that are at risk of suffering from the neurological condition. The prevention during the predetermined time period occurs as a result of subjects in that population having been administered an neuroprotective composition according to the invention. As one example, when a neuroprotective composition or extract-containing composition is administered for a predetermined time period to subjects in a population of subjects at risk of suffering from stroke, stroke will not occur in those subjects during the predetermined time period. In particular, a neuroprotective composition is chronically administered over a period of one year to a population of subjects at risk of suffering from Alzheimer's disease or any of the tauopathology related diseases, and the subjects in that population do not exhibit symptoms associated with Alzheimer's during that one-year period.

"Reducing the incidence of occurrence of a neurological condition in a population of subjects at risk" is related in meaning to "preventing the incidence", except that "reducing the incidence of occurrence" permits the occurrence of the neurological condition in a demographically predetermined population of subjects but at a rate of occurrence or a level of severity that is reduced as compared to an otherwise demographically similar predetermined population of subjects at risk not being administered the neuroprotective composition according to the invention.

As used herein, "time to progression" is the period, length or duration of time after a disease is diagnosed (or treated) until the disease begins to worsen. It is the period of time during which the level of a disease is maintained without further progression of the disease, and the period of time ends when the disease begins to progress again. Progression of a disease is determined by "staging" a subject suffering from a neurological condition prior to or at initiation of therapy. For example, the subject's neurological health is determined prior to or at initiation of therapy. The subject is then treated with the neuroprotective composition, and the neurological health monitored periodically. At some later point in time, the symptoms of the neurological condition may worsen, thus marking progression of the disease and the end of the "time to progression". The period of time during which the disease did not progress or during which the level or severity of the disease did not worsen is the "time to progression".

A dosing regimen includes a therapeutically relevant dose (or therapeutically effective dose) of neuroprotective composition administered according to a dosing schedule. A therapeutically relevant dose, therefore, is a therapeutic dose at which a therapeutic response of the disease or disorder to treatment with neuroprotective composition is observed and at which a subject can be administered the neuroprotective composition without an excessive amount of unwanted or deleterious side effects. A therapeutically relevant dose is non-lethal to a subject, even though it may cause some side effects in the patient. It is a dose at which the level of clinical benefit to a subject being administered the neuroprotective composition exceeds the level of deleterious side effects experienced by the subject due to administration of the neuroprotective composition. A therapeutically relevant dose will vary from subject to subject according to a variety of established pharmacologic, pharmacodynamic and pharmacokinetic principles. However, a therapeutically relevant dose will typically be in the range of 0.1 to 100 micrograms of neuroprotective composition, extract (or fraction thereof)/day, the extract (or fraction thereof) being in either solid, liquid or semisolid form. It is known in the art that the actual amount of a pharmacologically active component/agent required to provide a target therapeutic result in a subject may vary from subject to subject according to the basic principles of pharmacy.

A therapeutically relevant (effective) dose can be administered according to any dosing regimen typically used in the treatment of neurological or neurodegenerative diseases or disorders. A therapeutically relevant dose can be administered once, twice, thrice or more daily dosing schedule. It can be administered every other day, every third day, every fourth day, every fifth day, semiweekly, weekly, biweekly, every three weeks, every four weeks, monthly, bimonthly, semimonthly, every three months, every four months, semiannually, annually, or according to a combination of any of the above to arrive at a suitable dosing schedule. For example, a therapeutically relevant dose can be administered once daily for one or more weeks.

The examples below include evidence of the efficacy of the neuroprotective composition, e.g. synthetic mixture, extract or a fraction or sub-fraction thereof, in neurological conditions such as neurological diseases, neurological disorders and stroke. Example 3 details a method of treating Alzheimer's disease with a *Nerium* species extract, or fraction thereof or composition thereof, *Thevetia* species extract, or fraction thereof, or composition thereof, or a combination thereof with one or more other therapeutic agents. Example 4 details a method of treating Huntington's disease with the extract, or fraction thereof, or a combination of the extract with one or more other therapeutic agents. Example 5 details a method of treating stroke-mediated and non-stroke mediated ischemic brain injury with the extract or a combination of the extract, or fraction thereof, with one or more other therapeutic agents.

In general, a subject having a neurological condition is treated as follows. A subject presenting with a neurological condition is evaluated to determine whether or not the neurological condition is Alzheimer's disease, Huntington's disease, stroke, Parkinson's disease or other neurological condition. If the subject has a positive diagnosis, administration of the neuroprotective composition or extract(fraction)-containing composition is indicated. Initial doses of the composition are administered to the subject according to a prescribed dosing regimen for a period of time. The subject's clinical response and level of therapeutic response are determined periodically. If the level of therapeutic response is too low at one dose, then the dose is escalated according to a predetermine dose escalation schedule until the desired level of therapeutic response in the subject is achieved. If the subject exhibits undesirable side effects or an unacceptable level of side effects, then the dose is deescalated until the desired balance of level of therapeutic response versus side effect profile in the subject is achieved. Treatment of the subject with the extract (fraction) or neuroprotective composition is continued as needed. The dose or dosing regimen can be adjusted as needed until the patient reaches the desired clinical endpoint(s) such as cessation of the disease itself, reduction in disease associated symptoms, and/or a reduction in the progression of the disease process.

The extract, in particular unfractionated extract, comprises one or more pharmacologically active compounds (component, agent). Some of those compounds are as yet unidentified and some can be oleandrin or other cardiac glycosides, oleaside, oleandrigenin, neritaloside, odoroside (Wang X, Plomley J B, Newman R A and Cisneros A. LC/MS/MS analyses of an *oleander* extract for cancer treatment, *Analytical Chem.* 72: 3547-3552, 2000), and other plant materials. Unfractionated SCF extract from a supercritical fluid process typically contains a theoretical range of 0.9% to 2.5% by weight of oleandrin. SCF extracts comprising varying amount of oleandrin have been obtained. In one embodiment, the SCF extract comprises about 2% by wt. of oleandrin. In some embodiments, the SCF extract PBI-05204 comprises at least oleandrin, oleanolic acid, ursolic acid and betulinic acid. In some embodiments, the SCF extract excludes neriifolin and polysaccharide obtained during SCF extraction of plant material.

The extractable unidentified components of the extract of *Nerium* species or *Thevetia* species can comprise at least one (non-cardiac glycoside) pharmacologically active component that contributes to the efficacy of the SCF extract or a fraction thereof. Two or more pharmacologically active extractable components can function additively or synergistically to provide the observed efficacy. In other words, the *Nerium* species or *Thevetia* species extract of the invention comprises one or more pharmacologically active components that are not a cardiac glycoside, even though one or more cardiac glycosides can additionally be included in the extract.

The extract can be fractionated into various different fractions some of which contain cardiac glycoside, one or more non-cardiac glycoside pharmacologically active components or a combination thereof. In addition, each fraction of extract can be further fractionated into two or more different sub-fractions. In some embodiments, a fraction or sub-fraction of the extract comprises (or consists essentially of or consists of) oleanolic acid, ursolic acid and betulinic acid.

Figure 1B:
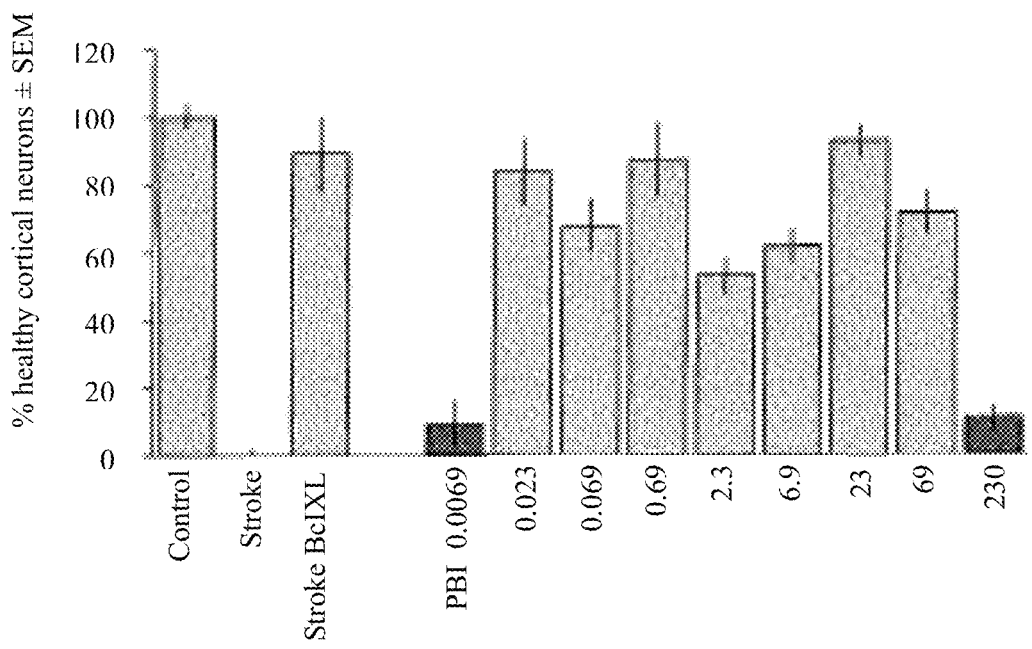
FIG. 1B depicts results of a concentration-response assay for unfractionated SCF extract (also referred to as PBI-05204) of *Nerium oleander* in a neuroprotection brain-slice-based "stroke" assay as described herein (Example 8), wherein no oxygen or glucose deprivation is used as the control.

Evidence of the existence of one or more pharmacologically active components, other than oleandrin, in the SCF extract was obtained by comparing the concentration-response curves for a solution containing pure oleandrin versus one containing the SCF extract. FIG. 1A depicts the results of a concentration-response assay for a solution containing pure oleandrin in a neuroprotection brain-slice-based "stroke" assay as described in Example 8. The concentration of oleandrin in the solution was varied from 0.0069 to 230 μg/ml. FIG. 1B depicts results of a concentration-response assay for an oleandrin-containing SCF Nerium species extract in a neuroprotection brain-slice-based "stroke" assay as described herein (Example 8). The data demonstrate that the extract is more efficacious that pure oleandrin meaning the extract contains one or more pharmacologically active agents that provide neuroprotection. The one or more pharmacologically active agents include at least oleanolic acid and ursolic acid and can further include betulinic acid.

Example 8 provides a detailed description of an in vitro assay used to evaluate the efficacy of the extract, or fraction thereof, or composition thereof, for the treatment of stroke-mediated ischemic neuronal injury. The assay is a brain slice-based assay for oxygen and glucose deprivation (OGD) used to induce 50% loss of healthy cortical neurons by 24 hours. The parent unfractionated SCF extract of Nerium species, e.g. Nerium oleander, is used as a positive control. The parent extract is then fractionated according to Example 13 to provide a fraction of extract of Nerium species. The fractions are analyzed according to Examples 6, 14 and 17.

The SCF extract comprises oleandrin, triterpene(s) and possibly minor amounts of other pharmacologically active component(s). The triterpenes include at least oleanolic acid and ursolic acid and optionally further include betulinic acid. The SCF extract can be fractionated, as described herein, to provide fraction(s) comprising oleandrin, fraction (s) comprising triterpene(s) and fraction(s) comprising other pharmacologically active component(s).

Figure 9B:
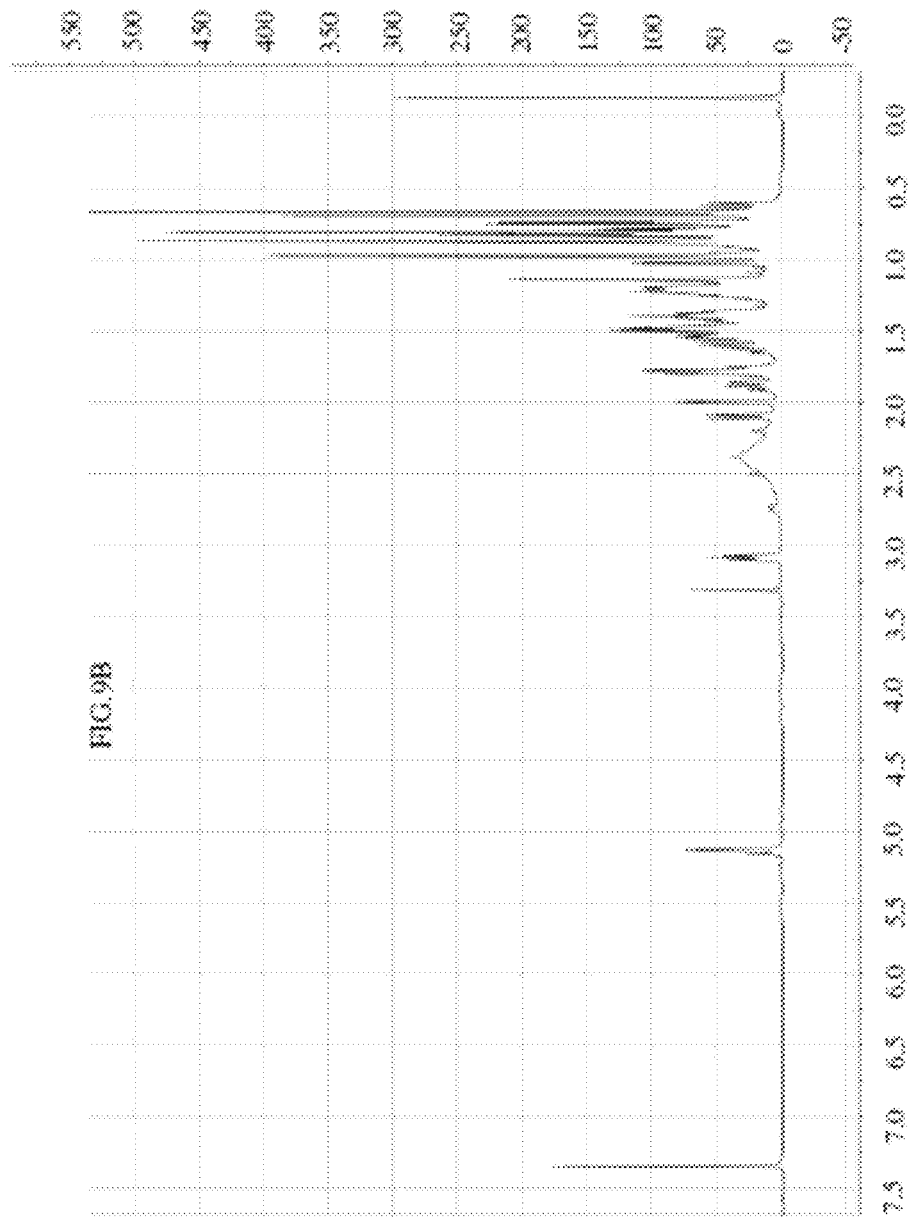
Figure 9C:
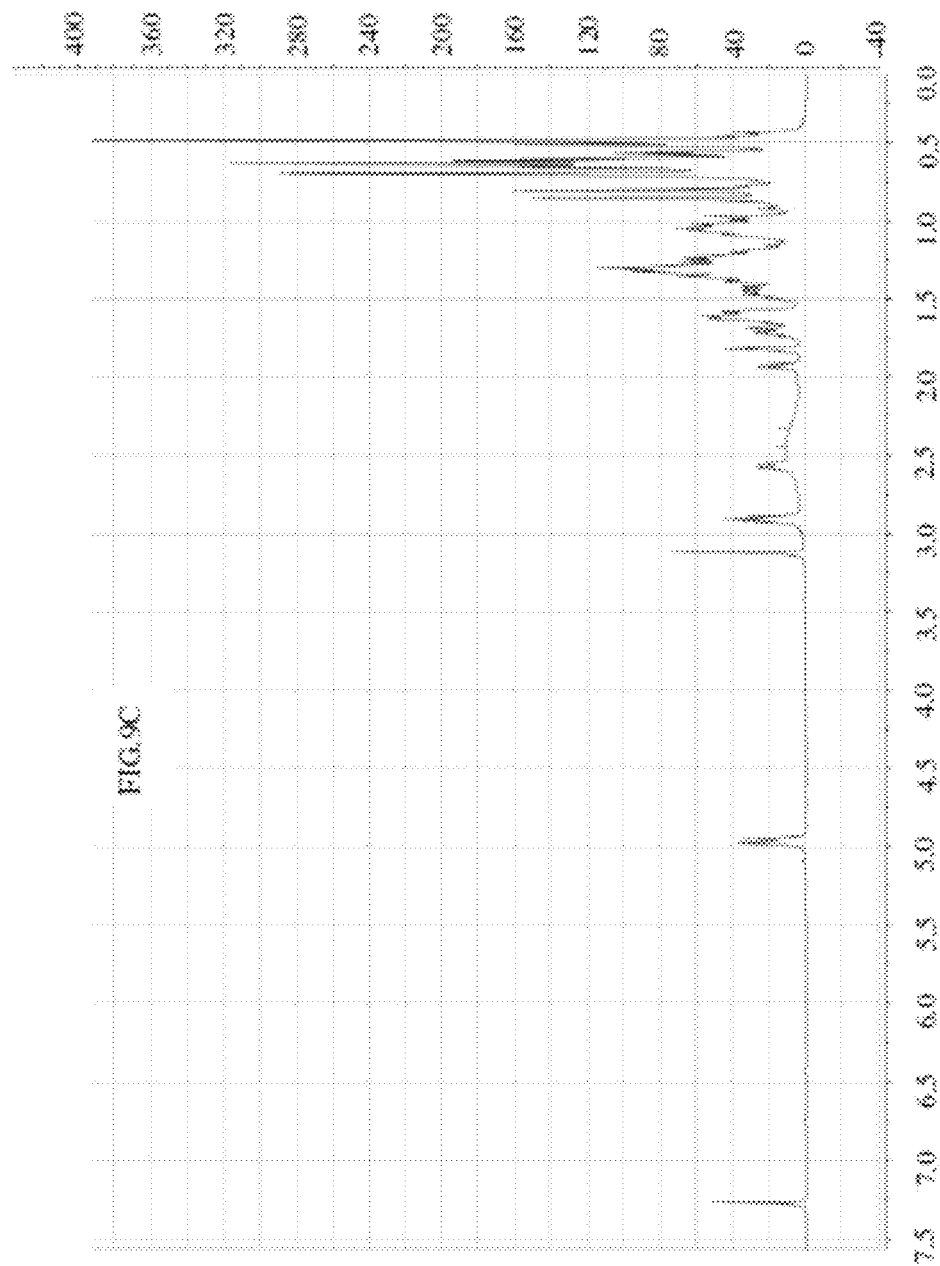
Figure 9D:
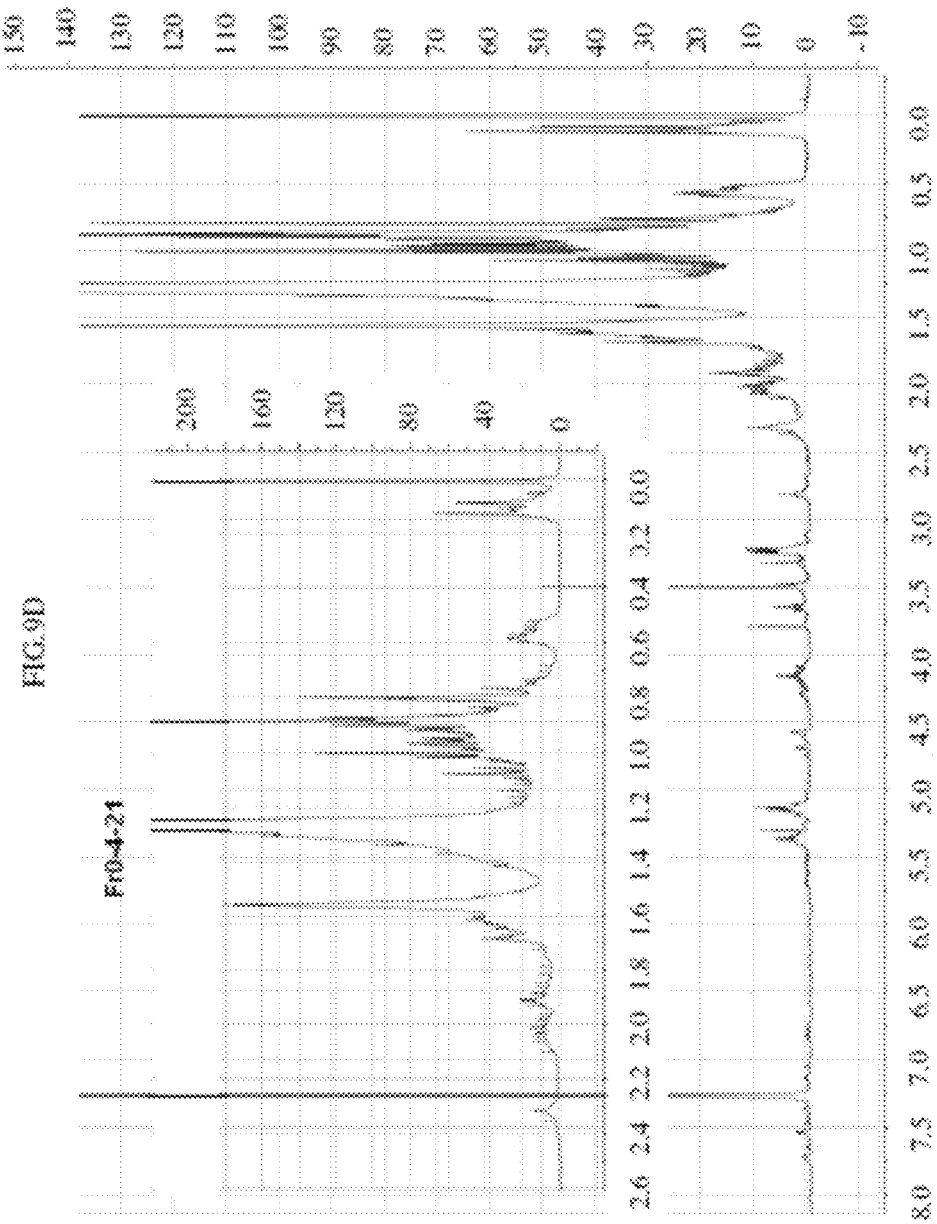
Figure 9B:
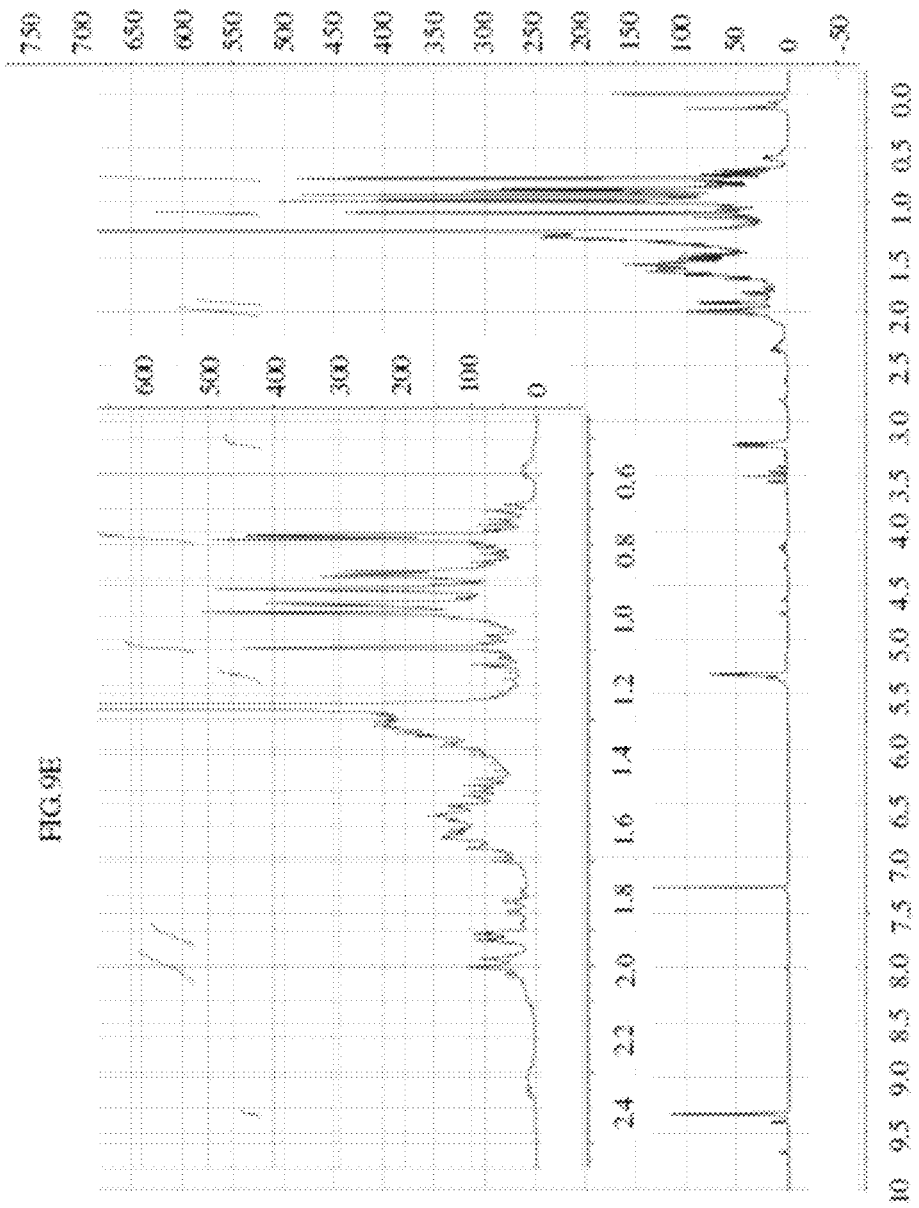
Figure 9F:
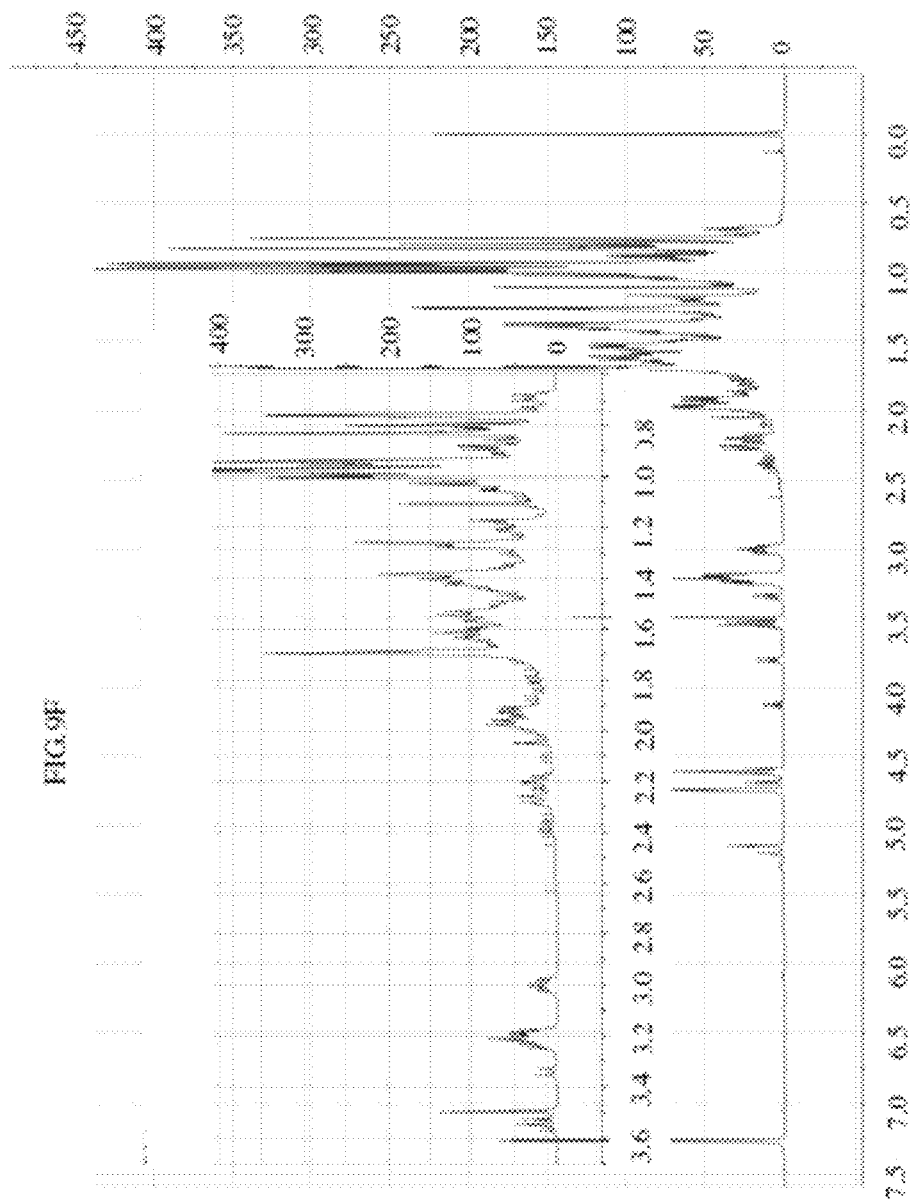
Figure 9G:
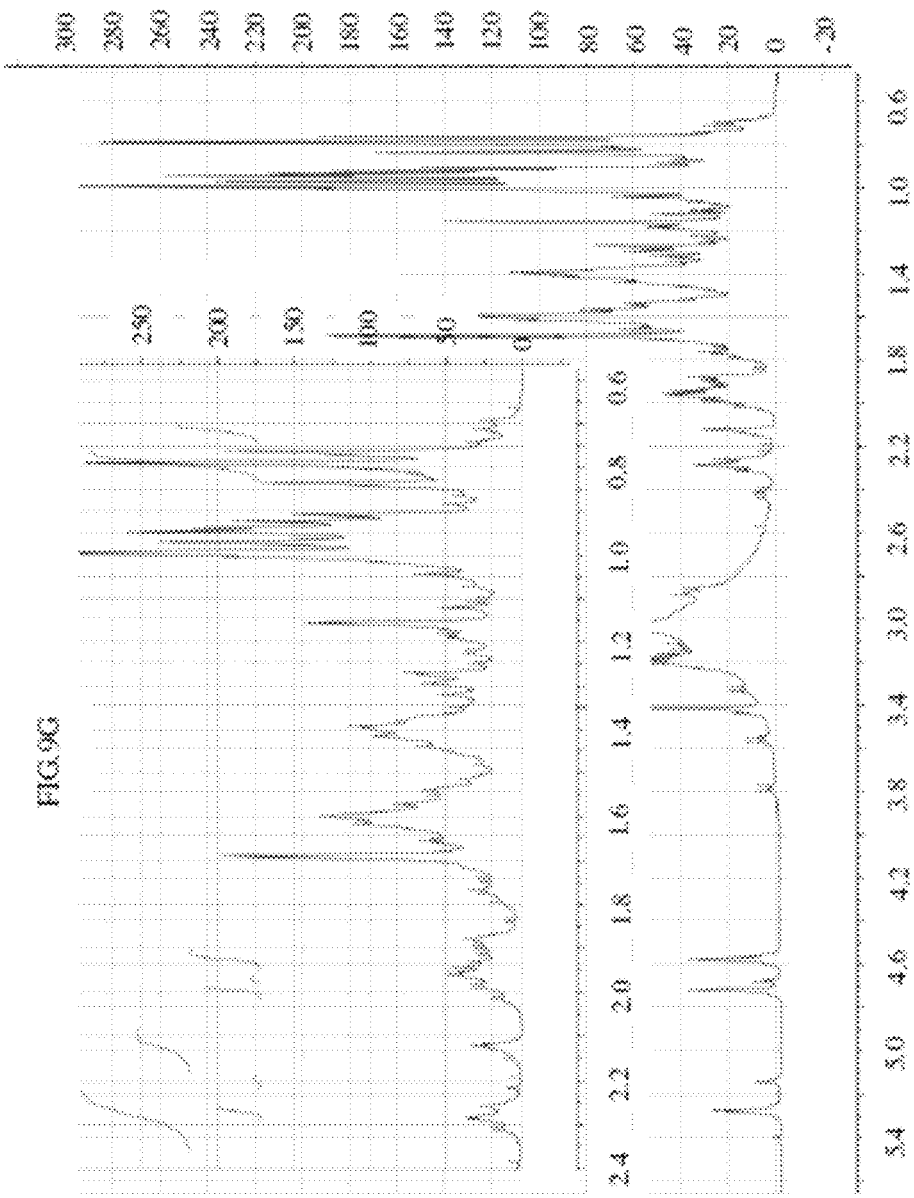
Figure 3H:
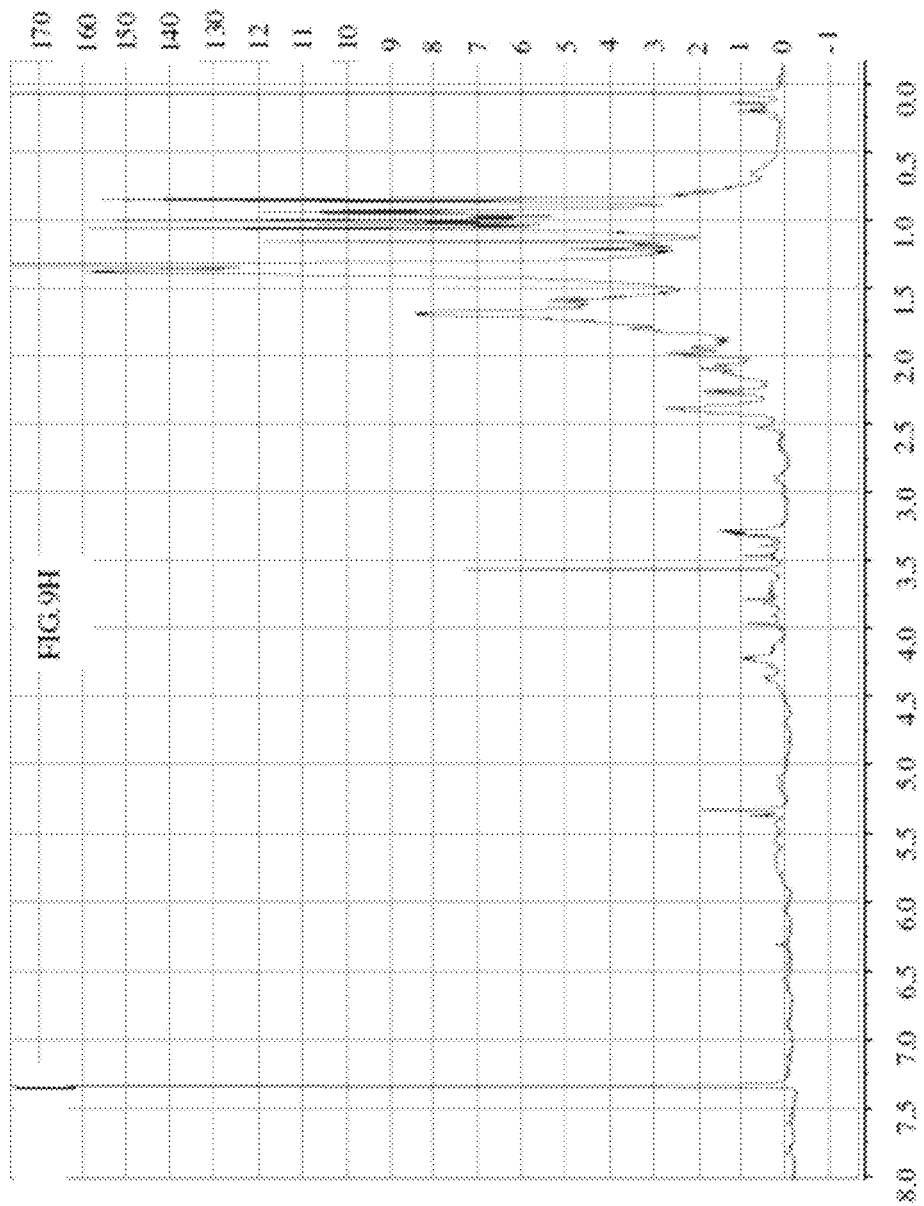

The $^1$HNMR of triterpene is characterized by 7 methyl signals at upfield, an olefinic proton at ca. 5.3 ppm, and an oxygenated methine signal at ca 3.4 ppm along with many methylene and methine proton signals at upfield (ca. 1.0~2.5 ppm). The $^1$HNMR spectra (FIGS. 9B-9I) indicated the major components as steroids and triterpenes. No signals for significant quantity of glycosides were observed. No signals for α,β-unsaturated γ- or δ-lactones, which are characteristic for cardiac glycosides, were observed, suggesting that there is no cardiac glycoside or its aglycone existing in the Fr-0-4 fraction. The $^1$HNMR spectrum in FIG. 9C corresponds to a sub-fraction comprising at least one steroid and at least one or at least two different triterpenes. The $^1$HNMR spectrum in FIG. 9B corresponds to a sub-fraction comprising at least two different tripenes, such as a mixture of two ursanes, and excluding a steroid. The individual triterpenes were isolated and identified as oleanolic acid, ursolic acid and betulinic acid by additional $^1$HNMR and HPLC analyses.

Accordingly, the Fraction 0-4 comprises at least one triterpene and optionally at least one steroid. In some embodiments, the Fraction 0-4 comprises at least two triterpenes, at least three triterpenes, or the fraction comprises plural triterpenes. The Fraction 0-4 evaluated in this example excludes a therapeutically effective amount of cardiac glycoside. In some embodiments, the Fraction 0-4 excludes a cardiac glycoside. In some embodiments, a first sub-fraction of the Fraction 0-4 comprises at least one steroid and at least one triterpene or at least two different triterpenes, a second sub-fraction comprises at least two triterpenes and excludes a steroid. In some embodiments, each of the first and second sub-fractions excludes cardiac glycoside.

In some embodiments, the Fraction 0-4 comprises at least the three triterpenes oleanolic acid, ursolic acid and betulinic acid and excludes oleandrin, excludes neriifolin, excludes steroid, and excludes pharmacologically active polysaccharide obtained from Nerium species or Thevetia species. The molar ratio of oleanolic acid to ursolic acid to betulinic acid in the fraction can be as described for the neuroprotective compositions herein.

Figure 10:
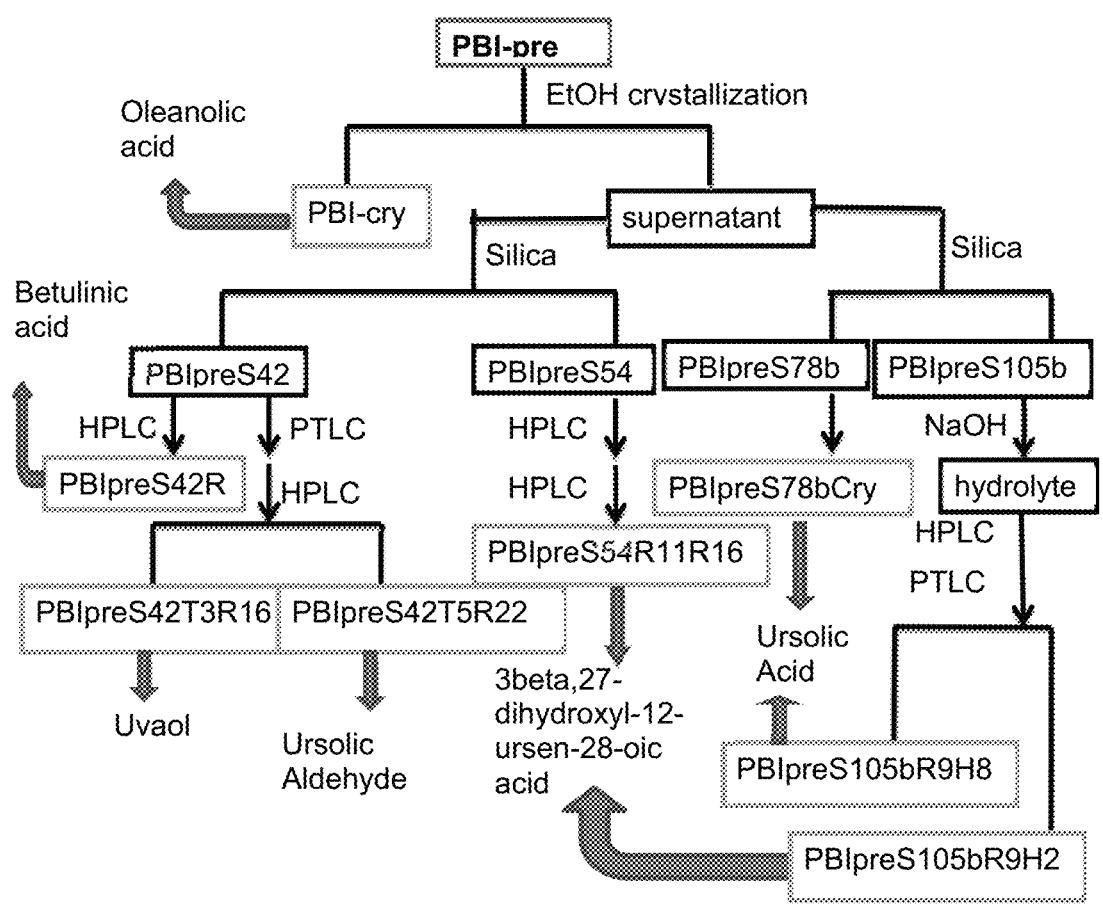
FIG. 10 depicts a schematic detailing various fractionation steps performed on the Fraction 0-4 to isolate components present therein according to Example 20.

Sub-fractionation of the Fraction 0-4 can be achieved by a combination of various precipitation, solvent extraction and chromatographic steps according to the scheme in FIG. 10, the details of which are set forth in Example 20. Alternatively, a synthetic mixture of the three triterpenes in Fraction 0-4 present in the molar ratios described herein can be used as the neuroprotective composition.

The Fraction 0-4 was tested in OGD treated brain slices (stroke model) and non-OGD treated (i.e. control) brain slices (non-stroke model). The data indicate that the Fraction 0-4 provides substantial neuroprotection when using solutions of Fraction 0-4 ranging in concentration from 100 ng/mL to 1 μg/ml and provides even greater neuroprotection when using solutions of Fraction 0-4 ranging in concentration from 1 μg/mL to 1 mg/mL. Accordingly, a liquid dosage form containing 100 ng/mL to 1 mg/mL of a fraction of extract per mL of liquid dosage form should provide neuroprotection in a subject to which it is administered.

While no direct measurements have been made in human brain following a systemic dose of the extract, it is assumed that one or more pharmacologically active components in the neuroprotective composition will cross the blood brain barrier when administered to a subject.

Accordingly, the invention provides a method of protecting neurons against loss of activity caused by oxygen depletion or oxygen-glucose depletion by exposing the oxygen depleted and/or glucose-depleted neurons to an effective amount of neuroprotective composition to minimize loss of activity, reduce the rate of loss of activity, stop the loss of activity, slow down onset of loss of activity, and/or protect the function of neurons caused by exposing the oxygen depleted and/or glucose-depleted conditions. In some embodiments, the method employs an effective amount of a fraction or sub-fraction of Nerium species extract or Thevetia species extract.

In some embodiments, the fraction or sub-fraction of extract has been prepared by liquid chromatography fractionation of the extract. In some embodiments, the fraction or sub-fraction has been prepared by precipitation, solvent extraction, liquid chromatography or a combination thereof. Precipitation can be achieved by exposing the extract, or fraction thereof, to an organic liquid (optionally aqueous organic), whereby a portion of the extract precipitates to form a solid fraction (or solid sub-fraction) and a portion of the extract is dissolved in the liquid to form a dissolved fraction (or dissolved sub-fraction). Solvent extraction can be achieved by dissolving the extract (or fraction) in a solvent and adding another liquid that is only partially miscible or is immiscible with the solvent. After mixing, the solute-containing solvent layer is separated from the solute-containing other liquid layer. Removal of the solvent results in a fraction (or sub-fraction) of the extract, and removal of the other liquid results in another fraction (or sub-fraction) of the extract.

In some embodiments, the neuroprotective composition of the invention (which may or may not be a fraction of extract) comprises at least two triterpenes as the pharmacologically active agents. For example, the invention provides a neuroprotective composition comprising a combination of at least ursolic acid and oleanolic acid, a combination of at least betulinic acid and oleanolic acid. In some embodiments, the neuroprotective composition comprises at least three triterpenes as the pharmacologically active agents. In some embodiments, the neuroprotective composition comprises oleanolic acid, ursolic acid and at least one other triterpene as the pharmacologically active agents. For example, the neuroprotective composition can further comprise betulinic acid or at least one other triterpene. The neuroprotective composition can further comprise one or more other pharmacologically active components ingredients extracted from *Nerium* species or *Thevetia* species. The neuroprotective composition consists essentially of at least oleanolic acid and ursolic acid and optionally further comprises betulinic acid, wherein the molar ratio of the triterpenes is as described herein.

In some embodiments, the neuroprotective composition comprises (consists essentially of) oleanolic acid, ursolic acid, and betulinic acid as the pharmacologically active agents. In some embodiments, the composition comprises oleanolic acid, ursolic acid, betulinic acid and at least one other therapeutically effective agent extracted from *Nerium* species or *Thevetia* species.

In some embodiments, the fraction, or neuroprotective composition, excludes a cardiac glycoside, e.g. oleandrin, odoroside, neritaloside, neriifolin, or those described herein.

Figure 2A:
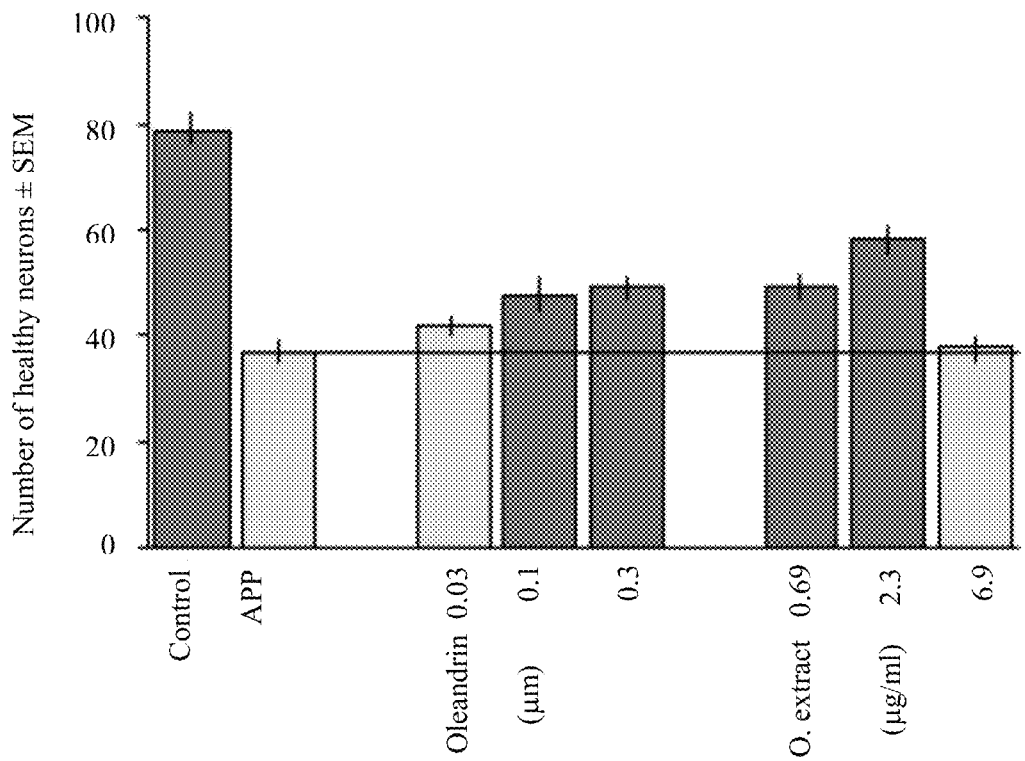
FIGS. 2A-2C depict results of the comparative evaluation of oleandrin versus the unfractionated SCF extract of Nerium oleander in a neuroprotection brain-slice-based "Alzheimer's" assay (Example 9), wherein the number of healthy cortical neurons is determined following APP/Aβ-induced degeneration in the absence or presence of varying amount of those agents.
Figure 2B:
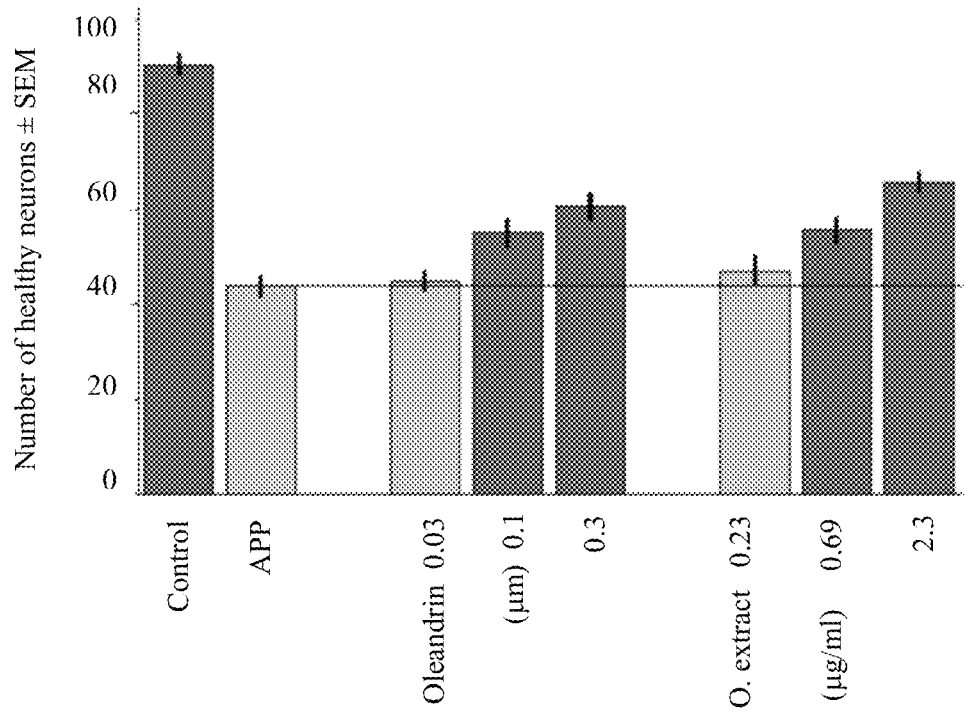
Figure 2C:
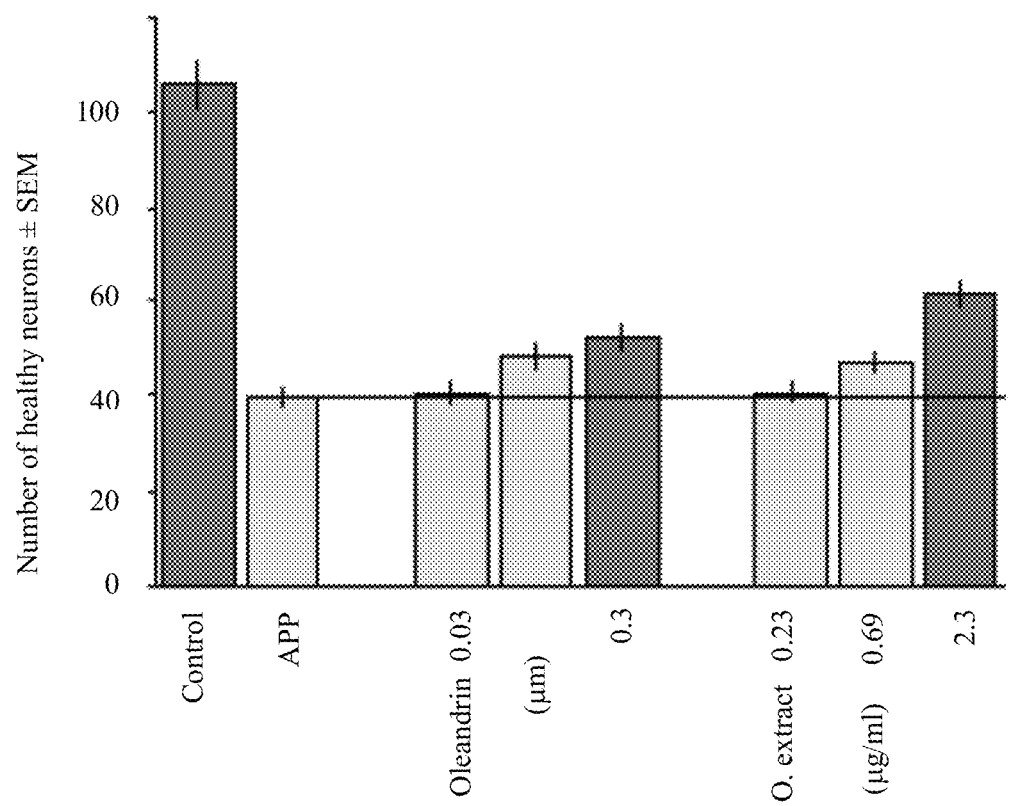
Figure 3A:
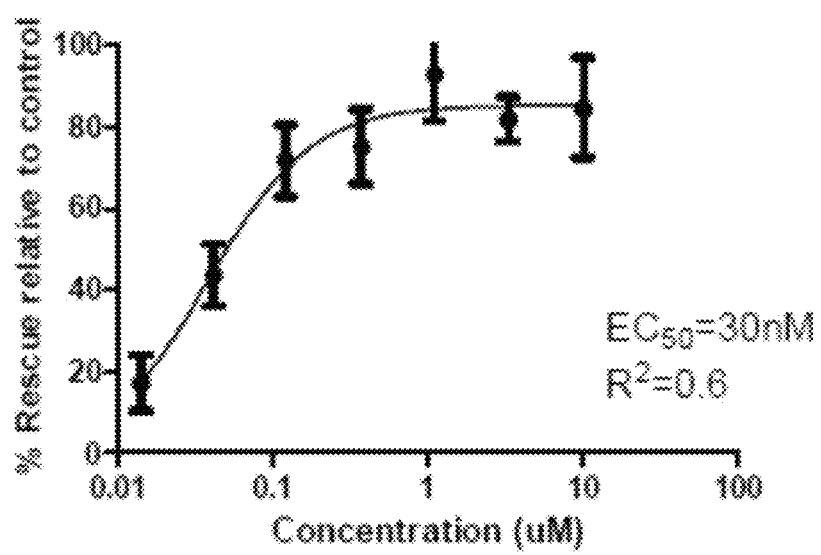
FIGS. 3A-3D depict results from duplicate experiments of the comparative evaluation of oleandrin in a neuroprotection cortico-striatal co-culture neuron-based "Huntington's disease" assay (Example 10), wherein the percent rescue, relative to control, of cortical neurons versus striatal neurons transfected with a mutant form of the Huntington (htt) protein is determined in the absence or presence of varying amounts of oleandrin.
Figure 3B:
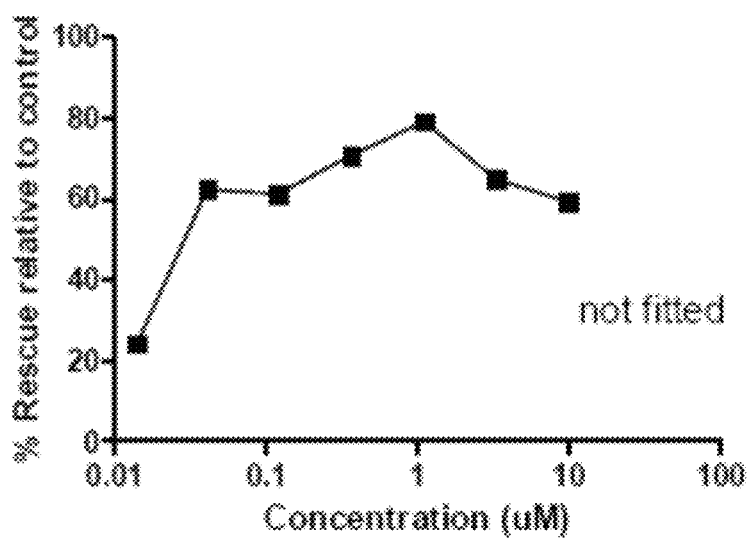

Example 9 provides a detailed description of an in vitro assay used to evaluate the efficacy of the extract for the treatment of Alzheimer's disease. The assay is a brain slice-based assay for APP/Aβ-induced (APP: amyloid precursor protein) degeneration of cortical pyramidal neurons. Upon cleavage by a secretase enzyme, the APP is reduced to Aβ peptides which are believed to be a causative factor in beta-amyloid plaque formation. Aβ proteins are associated with beta-amyloid plaque formation and are believed to be a hallmark if not etiologic factor in Alzheimer's disease. Biolistic transfection is used to introduce vital markers such as YFP (a marker yellow fluorescent protein) and to introduce disease gene constructs into the same neuronal populations in the brain slices. YFP is co-transfected with APP isoforms leading to the progressive degeneration of cortical pyramidal neurons over the course of three to four days after brain slice preparation and transfection. The data (FIGS. 2A-2C) indicate that the *Nerium* species SCF extract provided a concentration-dependent neuroprotection to APP-transfected brain slices thereby rescuing levels nearly to the same levels as provided by BACE inhibitor drugs, i.e. beta secretase inhibitor drugs. The beta secretase enzyme cleaves the APP precursor protein into toxic Aβ-proteins. The oleandrin-containing SCF extract appeared to provide greater neuroprotection than oleandrin alone. The data in FIGS. 2A-2C are of significance in that few compounds or therapeutic strategies in the literature have shown any significant protection of neurons in this in vitro assay representative of Alzheimer disease.

Fraction 0-4 also provides strong neuroprotection in two additional brain slice models in which cortical neuronal degeneration is driven by biolistic transfection of expression constructs for genes implicated in CNS neurodegeneration, namely, amyloid precursor protein (APP) and tau. In these models, APP and tau transfection induces progressive neurodegeneration of cortical neurons over the course of 3-4 days, in contrast to the neuronal injury and death caused by OGD which occurs over a 24 h period in the brain slice model.

Figure 6:
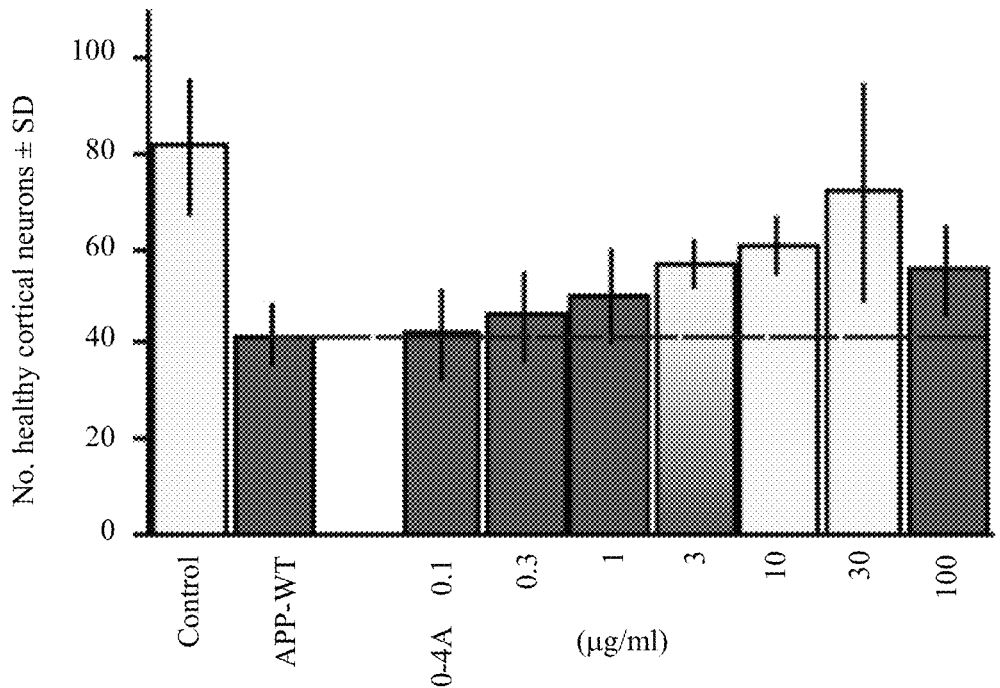
FIG. 6 depicts the results of the comparative evaluation of a fraction (0-4 or 0-4A) of Nerium oleander SCF extract versus untreated (cells were not transfected with APP/Aβ) in an APP-based "Alzheimer's" assay (Example 11), wherein the number of healthy cortical neurons is determined following APP/Aβ-induced degeneration in the absence or presence of varying amount of those agents.
Figure 12:
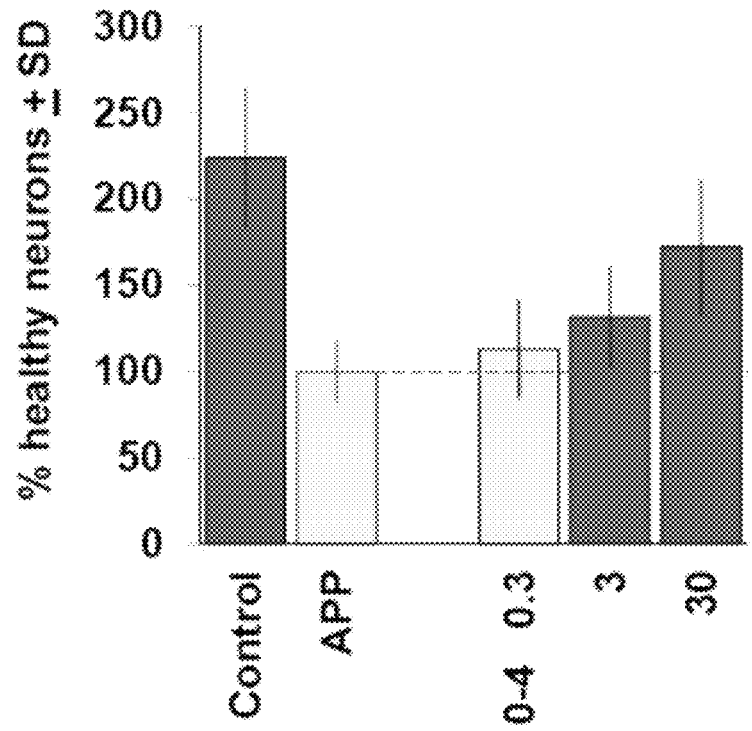
FIG. 12 depicts the results of the evaluation in an APP-based "Alzheimer's" assay of a fraction (0-4 or 0-4A) of Nerium oleander SCF extract, wherein the percent of healthy neurons is determined. Concentration-response relations for Fraction 0-4 in the brain slice APP assay as indicated, in units of µg/ml. Averages of 3 and 4 independent runs are shown for APP with the negative-control conditions (treated with DMSO only) set to 100%. For both graphs, dark bars denote statistically significant differences with respect to the respective APP or Tau4R negative-controls using ANOVA followed by Dunnett's post hoc comparison test at the 0.05 confidence level.

The APP-WT brain slice-based Alzheimer's assay was repeated (Example 11) using fractions of the SCF extract of *Nerium oleander*. The number of healthy cortical neurons was determined following APP/Aβ-induced degeneration in the presence of varying amounts of fraction 0-4A of the SCF extract (0.01 to 100 µg/ml). Exposure to oxygen and glucose deprivation served as the internal positive control producing the stroke-like mediated injury to neurons. The negative control was simply the relative health of the brain slice neurons without OGD treatment or exposure to treatments. The data is depicted in FIG. 6 and FIG. 12, wherein the lighter colored bars indicate a significant difference with respect to the APP-WT condition by ANOVA followed by Dunnett's post hoc comparison test at the 0.05 confidence level.

The data indicate that the Fraction 0-4A (or 0-4, PBI-04711) provides neuroprotection in this assay, even though it does not contain any cardiac glycosides. Fraction 0-4 provided significant concentration-dependent neuroprotection in both the APP and tau brain slice neurodegeneration models, albeit in a somewhat higher concentration range compared to that observed for OGD. As Fraction 0-4 was provided only as a single-bolus administration at the beginning of these longer-term assays, the apparent right-shift in concentration-response could have been due to compound turnover in the intact brain tissue environment of these assays.

Figure 7:
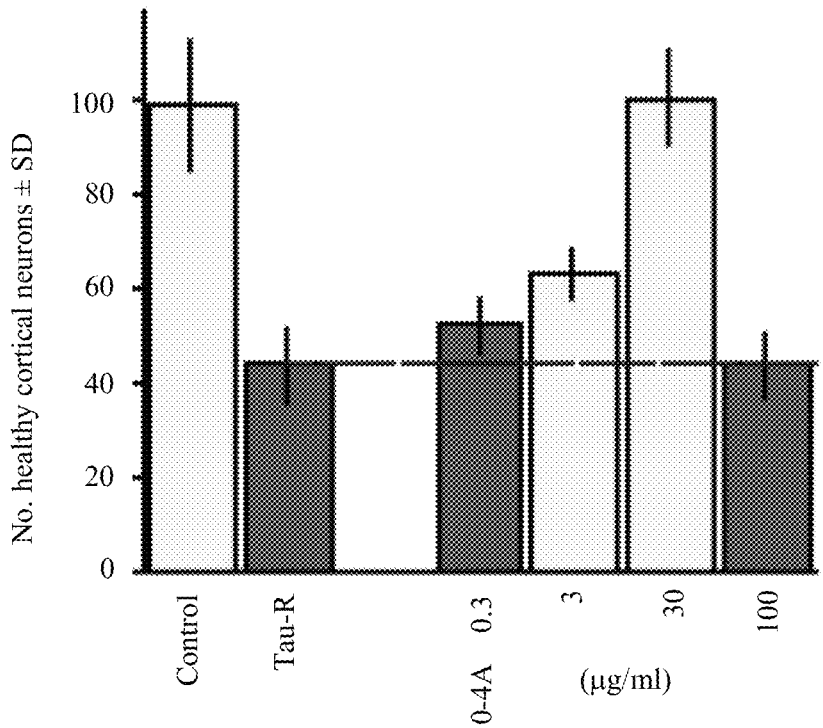
FIG. 7 depicts the results of the comparative evaluation of a fraction (0-4 or 0-4A) of Nerium oleander SCF extract versus untreated (cells were not transfected with APP/Aβ) in a Tau4R based "Alzheimer's" assay (Example 12), wherein the number of healthy and damaged cortical neurons are determined following Tau4R in the absence or presence of varying amounts of those agents.
Figure 8A:
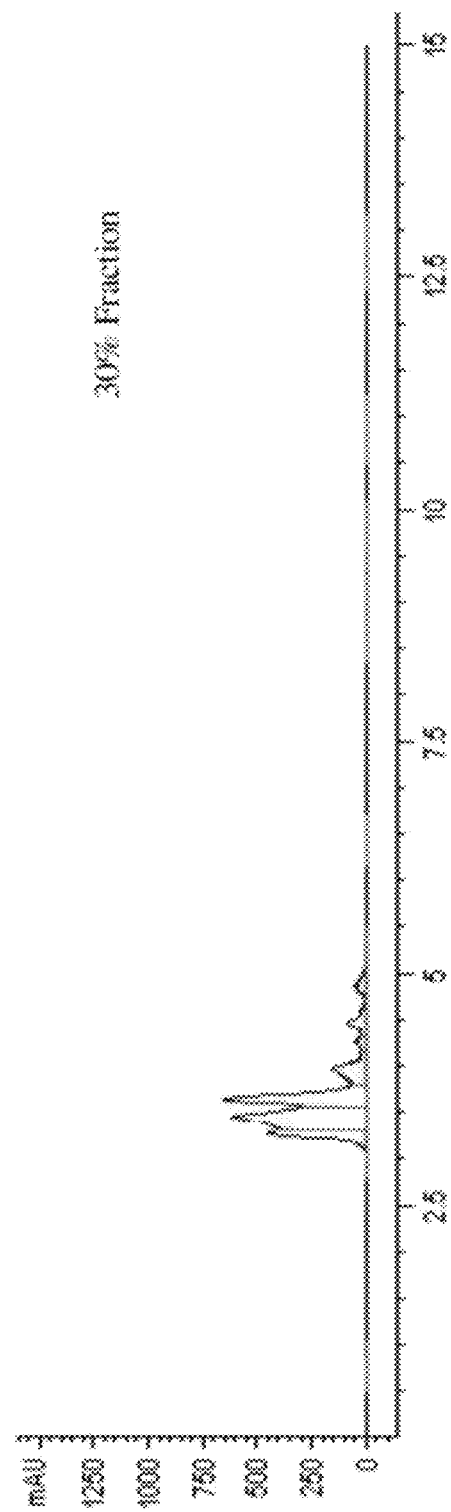
FIGS. 8A-8D depict the chromatograms obtained by HPLC analysis of the fractions prepared according to Example 13.
Figure 8B:
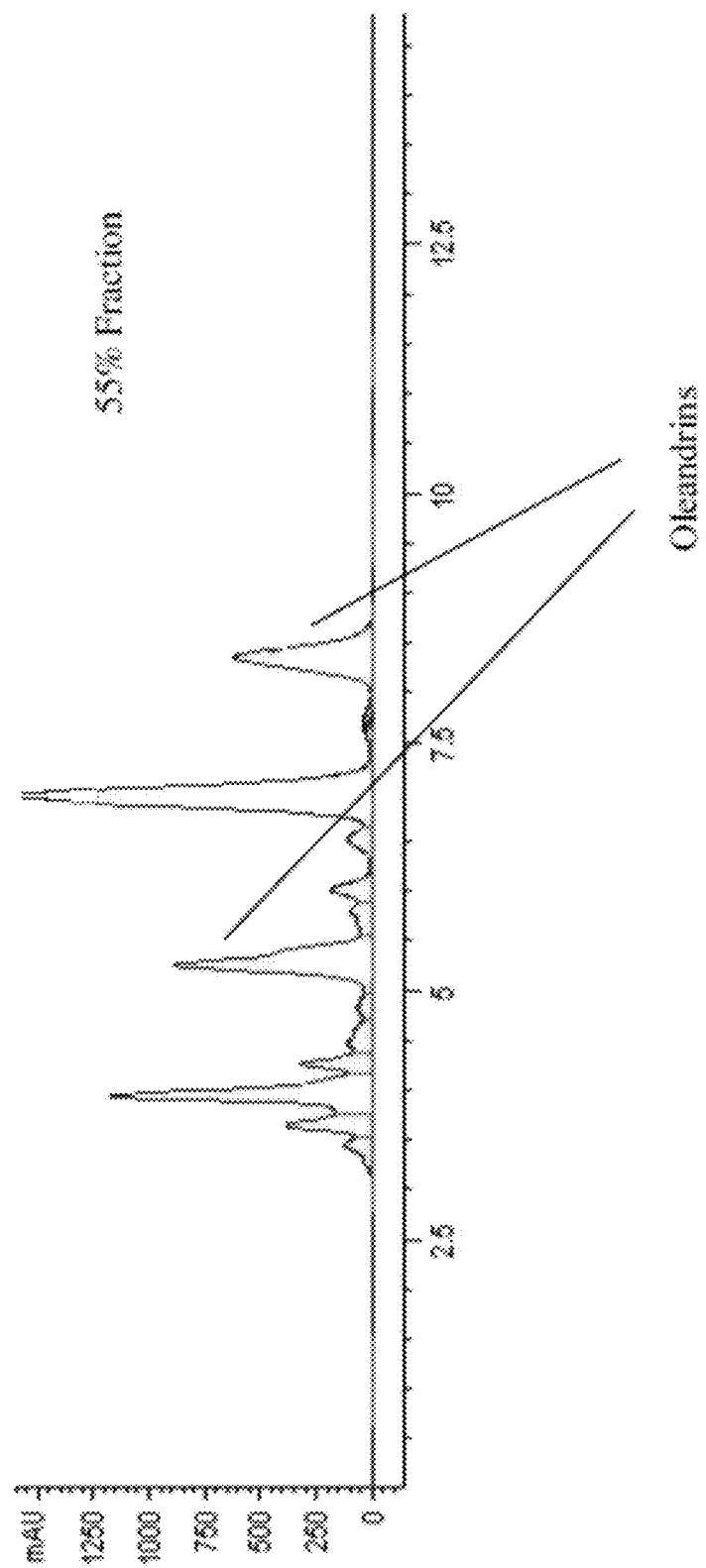
Figure 8C:
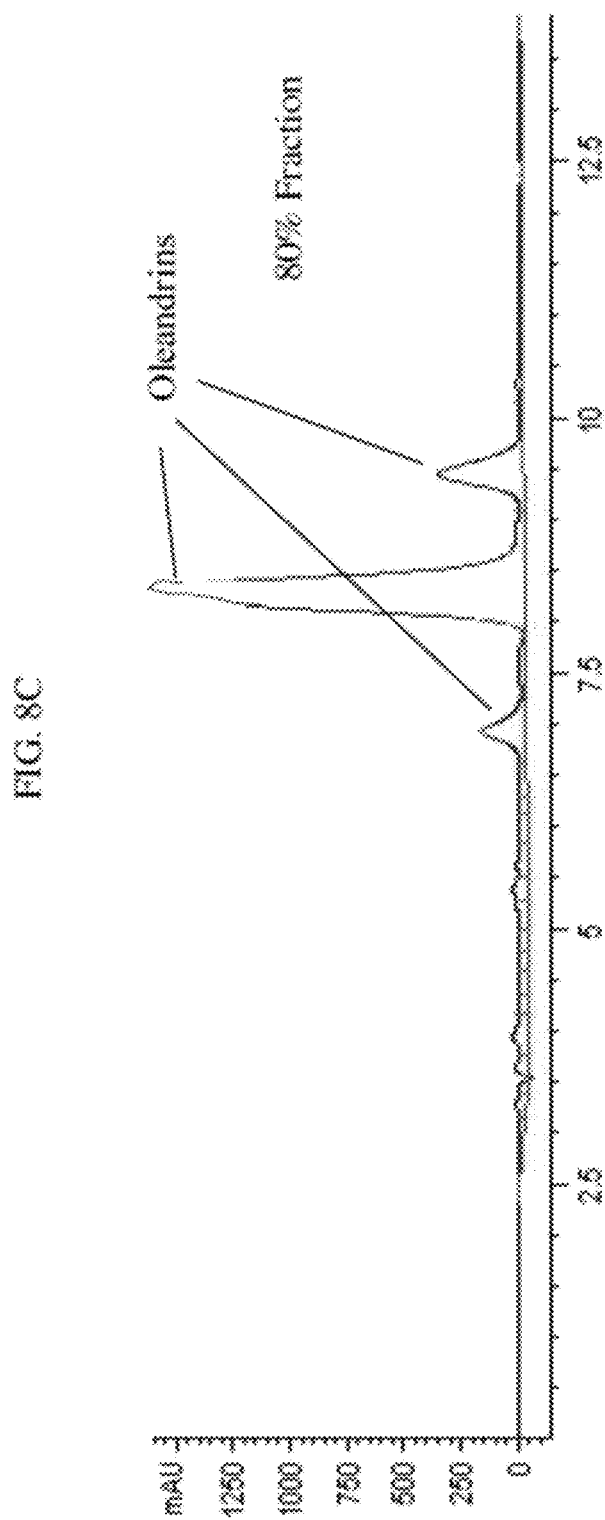
Figure 8D:
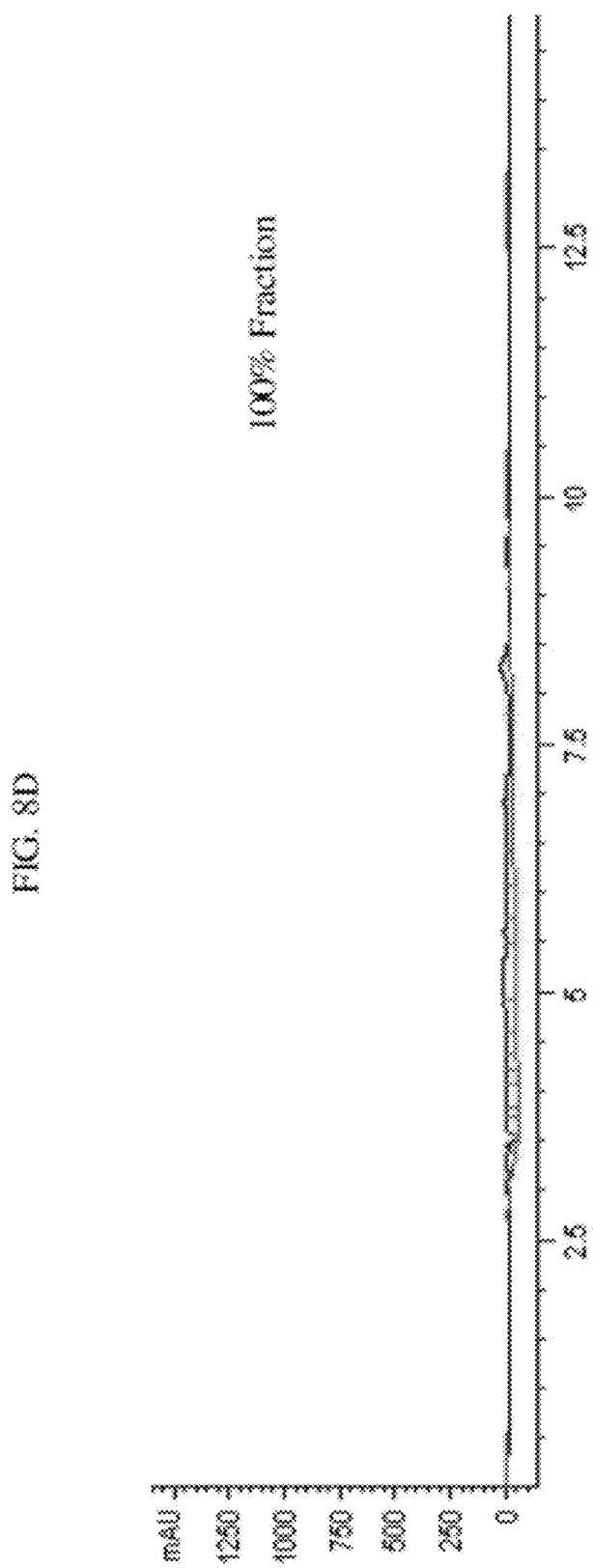
Figure 6A:
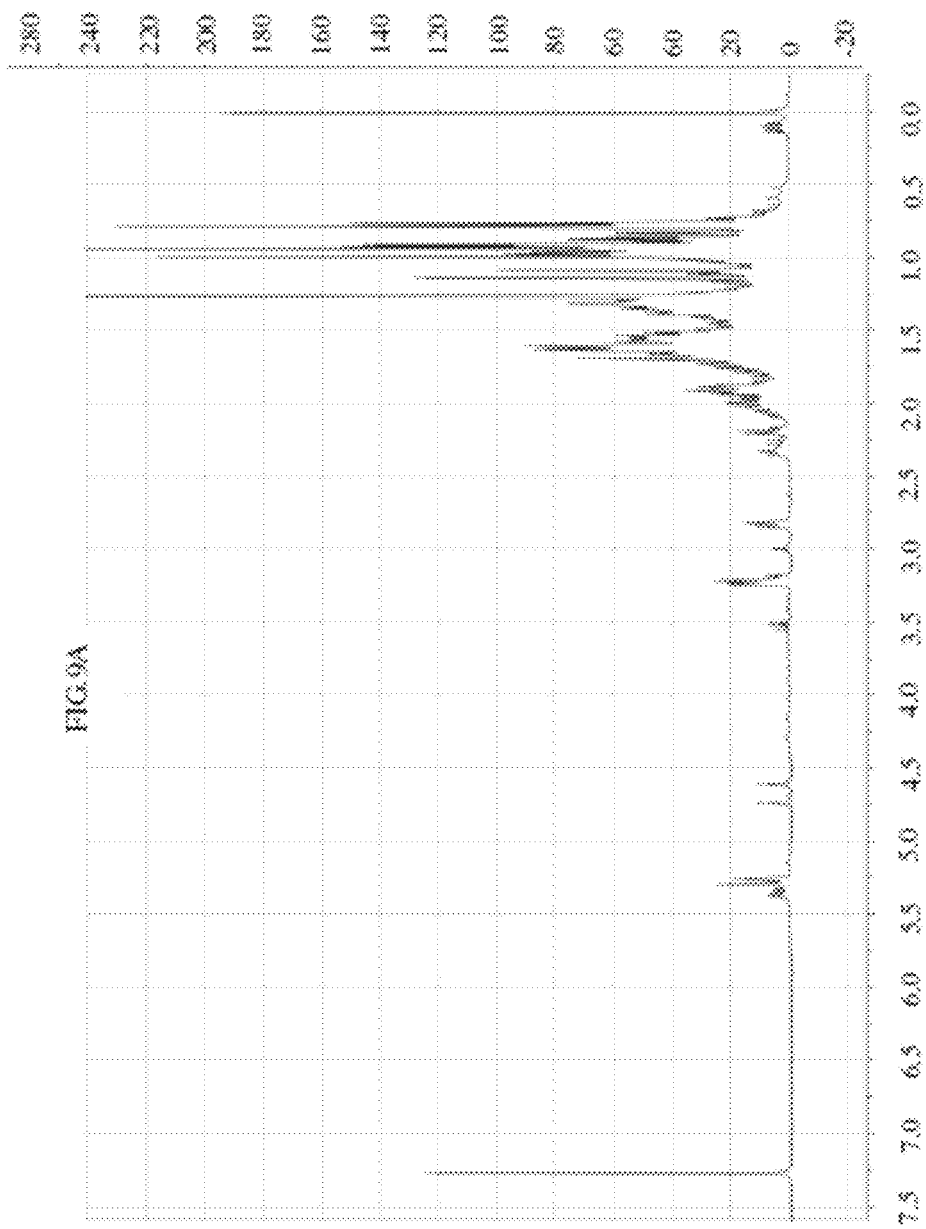
Figure 13:
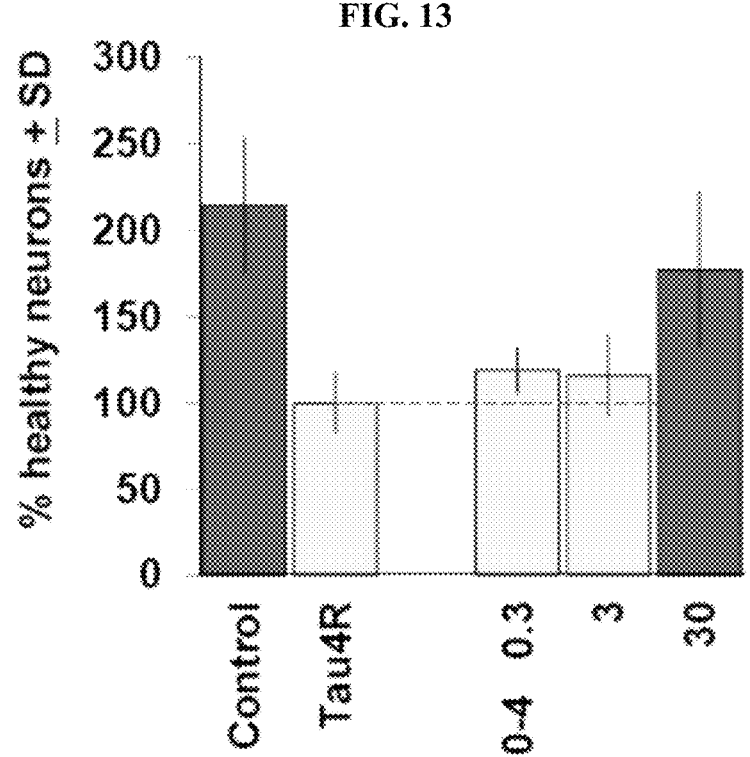
FIG. 13 depicts the results of the evaluation in a Tau4R-based "Alzheimer's" assay of a Fraction (0-4 or 0-4A) of Nerium oleander SCF extract, wherein the percent of healthy neurons is determined. Concentration-response relations for Fraction 0-4 in the brain slice tau4R assay as indicated, in units of µg/ml. Averages of 3 and 4 independent runs are shown for tau4R with the negative-control conditions (treated with DMSO only) set to 100%. For both graphs, dark green bars denote statistically significant differences with respect to the respective Tau4R negative-controls using ANOVA followed by Dunnett's post hoc comparison test at the 0.05 confidence level.

Fraction 0-4 (0-4A) of the SCF extract of *Thevetia oleander* was evaluated with the tau4R brain slice-based Alzheimer's assay (Example 12). The number of healthy cortical neurons is determined. Efficacy in this assay is defined as or based upon the relative total number of healthy versus unhealthy number and percentage of degraded neurons in the presence of varying amounts of fraction 0-4A of the SCF extract (0.3 to 100 µg/ml, the concentration having been determined by weight of the extract). The negative control in these experiments consisted of brain slices that were not exposed to OGD while brain slices exposed to OGD but not treated with fractions derived from unfractionated *Nerium oleander* extract served as the internal positive control. The data is depicted in FIG. 7 and FIG. 13, wherein the lighter colored bars indicate a significant difference with respect to damaged neurons by ANOVA followed by Dunnett's post hoc comparison test at the 0.05 confidence level. The data indicate that the Fraction 0-4A provides neuroprotection in this assay, even though it does not contain cardiac glycoside.

As discussed above, Bardoxolone has been extensively investigated in clinical trials in inflammatory conditions; however, a Phase 3 clinical trial in chronic kidney disease was terminated due to adverse events that may have been related to known cellular toxicities of certain triterpenoids including bardoxolone at elevated concentrations. Surprisingly, Fraction 0-4 (which comprises OA, UA and BA and excludes cardiac glycoside) and oleanolic acid have not exhibited observable cellular toxicity in our hands and provide robust neuroprotection in the brain slice OGD model.

Figure 14A:
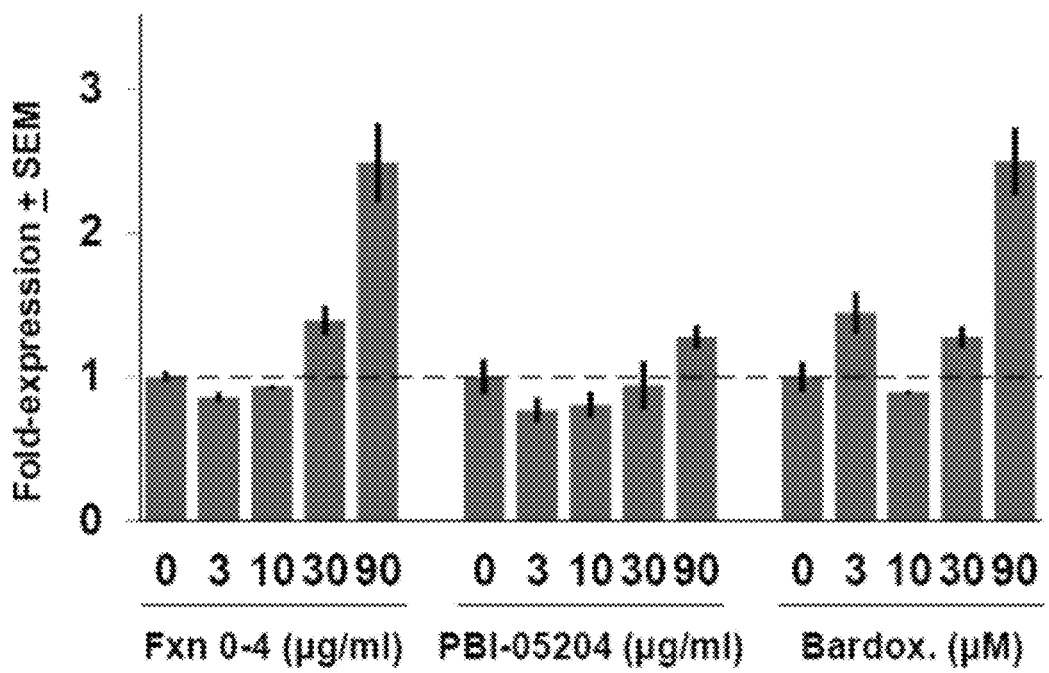
FIGS. 14A and 14B depict the results of the comparative evaluation, in a Nrf2/ARE expression assay (Example 22), for Fraction 0-4 and the SCF extract (PBI-05204) versus the reference compound bardoxolone (which does not exhibit sufficient blood-brain barrier penetration): 7 hours after treatment (FIG. 14A) and 24 hours after treatment (FIG. 14B). Concentration- and time-dependent induction of a 5×-ARE-luciferase transcriptional reporter by Fraction 0-4, PBI-05204, and bardoxolone in mouse primary corticostriatal neuronal co-cultures. Activation of the 5×-ARE luciferase reporter became stronger with an apparent left-shift in concentration-response for extended treatment over 24 h compared to 7 h. Fold-expression changes are expressed relative to the DMSO-carrier only condition ("0") normalized to a co-transfected, constitutive Renilla luciferase control and set to a value of 1.
Figure 14B:
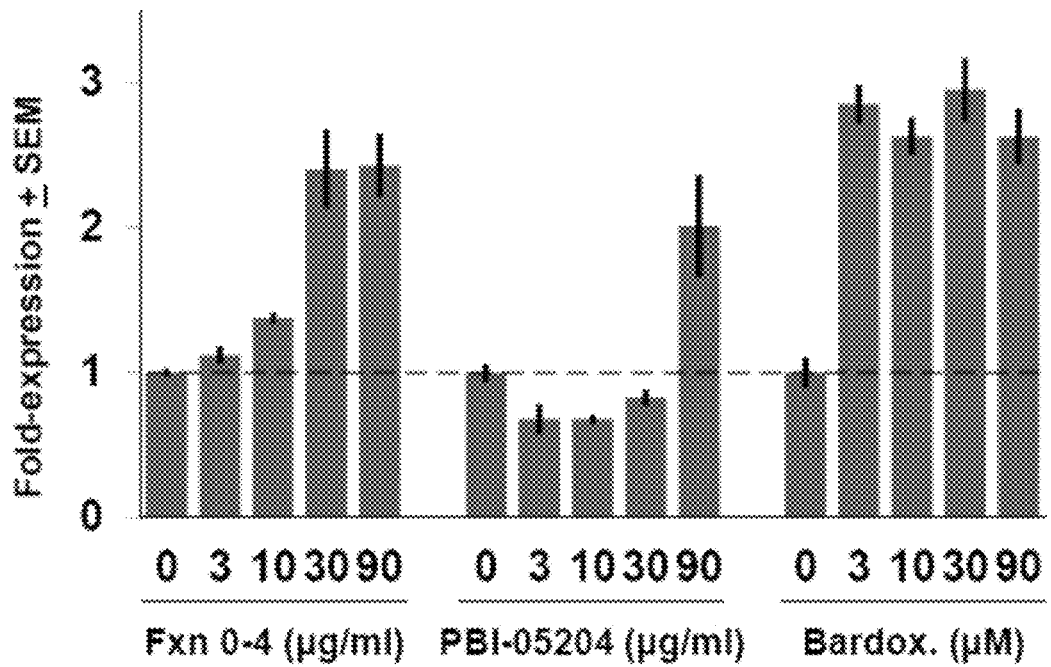
Figure 15C:
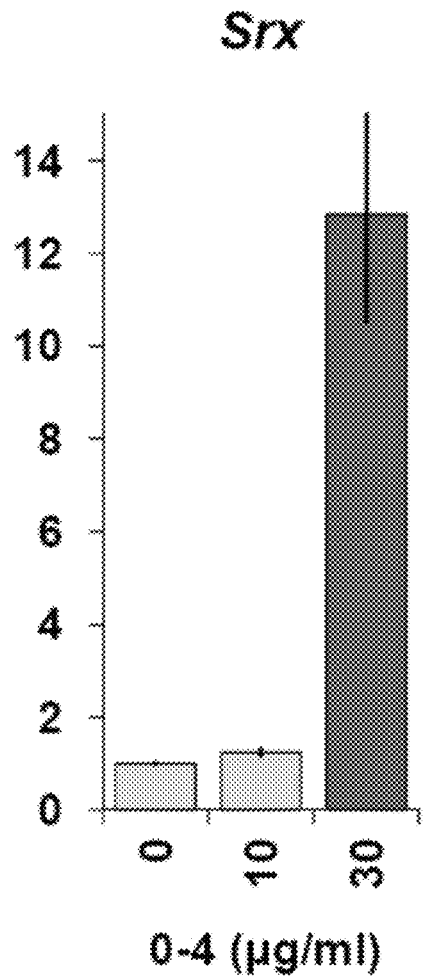
Figure 15D:
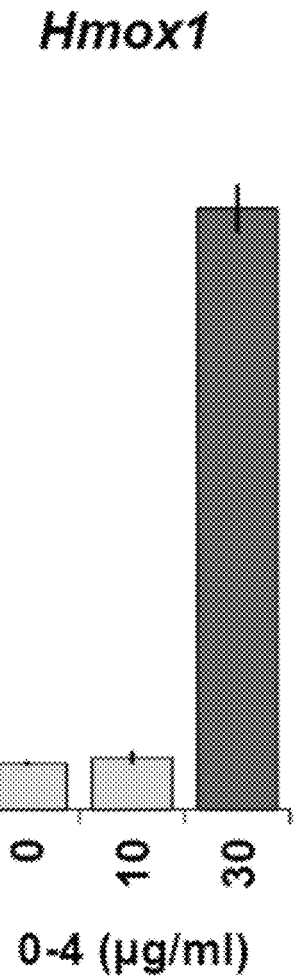

Fraction 0-4 and oleanolic acid are shown herein to activate the Nrf2-ARE gene pathway in neurons, using a corticostriatal primary neuronal co-culture system composed of the same neuronal and glial cell types represented in the brain slice assays. An ARE-luciferase promoter-reporter construct which has been used extensively as an assay for Nrf2 activation was introduced into neuronal co-cultures. As can be seen in the figures, e.g. FIGS. 14A and 14B, treatment with Fraction 0-4 led to clear, concentration- and time-dependent increases in activation of the ARE-luciferase reporter, and to levels similar to that induced by the reference triterpenoid bardoxolone. By 24 h of treatment, significant induction of the ARE-luciferase reporter was seen in similar concentration ranges that provided neuroprotection in the OGD, APP, and tau brain slice neuroprotection assays. The unfractionated PBI-05204 extract increased ARE-luciferase transcription only at the highest concentration tested.

Fraction 0-4 also induces expression of other ARE target genes (FIGS. 15A-15D). The four canonical targets of Nrf2 activation assayed (the ARE genes glutamate-cysteine ligase, catalytic subunit (Gclc); NAD(P)H:quinone oxidoreductase 1 (Nqo 1); sulfiredoxin antioxidant protein (Srx); and heme oxygenase 1 (Hmox1)), were all significantly increased by treatment with Fraction 0-4 in a concentration-dependent manner, and to levels comparable to that induced by other known Nrf2 activators such as dimethyl fumarate (DMF; data not shown).

Figure 17:
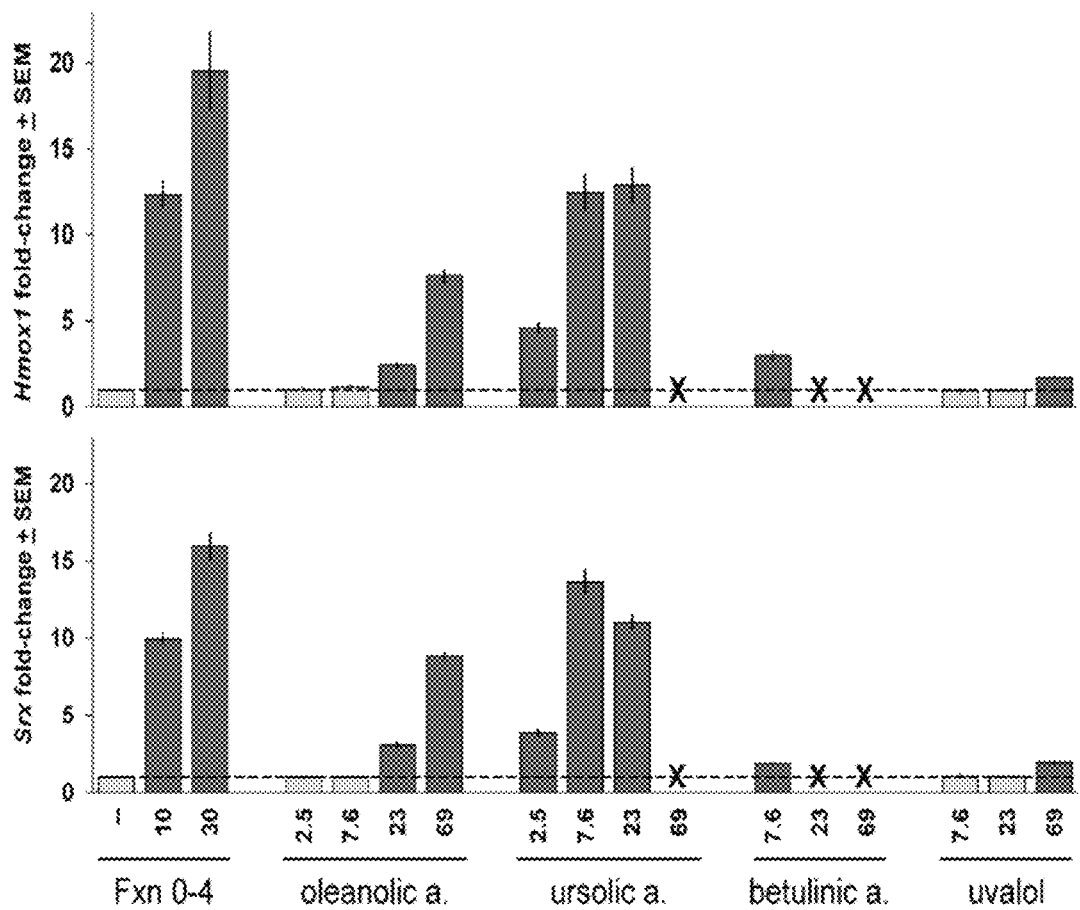
FIG. 17 depicts the results of expression assays for Fraction 0-4 and the individual triterpenes oleanolic acid, ursolic acid, betulinic acid and uvaol. "X" symbols denote concentrations of compounds which induced toxicity and for which recovery of residual mRNA was insufficient to support qPCR analysis. Rat primary corticostriatal co-cultures were treated for 6 h with Fraction 0-4 (in µg/ml) or oleanolic acid, ursolic acid, betulinic acid, or uvalol (all in μM) at the concentrations indicated, then harvested and processed for qPCR analysis of the ARE target genes shown. Quantitative RNA values were normalized to the GAPDH reference control and fold-expression changes are expressed relative to the DMSO-carrier only condition ("--") set to a value of 1. Dark bars denote statistically significant differences with respect to the DMSO-carrier only control by a Student's t-test at $p<0.05$.

The potential additive and synergistic performance of the mixture of triterpenes in Fraction 0-4 was determined by analyzing their performance individually and in different mixtures by way of the expression assay (Example 22, FIG. 17). Oleanolic acid and ursolic acid individually induced robust upregulation of canonical ARE target genes to similar extents compared to Fraction 0-4, and in a strikingly similar pattern, shown here for glutamate-cysteine ligase, modifier subunit (Gclm); Nqo1, Srx, and Hmox1. Betulinic acid was also able to induce ARE gene expression in an intermediate concentration between 7.6 and 23 µg/ml despite its toxicity. By comparison, uvaol was not able to induce ARE gene expression to a notable extent at any concentration tested.

Figure 18:
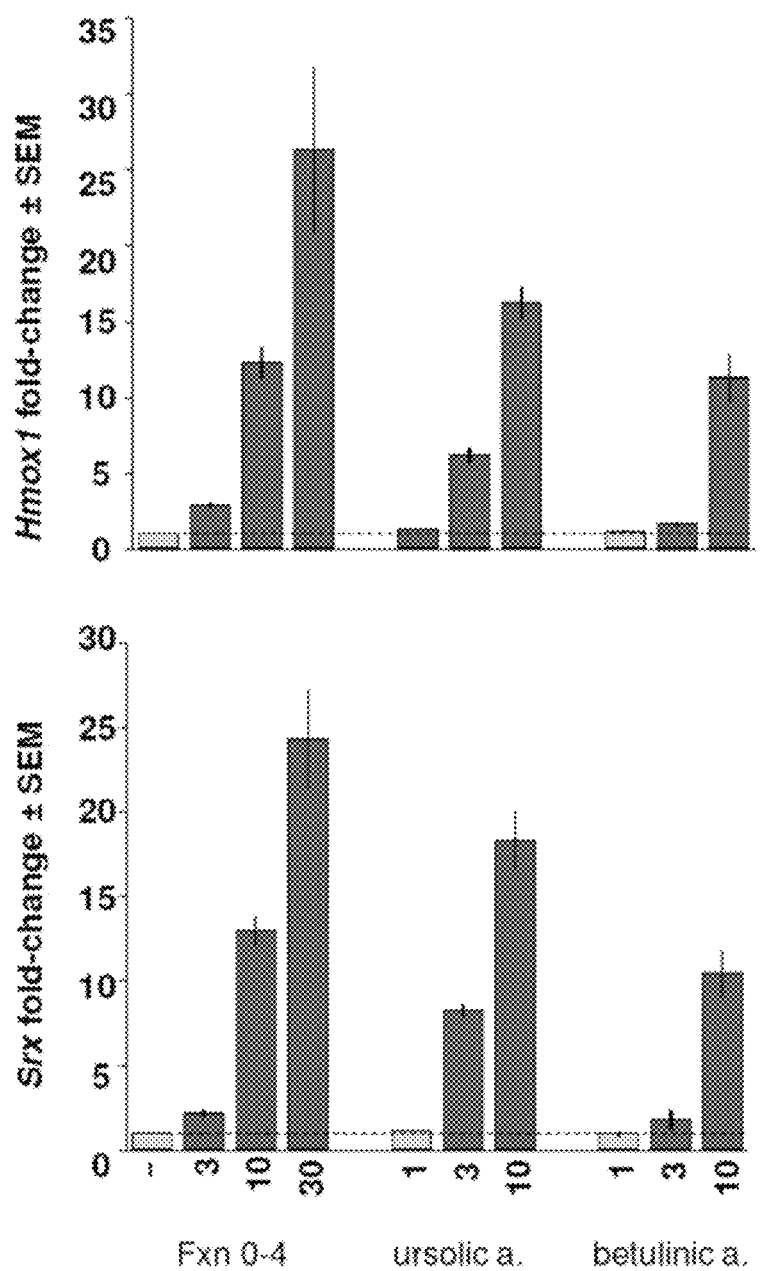
FIG. 18 depicts the results of expression assays for Fraction 0-4 and the individual triterpenes ursolic acid and betulinic acid at more similar concentration ranges. Rat primary corticostriatal co-cultures were treated for 6 h with Fraction 0-4 (in μg/ml) or ursolic acid and betulinic acid (in μM) at the concentrations indicated, then harvested and processed for qPCR analysis of the ARE target genes shown. Quantitative RNA values were normalized to the GAPDH reference control and fold-expression changes are expressed relative to the DMSO-carrier only condition ("--") set to a value of 1. Dark blue bars denote statistically significant differences with respect to the DMSO-carrier only control by a Student's t-test at $p<0.05$.

Activation of the ARE genes by ursolic acid and betulinic acid was examined using more closely-spaced concentration steps. Betulinic acid, like ursolic acid, is able to induce clear upregulation of Srx and Hmox1 despite its toxicity at higher concentrations. The data are depicted in FIG. 18.

Accordingly, the invention provides a method of protecting neurons against loss of activity caused by Alzheimer's disease, the method comprising: exposing the neurons exhibiting characteristics of Alzheimer's disease to an effective amount of neuroprotective composition to minimize loss of activity, reduce the rate of loss of activity, stop the loss of activity, slow down onset of loss of activity, and/or critical functioning of the neurons caused by Alzheimer's disease. In some embodiments, the method employs an effective amount of neuroprotective composition.

Example 10 provides a detailed description of an assay used to evaluate the efficacy of the extract (or fraction thereof) for the treatment of Huntington's disease. Mutant htt protein is introduced via electroporation into high-density, mixed co-cultures of cortical neurons, striatal neurons, and glia. The striatal and cortical neurons are transfected with different color fluorescent proteins thereby facilitating the separate identification of the different types of neurons in the co-culture. The color fluorescent proteins are fluorescent and 'emit' color upon activation with a light source of appropriate wavelength. The data (FIGS. 3A-3D) indicate that oleandrin and the SCF extract of Nerium oleander are more effective than KW6002 (an adenosine 2a receptor antagonist) in terms of providing a greater number of surviving neurons. The data also indicate that the SCF extract is more effective than oleandrin alone, suggesting that the extract further comprises one or more therapeutically effective agents, aside from oleandrin, that can be used to treat Huntington's disease. Such other agents can be used along with or in the absence of oleandrin or other cardiac glycoside. Accordingly, the invention provides a method of protecting neurons against loss of activity caused by Huntington's disease, the method comprising: exposing the neurons exhibiting characteristics of Huntington's disease to an effective amount of neuroprotective composition to minimize loss of activity, reduce the rate of loss of activity, stop the loss of activity, slow down onset of loss of activity, and/or normal function of the neurons caused by Huntington's disease.

Example 16 details an exemplary brain-slice assay that can be used to evaluate the efficacy of neuroprotective composition (e.g. extract or fraction thereof) in the treatment of stroke in a subject following completion of a delay period after the stroke. The brain-slice assay with oxygen glucose deprivation is conducted as described herein; however, rather than treating the brain slices prophylactically with the composition, they were treated with the composition after delay periods of 0, 1, 2, 4, and 6 hours. The data should demonstrate that the composition is effective at providing significant neuroprotection for delay periods of up to 1, up to 2, up to 3, up to 4, up to 5, up to about 6 hours after the stroke.

The examples below detail an exemplary brain-slice assay used as a model to evaluate the efficacy of neuroprotective composition in the treatment of stroke in a subject following completion of a delay period after the stroke. The brain-slice assay with oxygen glucose deprivation was conducted as described herein; however, rather than treating the brain slices prophylactically with neuroprotective composition, they were treated with the cardiac glycoside after delay periods of 0, 1, 2, 4, and 6 hours. The data demonstrates that the neuroprotective composition is effective at providing significant neuroprotection for delay periods of up to 1, up to 2, up to 3, up to 4, up to 5, up to about 6 hours after the stroke.

Accordingly, the invention provides a time-delayed method of treating stroke in a subject by administration of a dose of neuroprotective composition (e.g. extract or fraction thereof of Nerium species or of Thevetia species) to a subject after the subject has suffered a stroke. Within an acceptable delay period after a subject has suffered the stroke, an initial dose of the extract is administered according to an initial dosing regimen. Then, adequacy of the subject's clinical response and/or therapeutic response to treatment with the composition is determined. If the subject's clinical response and/or therapeutic response is adequate, then treatment with the composition is continued as needed until the desired clinical endpoint is achieved. Alternatively, if the subject's clinical response and/or therapeutic response are inadequate at the initial dose and initial dosing regimen, the dose is escalated or deescalated until the desired clinical response and/or therapeutic response in the subject is achieved. Dose escalation or de-escalation can be performed in conjunction with a change in the dosing regimen, such as a change in dosing frequency or overall period of dose administration.

Some of the brain slice assays herein are conducted under conditions wherein the brain tissue is treated with the neuroprotective composition prior to OGD. Under those conditions, the data establishes the utility of the extract at prophylactically providing neuroprotection against damage caused by stroke.

The inventors have discovered that the neuroprotective composition of the invention provides neuroprotection mediated through at least two different pathways: the induction of brain-derived neurotrophic factor (BDNF) with oleandrin; and the induction of expression of cellular antioxidant gene transcription programs regulated through antioxidant transcriptional response elements (AREs) with triterpene(s). The triterpene(s) also induces nuclear factor erythroid 2 related factor 2 (Nrf2)-dependent antioxidant genes to provide neuroprotection. When the neuroprotective composition (unfractionated extract comprising oleandrin and triterpenes) is administered to a subject in need thereof, the composition provides neuroprotection via at least a two-fold mechanism. When the neuroprotective composition is administered to a subject in need thereof, the composition provides neuroprotection at least through ARE up-regulation.

If a clinician intends to treat a subject having a neurological condition with a combination of neuroprotective composition and one or more other therapeutic agents, and it is known that the particular neurological condition, which the subject has, is at least partially therapeutically responsive to treatment with said one or more other therapeutic agents, then the present method invention comprises: administering to the subject in need thereof a therapeutically relevant dose of neuroprotective composition and a therapeutically relevant dose of said one or more other therapeutic agents, wherein the neuroprotective composition is administered according to a first dosing regimen and the one or more other therapeutic agents is administered according to a second dosing regimen. In some embodiments, the first and second dosing regimens are the same. In some embodiments, the first and second dosing regimens are different.

If the neurological condition being treated is Alzheimer's disease, the one or more other therapeutic agents can be selected from the group consisting of BACE inhibitors or acetylcholinesterase inhibitors. In some embodiments, the one or more other therapeutic agents can be selected from the group consisting of Namenda™ (memantine HCl), Aricept™ (donepezil), Razadyne™ (galantamine), Exelon™ (rivastigmine), Cognex™ (tacrine), oleandrin.

If the neurological condition being treated is Huntington's disease, the one or more other therapeutic agents can be selected from the group consisting of natural products, anticonvulsants, NMDA (n-methyl d-aspartate) receptor antagonists, and sodium channel blockers. Exemplary agents include Vitamin E, Baclofen (a derivative of CoQ10), Lamotrigine (an anticonvulsant), remacemide (an anesthetic which is a low affinity NMDA antagonist), and riluzole (Na channel blocker). The efficacy of each of these agents is considered to be low (Mestre T. et al, Chochrane Database Systematic Reviews Jul. 8, 2009; 8(3): CD006455) on its own; however, it is expected that administration of a dosage form containing neuroprotective composition to subjects receiving one or more of these other agents will provide a subject, having a neurological disorder, an improved clinical affect as compared to administration of these agents absent the extract.

If the neurological condition being treated is stroke-mediated ischemic brain injury (ischemic stroke), then the therapeutic treatments disclosed in the literature (Gutierrez M. et al. "Cerebral protection, brain repair, plasticity and cell therapy in ischemic stroke" *Cerebrovasc. Dis.* 2009; 27 Suppl 1:177-186), e.g. intravenous thrombolysis, can be employed in addition to the extract. In some embodiments, the one or more other therapeutic agents can be selected from the group consisting of drugs such as Alteplase (a thrombolytic agent).

If the neurological condition being treated is Parkinson's disease, the one or more other therapeutic agents include a combination of carbidopa and levodopa, rasagiline, pramipexole, ropinrole, amantadine, memantine, entacapone, rotigotine, benztropine, selegiline, biperiden, a combination of carbidopa and levodopa and entacapone, trihexyphenidyl, rivastigmine, apomorphine, levodopa, carbidopa, bromocriptine, belladonna, tolcapone, or a combination thereof.

The one or more other therapeutic agents can be administered at doses and according to dosing regimens that are clinician-recognized as being therapeutically effective or at doses that are clinician-recognized as being sub-therapeutically effective. The clinical benefit and/or therapeutic effect provided by administration of a combination of the extract and one or more other therapeutic can be additive or synergistic, such level of benefit or effect being determined by comparison of administration of the combination to administration of the individual extract and one or more other therapeutic agents. The one or more other therapeutic agents can be administered at doses and according to dosing regimens as suggested or described by the U.S. Food and Drug Administration (U.S.F.D.A.), World Health Organization (W.H.O), European Medicines Agency (E.M.E.A.), Therapeutic Goods Administration (TGA, Australia), Pan American Health Organization (PAHO), Medicines and Medical Devices Safety Authority (Medsafe, New Zealand) or the various Ministries of Health worldwide.

If a cardiac glycoside is used according to the invention, it can be any cardiac glycoside known to possess Na,K-ATPase binding activity. The cardiac glycoside should be capable of crossing the blood-brain barrier and being retained in brain tissue for an extended period of time following administration. In this regard, the cardiac glycoside should be retained in the brain for at least 8 hours following administration of the cardiac glycoside due to tissue binding and a consequent low clearance rate. The preferred cardiac glycoside is oleandrin.

If present, the cardiac glycoside can be present in pure form or as a mixture with one or more other compounds. The cardiac glycoside can be present as an extract.

The extract can be prepared by supercritical fluid (SCF) carbon dioxide ($CO_2$) extraction or a chemically modified form of such an extract (e.g. an extract that includes ethanol or was made using SCF $CO_2$ and ethanol; Example 1). The extract can be obtained by extraction of plant material with an organic solvent, e.g. ethanol, methanol, propanol or other such solvents. The extract can be obtained from plant material. The plant material can be plant mass such as obtained from *Nerium* species, such as *Nerium oleander*, or of *Thevetia* species, such as *Thevetia neriifolia* or *Thevetia peruviana* (otherwise known as yellow *oleander*). The extraction process can be conducted on a dried powder of *Nerium oleander* leaves prepared according to a process described in a currently-pending U.S. provisional application Ser. No. 60/653,210 filed Feb. 15, 2005 in the name of Addington or U.S. application Ser. No. 11/340,016 filed Jan. 26, 2006 in the name of Addington, U.S. application Ser. No. 11/191,650 filed Jul. 28, 2006 (now U.S. Pat. No. 7,402,325 issued Jul. 22, 2008) in the name of Addington, or PCT International Patent Application No. PCT/US06/29061 filed Jul. 26, 2006, or Newman et al. (*Mol. Interven.* (2008), 8, 36-49), U.S. Pat. No. 8,187,644 issued May 29, 2012, or U.S. Pat. No. 8,394,434 issued Mar. 12, 2013, the entire disclosures of which are hereby incorporated by reference, or by a process described herein. These methods can also be used to prepare the unfractionated extract of *Nerium* species or of *Thevetia* species. Unless otherwise specified, the term "extract" as used herein can be taken to mean the "unfractionated extract" or a fraction of the extract or a sub-fraction of a fraction of the extract. The term "unfractionated extract" is generally taken to mean an extract obtained by extraction of plant material, wherein the extract has not been subjected to fractionation, such as fractionation or separation into individual components or groups of components by chromatography or solvent extraction, following initial preparation of the extract.

A neuroprotective composition of the invention can instead be prepared by mixing the individual components thereof into a mixture. For example, the neuroprotective composition can be prepared by mixing at least oleanolic acid and ursolic acid, and optionally betulinic acid, according to the molar ratios described herein.

As used herein, the term "oleandrin" is taken to mean all known forms of oleandrin unless otherwise specified. Oleandrin can be present in racemic, optically pure or optically enriched form. *Nerium oleander* plant material can be obtained, for example, from commercial plant suppliers such as Aldridge Nursery, Atascosa, Tex.

The unfractionated extract can be obtained by modified (e.g. ethanol) or unmodified supercritical fluid extraction of a cardiac glycoside-containing plant mass, e.g. of a *Nerium* species or *Thevetia* species containing plant mass. The supercritical fluid extract can comprise one or more pharmacologically active agents, extracted from the plant mass, that contributes to the therapeutic efficacy of the extract when administered to a subject. When two or more such agents are present, they can contribute additively or synergistically to the therapeutic efficacy of the extract.

The unfractionated extract can be prepared by various different processes. The extract can be prepared as above or according to the process described in U.S. Pat. No. 5,135,745, which is a hot-water extraction procedure for the preparation of the extract of the plant in water. The aqueous extract reportedly contains several polysaccharides with molecular weights varying from 2KD to 30KD, oleandrin and oleandrigenin, odoroside and neritaloside. The polysaccharides reportedly include acidic homopolygalacturonans or arabinogalaturonans. U.S. Pat. No. 5,869,060 to Selvaraj et al. discloses hot water extracts of *Nerium* species and methods of production thereof, e.g. Example 2. The resultant extract can then be lyophilized to produce a powder. U.S. Pat. No. 6,565,897 (U.S. Pregrant Publication No. 20020114852 and PCT International Publication No. WO 2000/016793 to Selvaraj et al.) discloses a hot-water extraction process for the preparation of a substantially sterile extract. Erdemoglu et al. (*J. Ethnopharmacol.* (2003) November 89(1), 123-129) discloses results for the comparison of aqueous and ethanolic extracts of plants, including *Nerium oleander*, based upon their anti-nociceptive and anti-inflammatory activities. Organic solvent extracts of *Nerium oleander* are disclosed by Adome et al. (*Afr. Health Sci.* (2003) August 3(2), 77-86; ethanolic extract), el-Shazly et al. (*J. Egypt Soc. Parasitol.* (1996), August 26(2), 461-473; ethanolic extract), Begum et al. (*Phytochemistry* (1999) February 50(3), 435-438; methanolic extract), Zia et al. (*J. Ethnolpharmacol.* (1995) November 49(1), 33-39; methanolic extract), and Vlasenko et al. (*Farmatsiia.* (1972) September-October 21(5), 46-47; alcoholic extract). U.S. Pregrant Patent Application Publication No. 20040247660 to Singh et al. discloses the preparation of a protein stabilized liposomal formulation of oleandrin for use in the treatment of cancer. U.S. Pregrant Patent Application Publication No. 20050026849 to Singh et al. discloses a water soluble formulation of oleandrin containing a cyclodextrin. U.S. Pregrant Patent Application Publication No. 20040082521 to Singh et al. discloses the preparation of protein stabilized nanoparticle formulations of oleandrin from the hot-water extract.

The SCF extraction can be conducted in the presence of a modifier in the supercritical fluid, such as alcohol, e.g. ethanol, to enhance extraction of the desired compound(s) from the plant mass (PCT/US06/29061 filed Jul. 26, 2005; U.S. Pat. Nos. 7,402,325; 8,394,434, 8,187,644, and U.S. Ser. No. 12/019,435 filed Jan. 24, 2008, or Newman et al. (*Mol. Interven.* (2008), 8, 36-49), the entire disclosures of which are hereby incorporated by reference). Modifiers generally possess volatility between that of the supercritical fluid and of the compound being extracted, and they must be miscible with the supercritical fluid. In some embodiments, the modifier is a liquid at ambient conditions. By way of example and without limitation, a modifier can be selected from the group consisting of ethanol, methanol, propanol, acetone, ethyl acetate, methylene chloride, etc.

The SCF extract can include a mixture of pharmacologically active compounds, such as oleandrin or other cardiac glycosides, oleaside, and other plant materials. Oleandrin extract from a supercritical fluid process contains by weight a theoretical range of 0.9% to 2.5% oleandrin. SCF extracts comprising varying amount of oleandrin have been obtained. In one embodiment, the SCF extract comprises about 2% by wt. of oleandrin.

The SCF extract (PBI-05204) comprises (consists essentially of) oleandrin, oleanolic acid, ursolic acid, and betulinic acid as the primary pharmacologically active components, optionally with minor amounts of other pharmacologically active components. The relative molar abundances of the four major components were found to be as follows.

| Compound | Content in PBI-05204 (mg/g) | Relative Molar Abundance | |
|---|---|---|---|
| Oleandrin | 20.0 | 1 | — |
| Oleanolic acid | 73.1 | 4.71 | 7.6 |
| Ursolic acid | 69.2 | 4.44 | 7.2 |
| Betulinic acid | 9.4 | 0.62 | 1 |

The SCF extract can comprise a mixture of various components. Some of those components include oleandrin, oleaside A, oleandrigenin, neritaloside, odorside (Wang X, Plomley J B, Newman R A and Cisneros A. LC/MS/MS analyses of an *oleander* extract for cancer treatment, *Analytical Chem.* 72: 3547-3552, 2000), and other unidentified components. The SCF extractable unidentified components of the SCF extract can include at least one other cardiac glycoside pharmacologically active component and/or at least one other non-cardiac glycoside pharmacologically active component that contributes to the efficacy of the oleandrin in the SCF extract. That is, at least one other SCF extractable component functions additively or synergistically with the oleandrin to provide the observed efficacy.

It is possible that the extracts also differ in their relative performance as determined by efficacy in the assays included herein. Even so, if the one or more pharmacologically active agents is present in a sufficiently high amount or concentration in the extract to be able to prepare a therapeutically relevant dose, then the extract is considered part of the invention.

Example 13 describes a chromatographic method for fractionating an SCF extract into five different fractions: 0-H, 0-2, 0-3, 0-4 and 0-5. The fractions were prepared by loading the unfractionated extract onto an ODS-silica gel column equilibrated with water and subsequently eluting different fractions of the extract by sequentially passing various portions of aqueous mobile phase varying in methanol content (30%, 55%, 80% and 100%) through the column, collecting the respective effluents (fractions) and concentrating the effluents by solvent evaporation under reduced pressure to remove the solvent, thereby providing the fractions 0-1 (or 0-H), 0-2, 0-3, 0-4 and 0-5. The fractions were analyzed according to Example 14 and their composition in terms of cardiac glycoside and other components was determined by thin layer chromatography using a sensitive dye indicator that adheres to (and hence is useful for detecting) cardiac glycosides. In addition, the presence or absence of cardiac glycosides in these fractions was analyzed using liquid chromatography/tandem mass spectrometry or DAD-UV detection.

A fraction or sub-fraction of the extract can be analyzed by liquid chromatography employing a stationary phase different than ODS-silica gel and/or by employing a mobile phase different than water. Exemplary suitable stationary phases are further described herein.

FIGS. 8A-8D depict the chromatograms obtained following HPLC analysis of the fractions Fr-0-1, Fr-0-2, Fr-O3 and Fr-0-4 of Example 13. Based upon a comparison of retention times obtained using corresponding external reference samples, it was determined the (Fr-0-2 and Fr-0-3) fractions contain oleandrin derivatives (cardiac glycosides), oleandrin (Rt=8.3 min) and other unidentified components. The bulk of the oleandrin found in the original unfractionated SCF extract was mainly in the Fr-0-3 fraction. The Fr-0-4 contained no quantifiable amounts of any cardiac glycoside. Accordingly, the composition of the fractions differed according to the content of oleandrin, cardiac glycoside and other unidentified components.

| Fraction | Oleandrin (Y/N) | Other Cardiac Glycoside (Y/N) | Neuroprotection (Y/N) |
| --- | --- | --- | --- |
| 0-H | N | N | Y |
| 0-2 | N | Y | N |
| 0-3 | Y | Y | Y |
| 0-4 (0-4A) | N | N | Y |
| 0-5 | N | N | N |

Figure 16:
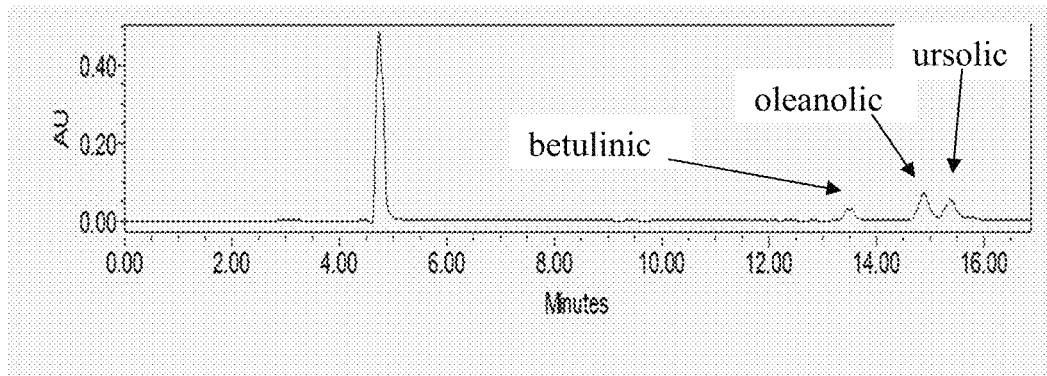
FIG. 16 depicts an HPLC chromatogram indicating the major triterpene components of Fraction 0-4 (PBI-04711), which can be prepared by mixing the individual components or as a fraction of the SCF extract. HPLC analysis was conducted according to Example 23.

The 0-4 fraction (PBI-04711) of the SCF extract comprises oleanolic acid, ursolic acid, and betulinic acid and may comprise minor amounts of other pharmacologically active components (uvaol, ursolaldehyde (ursolic aldehyde), 3β,27-dihydroxy-12-ursen-28-oic acid, E/Z-27-(p-coumaroyl)ursolic acid). An HPLC chromatogram of Fraction 0-4 is depicted in FIG. 16, which demonstrates the presence of oleanolic acid, ursolic acid and betulinic acid. The relative molar abundances of the three major components were found to be as follows.

| Compound | Relative Molar Abundance | Relative Molar Abundance (ranges) | Relative Molar Abundance (ranges) | Relative Molar Abundance (ranges) |
| --- | --- | --- | --- | --- |
| Oleanolic acid | About 3.2 | 4-2 | 3-3.5 | About 3 |
| Ursolic acid | About 2.3 | 3-1 | 2-2.5 | About 2 |
| Betulinic acid | About 1 | 0.1-1.5 | 0.8-1.2 | About 1 |

These fractions were then subjected to the neuroprotection brain slice-based assay detailed in Example 15 to determine the level of neuroprotection provided by each. The data are depicted in FIGS. 4A-4E, wherein the neuroprotective activity of an aqueous solution containing SCF extract (23 μg/ml) was compared to that of other solutions containing 0.03, 0.3 or 3 μg/ml of the fractions. All the fractions were weighed out and compared on an equal mass weight basis. It was determined that fractions (described herein) containing oleandrin, or cardiac glycoside, as well as some fractions not containing oleandrin, or cardiac glycoside, could provide neuroprotection.

These fractions were then subjected to the neuroprotection brain slice-based assay detailed in Example 21 to determine the level of neuroprotection provided by each. Coronal brain slice explants were prepared and subjected to 5.5 min. transient OGD as previously described[7] (see Methods for more detailed description). 24 h later, numbers of healthy cortical pyramidal neurons in the each brain slice were scored. The first 3 bars in each graph show: control brain slices not subjected to OGD ("Control"); negative—control brain slices subjected to OGD and treated with DMSO carrier only ("OGD"); and positive—control brain slices subjected to OGD and treated with 23 μg/ml of the full PBI-05204 extract ("PBI 23"). Sub-fractions were tested at the concentrations indicated in units of μg/ml. The data are depicted in FIGS. 4A-4E, wherein the neuroprotective activity of an aqueous solution containing SCF extract (PBI-23; 23 μg/ml) was compared to that of other solutions containing 0.3, 3 or 30 μg/ml of the fractions. It was determined that fractions (described herein) containing oleandrin, or cardiac glycoside, as well as some fractions excluding oleandrin, or cardiac glycoside, but comprising triterpene(s) could provide neuroprotection. Only Fractions 0-3 and 0-4 provided significant neuroprotection at the concentrations tested (concentrations of Fraction 0-3 of 10 μg/ml and above exhibited toxicity.

Figure 5:
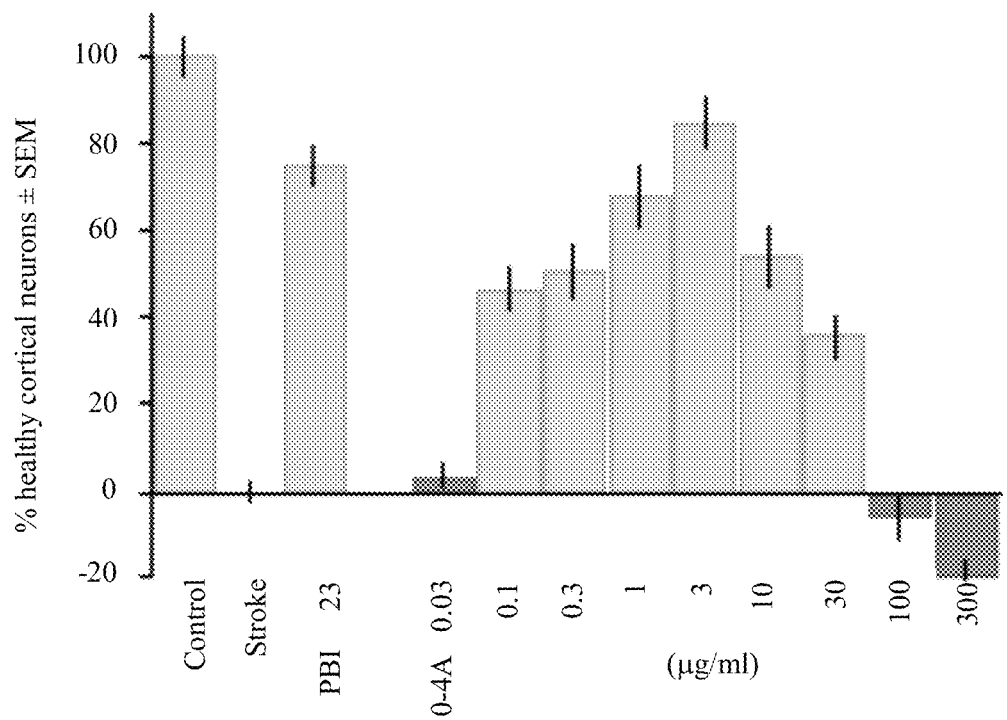
FIG. 5 depicts the results of a concentration-response brain-slice-based "stroke" assay (Example 15) for Fraction 0-4 (or 0-4A, PBI-04711) of the SCF extract of Nerium oleander versus the parent unfractionated Nerium oleander SCF extract (PBI-05204).
Figure 11:
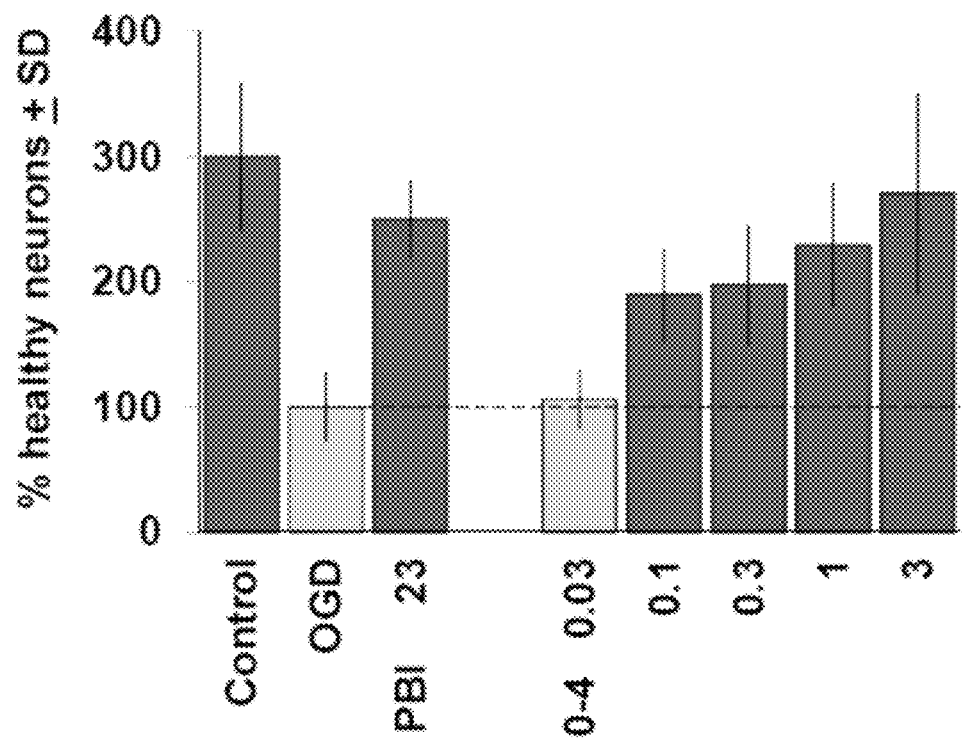
FIG. 11 depicts the results of further comparative evaluation in a neuroprotection OGD assay of a Fraction (0-4 or 0-4A; PBI-04711) of Nerium oleander SCF extract versus the unfractionated SCF extract (PBI-05204), wherein the percent of healthy cortical neurons is determined. Concentration-response relation for Fraction 0-4 in the brain slice OGD assay, in units of µg/ml; the average of 3 independent experiments is shown, with the OGD negative-control condition set to 100%. For all graphs, dark blue bars denote statistically significant differences with respect to the OGD negative-control by ANOVA followed by Dunnett's post hoc comparison test at the 0.05 confidence level.

Performance of Fraction 0-4 of the SCF extract in the brain sliced-based stroke assay (Example 15 and 21) was compared to that of the unfractionated SCF extract (PBI-05204). The performance of varying amounts (0.03 to 300 μg/ml) of the Fraction 0-4 was compared to a fixed amount of extract comprising 23 μg/ml oleandrin. The data (FIG. 5) clearly indicates that fraction 0-4 of the SCF extract of *Nerium oleander* retains its efficacy even though it does not contain oleandrin or detectable amount of any other cardiac glycoside. The lighter colored bars in FIG. 5 and FIG. 11 indicate significant difference with respect to the stroke condition (set to 0) by ANOVA followed by Dunnett's post hoc comparison test at the 0.05 confidence level. The 0-4 fraction comprises oleanolic acid, ursolic acid and betulinic acid and excludes oleandrin, neriifolin, and pharmacologically active polysaccharide obtained from *Nerium* species.

Accordingly, the invention provides plural therapeutic fractions of *Nerium* species or *Thevetia* species extract, the fractions being selected from the group consisting of: a) a fraction comprising one or more pharmacologically active agents and excluding oleandrin and other cardiac glycosides, wherein the fraction provides neuroprotection; b) a fraction comprising one or more pharmacologically active agents, oleandrin and one or more other cardiac glycosides, wherein the fraction provides neuroprotection; and c) a different fraction comprising one or more other pharmacologically active agents (different than those in a) above) and excluding oleandrin and other cardiac glycosides, wherein the fraction provides neuroprotection.

The invention provides a fraction of *Nerium* species or *Thevetia* species extract, wherein the fraction comprises at least two triterpenes or at least three triterpenes and excludes cardiac glycoside and excludes pharmacologically active polysaccharide obtained from *Nerium* species or *Thevetia* species.

Figure 19:
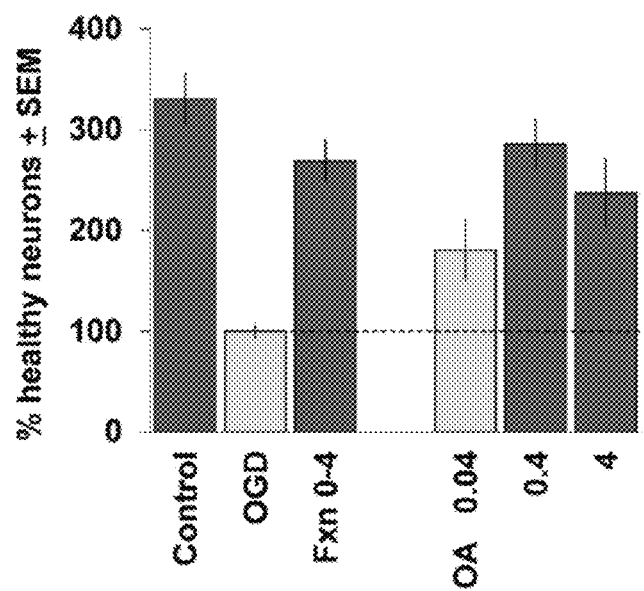
FIG. 19 depicts the results of further comparative evaluation in a neuroprotection OGD assay of Fraction 0-4 versus oleanolic acid (OA). Concentration-response relation for oleanolic acid (OA; in μg/ml) in the brain slice OGD assay; the average of 4 independent experiments is shown, with the OGD negative-control condition set to 100%. The positive control was 10 μg/ml Fraction 0-4 ("Fxn 0-4"). Dark bars denote statistically significant differences with respect to the OGD negative control by ANOVA followed by Dunnett's post hoc comparison test at the 0.05 confidence level.

We have determined that triterpenes exhibit different levels of activity in the neuroprotection OGD assay described herein. Accordingly, the level of contribution of the individual triterpenes toward efficacy of a composition containing them, e.g. an extract, fraction, sub-fraction or other composition containing them. Oleanolic acid is one of three or more triterpenes found in PBI-05204 and PBI-04711. FIG. 19 depicts the results of the comparative evaluation in a neuroprotection OGD assay of Fraction 0-4 versus oleanolic acid (OA). The assay suggests that OA accounts for a majority of the neuroprotective activity associated with OGD.

Figure 20:
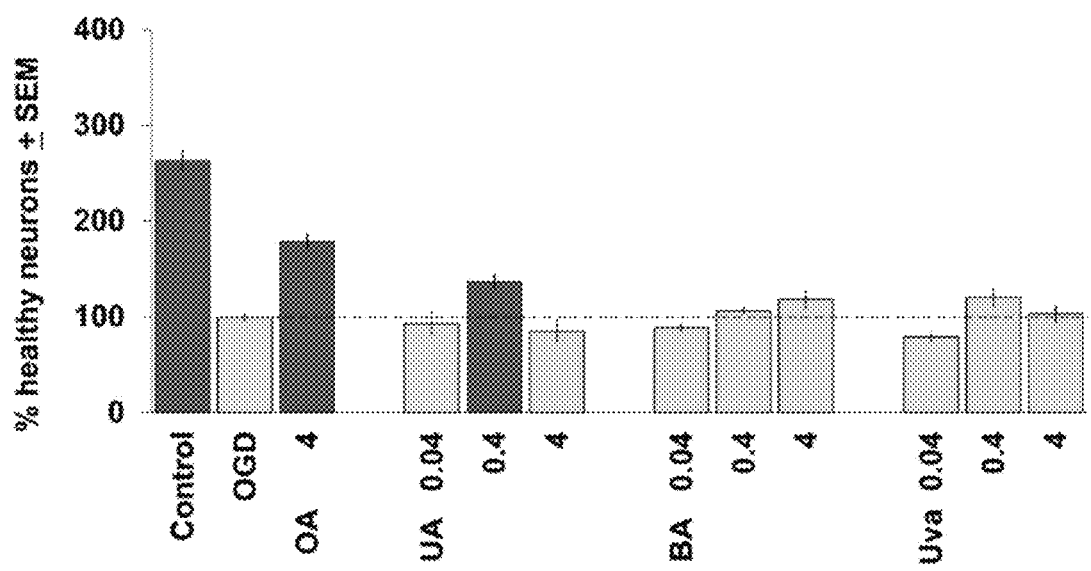
FIG. 20 depicts the results of comparative evaluation in a neuroprotection OGD assay of oleanolic acid (OA), ursolic acid (UA), betulinic acid (BA) and uvaol (Uva). Concentration-response relations for ursolic acid (UA), betulinic acid (BA), and uvalol (Uva; all in μg/ml) in the brain slice OGD assay are shown. Averages for 2 independent experiments are included for each compound, with the OGD negative-control condition scaled to 100% and data plotted on the same axes for ease of comparison. The positive control was 4 μg/ml oleanolic acid (OA). Note that these are equimolar concentrations for each compound as the molecular weights for all are identical except for uvalol which was tested at 0.039, 0.39, and 3.88 μg/ml rounded to a single significant digit for display purposes. Dark bars denote statistically significant differences with respect to the OGD negative control by ANOVA followed by Dunnett's post hoc comparison test at the 0.05 confidence level. It is important to observe that ursolic acid (UA) exhibits a rise and fall in activity as concentration is increased due to the cellular toxicity of UA.

The contribution of the various triterpenes toward efficacy of extract and fraction (compositions of the invention) was determined by comparing their activity in the OGD assay at similar concentration. It was surprisingly determined that OA provides substantially higher activity than UA; whereas BA and Uva (uvaol) provide little to no activity at the concentrations tested (FIG. 20).

The lower activity of UA in the neuroprotection OGD assay is surprising. Data (FIGS. 14A-14B and 15A-15D) obtained from the expression assays herein demonstrate that Fraction 0-4 induces substantial expression of Nrf2, Srx and Hmox1 and lower expression of Gclc and Nqo1. Data (FIGS. 17 and 18), however, demonstrate that the induction of Srx and Hmox1 is due more so to the activity of UA than of OA or BA. The efficacy (especially the broad dose response curve and high level of efficacy at low concentrations) of the composition (fraction 0-4, sub-fraction or whole extract) comprising plural triterpenes is apparently due to various different mechanisms operating synergistically to provide neuroprotection.

The invention also provides a method of fractionating an extract of *Nerium* species or *Thevetia* species in order to provide one or more therapeutically effective fractions thereof. The method comprises: a) providing an extract of *Nerium* species or *Thevetia* species; b) fractionating the extract to provide two or more different fractions of the extract, wherein a first fraction comprises one or more pharmacologically active agents, none of which is a cardiac glycoside, and a second fraction comprises one or more cardiac glycosides and further comprises one or more pharmacologically active agents, none of which is a cardiac glycoside.

The method of fractionation also comprises: a) providing an extract of *Nerium* species or *Thevetia* species; b) fractionating the extract to provide two or more different fractions of the extract, wherein a fraction comprises two to three triterpenes, and a fraction comprises one or more cardiac glycosides.

In some embodiments, the fractionation is performed by liquid chromatography with a stationary phase and a mobile phase. In some embodiments, the stationary phase comprises a medium selected from the group consisting of "reverse phase" resin, an inert non-polar substance that achieves sufficient packing for use in chromatography, e.g. composed of short (C8 to C18) carbon chains bonded to silica, cyano-bonded silica or phenyl bonded silica, ion-exchange resins (cation or anion based), "normal phase" resin, e.g. silica or organic moieties with cyano and amino functional groups. In some embodiments, the mobile phase comprises a solvent selected from the group consisting of water, methanol, ethanol, acetonitrile, tetrahydrofuran, water based buffered solutions or mixtures thereof. In some embodiments, the mobile phase comprises aqueous methanol, wherein the content of methanol is increased sequentially from about 30% up to 100% and the stationary phase is ODS-silica gel. The chromatography can be conducted using gradient elution mobile phase, stepwise elution mobile phase or a fixed composition mobile phase.

A fraction of extract can be sub-fractionated to provide two or more different sub-fractions of a fraction of extract. Sub-fractionation can be carried out by liquid chromatography of the fraction. A suitable stationary phase for liquid chromatography can comprise silica gel or other resins such as ion-exchange media, alumina or nonbonded C18 material and a suitable mobile phase for liquid chromatography can comprise a combination of two or more organic solvents differing in polarity: a less polar organic solvent and a more polar organic solvent. A suitable polar organic solvent can be tetrahydrofuran, dichloromethane, ethyl acetate, acetone, dimethylformamide, acetonitrile, n-butanol, isopropanol, n-propanol, ethanol, methanol, acetic acid and water. A suitable non-polar organic solvent can be ethyl acetate pentane, cyclopentane, hexane, cyclohexane, benzene, toluene, 1,4-dioxane, chloroform or diethyl ether.

Buffering agents for use in buffered solutions include any of those already known in the art of liquid chromatography. Exemplary buffering agents include those containing phosphate, acetate, citrate, formate, phosphate, trifluoroacetic acid, chloroacetate, sulfonate, alkyl amine, TAE, TBE, ammonia, BuffAR, carbonate, HEPES, MES, thiocyanate, CAPS, CHES, guanidine, MOPS, PIPES, TRIS, sulfate, hydroxide, alkali metal halide, tricine, or amino acid ions or combinations thereof. One or more ion-pairing agents and/or one or more organic modifiers can also be included in the mobile phase.

Other types of chromatography that can be used to fractionate the extract include size exclusion chromatography, normal phase chromatography, ion exchange chromatography, hydrophobic interaction chromatography or combinations thereof. It is also possible to use combined forms of different types of chromatography. A stationary phase can include a medium that is a combination of two or more different media used for reverse phase, size exclusion, ion exchange or hydrophobic interaction chromatography, e.g. a combination of reverse phase stationary phase and size exclusion stationary phase, combination of reverse phase stationary phase and ion exchange stationary phase, or other such combinations or two, three or four different stationary phase media. The stationary phase medium can be porous, non-porous, surface porous, diffusive porous or totally porous.

The invention provides a method of fractionating an extract comprising: a) providing an extract of extract obtained from *Nerium* species or *Thevetia* species; b) fractionating the extract by column chromatography, with ODS-silica gel as stationary phase and aqueous methanol as mobile phase, to provide at least two different fractions: a first fraction comprising at least one cardiac glycoside and at least one non-cardiac glycoside pharmacologically active agent, and another fraction excluding cardiac glycoside and comprising at least one non-cardiac glycoside pharmacologically active agent; c1) sub-fractionating the other fraction of b) by column chromatography, with silica gel as stationary phase and a mixture of at least two organic solvents differing in polarity as mobile phase, to provide at least two different sub-fractions: a sub-fraction comprising one or more triterpenes (optionally with one or more steroids) and another sub-fraction comprising two or more different tripenes and excluding a steroid, wherein the sub-fractions exclude cardiac glycoside. In other words, sub-fractionating can provide sub-fractions comprising triterpene(s) and optionally further comprising steroid(s).

In some embodiments, the method further comprises: c2) sub-fractionating the first fraction of b) by column chromatography, with silica gel as stationary phase and a mixture of at least two organic solvents differing in polarity as mobile phase, to provide at least two different sub-fractions: a sub-fraction comprising one or more steroids and one or more tritepenes, and another sub-fraction comprising two or more different tripenes and excluding a steroid, wherein either one or both of the sub-fractions further comprises cardiac glycoside.

The neuroprotective composition can be formulated in any suitable pharmaceutically acceptable dosage form. Parenteral, otic, ophthalmic, nasal, inhalable, buccal, sublingual, enteral, topical, oral, peroral, and injectable dosage forms are particularly useful. Particular dosage forms include a solid or liquid dosage forms. Exemplary suitable dosage forms include tablet, capsule, pill, caplet, troche, sache, solution, suspension, dispersion, vial, bag, bottle, injectable liquid, i.v. (intravenous), i.m. (intramuscular) or i.p. (intraperitoneal) administrable liquid and other such dosage forms known to the artisan of ordinary skill in the pharmaceutical sciences.

Suitable dosage forms containing the neuroprotective composition can be prepared by mixing the neuroprotective composition with pharmaceutically acceptable excipients as described herein or as described in Pi et al. ("Ursolic acid nanocrystals for dissolution rate and bioavailability enhancement: influence of different particle size" in Curr. Drug Deliv. (March 2016), 13(8), 1358-1366), Yang et al. ("Self-microemulsifying drug delivery system for improved oral bioavailability of oleanolic acid: design and evaluation" in Int. J. Nanomed. (2013), 8(1), 2917-2926), Li et al. (Development and evaluation of optimized sucrose ester stabilized oleanolic acid nanosuspensions prepared by wet ball milling with design of experiments" in Biol. Pharm. Bull. (2014), 37(6), 926-937), Zhang et al. ("Enhancement of oral bioavailability of triterpene through lipid nanospheres: preparation, characterization, and absorption evaluation" in J. Pharm. Sci. (June 2014), 103(6), 1711-1719), Godugu et al. ("Approaches to improve the oral bioavailability and effects of novel anticancer drugs berberine and betulinic acid" in PLoS One (March 2014), 9(3):e89919), Zhao et al. ("Preparation and characterization of betulin nanoparticles for oral hypoglycemic drug by antisolvent precipitation" in Drug Deliv. (September 2014), 21(6), 467-479), Yang et al. ("Physicochemical properties and oral bioavailability of ursolic acid nanoparticles using supercritical anti-solvent (SAS) process" in Food Chem. (May 2012), 132(1), 319-325), Cao et al. ("Ethylene glycol-linked amino acid diester prodrugs of oleanolic acid for PEPT1-mediated transport: synthesis, intestinal permeability and pharmacokinetics" in Mol. Pharm. (August 2012), 9(8), 2127-2135), Li et al. ("Formulation, biological and pharmacokinetic studies of sucrose ester-stabilized nanosuspensions of oleanolic acid" in Pharm. Res. (August 2011), 28(8), 2020-2033), Tong et al. ("Spray freeze drying with polyvinylpyrrolidone and sodium caprate for improved dissolution and oral bioavailability of oleanolic acid, a BCS Class IV compound" in Int. J. Pharm. (February 2011), 404(1-2), 148-158), Xi et al. (Formulation development and bioavailability evaluation of a self-nanoemulsified drug delivery system of oleanolic acid" in AAPS PharmSciTech (2009), 10(1), 172-182), Chen et al. ("Oleanolic acid nanosuspensions: preparation, in-vitro characterization and enhanced hepatoprotective effect" in J. Pharm. Pharmacol. (February 2005), 57(2), 259-264), the entire disclosures of which are hereby incorporated by reference.

Suitable dosage forms can also be made according to U.S. Pat. No. 8,187,644 B2 to Addington, which issued May 29, 2012, U.S. Pat. No. 7,402,325 B2 to Addington, which issued Jul. 22, 2008, U.S. Pat. No. 8,394,434 B2 to Addington et al, which issued Mar. 12, 2013, the entire disclosures of which are hereby incorporated by reference. Suitable dosage forms can also be made as described in Examples 13-15.

The amount of neuroprotective composition incorporated in a dose of the invention will be at least one or more dosage forms and can be selected according to known principles of pharmacy. An effective amount or therapeutically relevant amount of therapeutic compound is specifically contemplated. By the term "effective amount", it is understood that, with respect to, for example, pharmaceuticals, a pharmaceutically effective amount is contemplated. A pharmaceutically effective amount is the amount or quantity of active ingredient which is enough for the required or desired therapeutic response, or in other words, the amount, which is sufficient to elicit an appreciable biological response when, administered to a patient. The appreciable biological response may occur as a result of administration of single or multiple doses of an active substance. A dose may comprise one or more dosage forms. It will be understood that the specific dose level for any patient will depend upon a variety of factors including the indication being treated, severity of the indication, patient health, age, gender, weight, diet, pharmacological response, the specific dosage form employed, and other such factors.

The desired dose for oral administration is up to 5 dosage forms although as few as one and as many as ten dosage forms may be administered as a single dose. Exemplary dosage forms contain 0.1 to 5 mg of the neuroprotective composition per dosage form, for a total 0.1 to 500 mg (1 to 10 dose levels) per dose. Doses will be administered according to dosing regimens that may be predetermined and/or tailored to achieve specific therapeutic response or clinical benefit in a subject.

Some embodiments of the dosage form are not enteric coated and release their charge of neuroprotective composition within a period of 0.5 to 1 hours or less. Some embodiments of the dosage form are enteric coated and release their charge of neuroprotective composition downstream of the stomach, such as from the jejunum, ileum, small intestine, and/or large intestine (colon). Enterically coated dosage forms will release the neuroprotective composition into the systemic circulation within 1-10 hr after oral administration.

The neuroprotective composition consisting essentially of OA and UA or of OA, UA and BA is administered to a subject, such that the total amount of triterpene present constitutes an effective dose. The projected human dose for the mixture of triterpenes is expected to be about 0.05 mg to about 1 mg of total triterpene/kg of body weight/day.

It should be noted that a compound herein might possess one or more functions in the formulation of the invention. For example, a compound might serve as both a surfactant and a water miscible solvent or as both a surfactant and a water immiscible solvent.

A liquid composition can comprise one or more pharmaceutically acceptable liquid carriers. The liquid carrier can be an aqueous, non-aqueous, polar, non-polar, and/or organic carrier. Liquid carriers include, by way of example and without limitation, a water miscible solvent, water immiscible solvent, water, buffer and mixtures thereof.

As used herein, the terms "water soluble solvent" or "water miscible solvent", which terms are used interchangeably, refer to an organic liquid which does not form a biphasic mixture with water or is sufficiently soluble in water to provide an aqueous solvent mixture containing at least five percent of solvent without separation of liquid phases. The solvent is suitable for administration to humans or animals. Exemplary water soluble solvents include, by way of example and without limitation, PEG (poly(ethylene glycol)), PEG 400 (poly(ethylene glycol having an approximate molecular weight of about 400), ethanol, methanol, alkanol, alcohol, ether, propylene glycol, glycerin, triacetin, poly(propylene glycol), PVP (poly(vinyl pyrrolidone)), dimethylsulfoxide, N,N-dimethylformamide, formamide, N,N-dimethylacetamide, pyridine, propanol, N-methylacetamide, butanol, soluphor (2-pyrrolidone), pharmasolve (N-methyl-2-pyrrolidone).

As used herein, the terms "water insoluble solvent" or "water immiscible solvent", which terms are used interchangeably, refer to an organic liquid which forms a biphasic mixture with water or provides a phase separation when the concentration of solvent in water exceeds five percent. The solvent is suitable for administration to humans or animals. Exemplary water insoluble solvents include, by way of example and without limitation, medium/long chain triglycerides, oil, castor oil, corn oil, vitamin E, vitamin E derivative, oleic acid, fatty acid, olive oil, softisan 645 (Diglyceryl Caprylate/Caprate/Stearate/Hydroxy stearate adipate), miglyol, captex (Captex 350: Glyceryl Tricaprylate/Caprate/Laurate triglyceride; Captex 355: Glyceryl Tricaprylate/Caprate triglyceride; Captex 355 EP/NF: Glyceryl Tricaprylate/Caprate medium chain triglyceride).

Suitable solvents are listed in the "International Conference on Harmonisation of Technical Requirements for Registration of Pharmaceuticals for Human Use (ICH) guidance for industry *Q3C Impurities: Residual Solvents*" (1997), which makes recommendations as to what amounts of residual solvents are considered safe in pharmaceuticals. Exemplary solvents are listed as class 2 or class 3 solvents. Class 3 solvents include, for example, acetic acid, acetone, anisole, 1-butanol, 2-butanol, butyl acetate, tert-butlymethyl ether, cumene, ethanol, ethyl ether, ethyl acetate, ethyl formate, formic acid, heptane, isobutyl acetate, isopropyl acetate, methyl acetate, methyl-1-butanol, methylethyl ketone, methylisobutyl ketone, 2-methyl-1-propanol, pentane, 1-pentanol, 1-propanol, 2-propanol, or propyl acetate.

Other materials that can be used as water immiscible solvents in the invention include: Captex 100: Propylene Glycol Dicaprate; Captex 200: Propylene Glycol Dicaprylate/Dicaprate; Captex 200 P: Propylene Glycol Dicaprylate/Dicaprate; Propylene Glycol Dicaprylocaprate; Captex 300: Glyceryl Tricaprylate/Caprate; Captex 300 EP/NF: Glyceryl Tricaprylate/Caprate Medium Chain Triglycerides; Captex 350: Glyceryl Tricaprylate/Caprate/Laurate; Captex 355: Glyceryl Tricaprylate/Caprate; Captex 355 EP/NF: Glyceryl Tricaprylate/Caprate Medium Chain Triglycerides; Captex 500: Triacetin; Captex 500 P: Triacetin (Pharmaceutical Grade); Captex 800: Propylene Glycol Di (2-Ethythexanoate); Captex 810 D: Glyceryl Tricaprylate/Caprate/Linoleate; Captex 1000: Glyceryl Tricaprate; Captex CA: Medium Chain Triglycerides; Captex MCT-170: Medium Chain Triglycerides; Capmul GMO:Glyceryl Monooleate; Capmul GMO-50 EP/NF: Glyceryl Monooleate; Capmul MCM: Medium Chain Mono- & Diglycerides; Capmul MCM C8: Glyceryl Monocaprylate; Capmul MCM C10: Glyceryl Monocaprate; Capmul PG-8: Propylene Glycol Monocaprylate; Capmul PG-12: Propylene Glycol Monolaurate; Caprol 10G100: Decaglycerol Decaoleate; Caprol 3GO:Triglycerol Monooleate; Caprol ET: Polyglycerol Ester of Mixed Fatty Acids; Caprol MPGO:Hexaglycerol Dioleate; Caprol PGE 860: Decaglycerol Mono-, Dioleate.

As used herein, a "surfactant" refers to a compound that comprises polar or charged hydrophilic moieties as well as non-polar hydrophobic (lipophilic) moieties; i.e., a surfactant is amphiphilic. The term surfactant may refer to one or a mixture of compounds. A surfactant can be a solubilizing agent, an emulsifying agent or a dispersing agent. A surfactant can be hydrophilic or hydrophobic.

The hydrophilic surfactant can be any hydrophilic surfactant suitable for use in pharmaceutical compositions. Such surfactants can be anionic, cationic, zwitterionic or non-ionic, although non-ionic hydrophilic surfactants are presently preferred. As discussed above, these non-ionic hydrophilic surfactants will generally have HLB values greater than about 10. Mixtures of hydrophilic surfactants are also within the scope of the invention.

Similarly, the hydrophobic surfactant can be any hydrophobic surfactant suitable for use in pharmaceutical compositions. In general, suitable hydrophobic surfactants will have an HLB value less than about 10. Mixtures of hydrophobic surfactants are also within the scope of the invention.

Examples of additional suitable solubilizer include: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol, available commercially from BASF under the trade name Tetraglycol) or methoxy PEG (Union Carbide); amides, such as 2-pyrrolidone, 2-piperidone, caprolactam, N-alkylpyrrolidone, N-hydroxyalkylpyrrolidone, N-alkylpiperidone, N-alkylcaprolactam, dimethylacetamide, and polyvinypyrrolidone; esters, such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, caprolactone and isomers thereof, valerolactone and isomers thereof, butyrolactone and isomers thereof; and other solubilizers known in the art, such as dimethyl acetamide, dimethyl isosorbide (Arlasolve DMI (ICI)), N-methyl pyrrolidones (Pharmasolve (ISP)), monooctanoin, diethylene glycol nonoethyl ether (available from Gattefosse under the trade name Transcutol), and water. Mixtures of solubilizers are also within the scope of the invention.

Except as indicated, compounds mentioned herein are readily available from standard commercial sources.

The clear liquid composition is visually clear to the unaided eye, as it will contain less than 5%, less than 3% or less than 1% by wt. of suspended solids based upon the total weight of the composition.

Although not necessary, a composition or kit of the present invention may include a chelating agent, preservative, antioxidant, adsorbents, acidifying agent, alkalizing agent, antifoaming agent, buffering agent, colorant, electrolyte, salt, stabilizer, tonicity modifier, diluent, other pharmaceutical excipient, or a combination thereof.

As used herein, the term "antioxidant" is intended to mean an agent that inhibits oxidation and is thus used to prevent the deterioration of preparations by the oxidative process. Such compounds include, by way of example and without limitation, ascorbic acid, ascorbic palmitate, Vitamin E, Vitamin E derivative, butylated hydroxyanisole, butylated hydroxytoluene, hypophosphorous acid, monothioglycerol, propyl gallate, sodium ascorbate, sodium bisulfite, sodium formaldehyde sulfoxylate, sodium metalbisulfite and other such materials known to those of ordinary skill in the art.

As used herein, the term chelating agent is intended to mean a compound that chelates metal ions in solution. Exemplary chelating agents include EDTA (tetrasodium ethylenediaminetetraacetate), DTPA (pentasodium diethylenetriaminepentaacetate), HEDTA (trisodium salt of N-(hydroxyethyl)-ethylene-diaminetriacetic acid), NTA (trisodium nitrilotriacetate), disodium ethanoldiglycine (Na$_2$EDG), sodium diethanolglycine (DEGNa), citric acid, and other compounds known to those of ordinary skill in the art.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "alkalizing agent" is intended to mean a compound used to provide an alkaline medium. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, and trolamine and others known to those of ordinary skill in the art.

As used herein, the term "acidifying agent" is intended to mean a compound used to provide an acidic medium. Such compounds include, by way of example and without limitation, acetic acid, amino acid, citric acid, fumaric acid and other alpha-hydroxy acids, hydrochloric acid, ascorbic acid, and nitric acid and others known to those of ordinary skill in the art.

As used herein, the term "antifoaming agent" is intended to mean a compound or compounds that prevents or reduces the amount of foaming that forms on the surface of the fill composition. Suitable antifoaming agents include by way of example and without limitation, dimethicone, SIMETHICONE, octoxynol and others known to those of ordinary skill in the art.

As used herein, the term "buffering agent" is intended to mean a compound used to resist a change in pH upon dilution or addition of acid or alkali. Such compounds include, by way of example and without limitation, potassium metaphosphate, potassium phosphate, monobasic sodium acetate and sodium citrate anhydrous and dehydrate and other such materials known to those of ordinary skill in the art.

As used herein, the term "diluent" or "filler" is intended to mean inert substances used as fillers to create the desired bulk, flow properties, and compression characteristics in the preparation of tablets and capsules. Such compounds include, by way of example and without limitation, dibasic calcium phosphate, kaolin, lactose, sucrose, mannitol, microcrystalline cellulose, powdered cellulose, precipitated calcium carbonate, sorbitol, and starch and other materials known to one of ordinary skill in the art.

As used herein, the term "preservative" is intended to mean a compound used to prevent the growth of microorganisms. Such compounds include, by way of example and without limitation, benzalkonium chloride, benzethonium chloride, benzoic acid, benzyl alcohol, cetylpyridinium chloride, chlorobutanol, phenol, phenylethyl alcohol, phenylmercuric nitrate, phenylmercuric acetate, thimerosal, metacresol, myristylgamma picolinium chloride, potassium benzoate, potassium sorbate, sodium benzoate, sodium propionate, sorbic acid, thymol, and methyl, ethyl, propyl, or butyl parabens and others known to those of ordinary skill in the art.

As used herein, the term "colorant" is intended to mean a compound used to impart color to pharmaceutical preparations. Such compounds include, by way of example and without limitation, FD&C Red No. 3, FD&C Red No. 20, FD&C Yellow No. 6, FD&C Blue No. 2, FD&C Green No. 5, FD&C Orange No. 5, FD&C Red No. 8, caramel, and iron oxide (black, red, yellow), other FD&C dyes and natural coloring agents such as grape skin extract, beet red powder, beta-carotene, annato, carmine, turmeric, paprika, combinations thereof and other such materials known to those of ordinary skill in the art.

As used herein, the term "stabilizer" is intended to mean a compound used to stabilize an active agent against physical, chemical, or biochemical processes that would otherwise reduce the therapeutic activity of the agent. Suitable stabilizers include, by way of example and without limitation, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate and sodium saccharin and others known to those of ordinary skill in the art.

As used herein, the term "tonicity modifier" is intended to mean a compound or compounds that can be used to adjust the tonicity of the liquid formulation. Suitable tonicity modifiers include glycerin, lactose, mannitol, dextrose, sodium chloride, sodium sulfate, sorbitol, trehalose and others known to those or ordinary skill in the art.

The composition of the invention can also include oils such as fixed oils, peanut oil, sesame oil, cottonseed oil, corn oil and olive oil; fatty acids such as oleic acid, stearic acid and isostearic acid; and fatty acid esters such as ethyl oleate, isopropyl myristate, fatty acid glycerides and acetylated fatty acid glycerides. The composition can also include alcohol such as ethanol, isopropanol, hexadecyl alcohol, glycerol and propylene glycol; glycerol ketals such as 2,2-dimethyl-1,3-dioxolane-4-methanol; ethers such as poly (ethylene glycol) 450; petroleum hydrocarbons such as mineral oil and petrolatum; water; a pharmaceutically suitable surfactant, suspending agent or emulsifying agent; or mixtures thereof.

It should be understood that the compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

One or more of the components of the formulation can be present in its free base, free acid or pharmaceutically or analytically acceptable salt form. As used herein, "pharmaceutically or analytically acceptable salt" refers to a compound that has been modified by reacting it with an acid, or a base, as needed to form an ionically bound pair. Examples of acceptable salts include conventional non-toxic salts formed, for example, from non-toxic inorganic or organic acids. Suitable non-toxic salts include those derived from inorganic acids such as hydrochloric, hydrobromic, sulfuric, sulfonic, sulfamic, phosphoric, nitric and others known to those of ordinary skill in the art. The salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill in the art. Lists of other suitable salts are found in *Remington's Pharmaceutical Sciences*, 17$^{th}$. ed., Mack Publishing Company, Easton, Pa., 1985, p. 1418, the relevant disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with tissues of human beings and animals and without excessive toxicity, irritation, allergic response, or any other problem or complication, commensurate with a reasonable benefit/risk ratio.

A dosage form can be made by any conventional means known in the pharmaceutical industry. A liquid dosage form can be prepared by providing at least one liquid carrier and oleandrin or oleandrin-containing extract in a container. One or more other excipients can be included in the liquid dosage form. A solid dosage form can be prepared by providing at least one solid carrier and oleandrin or oleandrin-containing extract. One or more other excipients can be included in the solid dosage form.

A dosage form can be packaged using conventional packaging equipment and materials. It can be included in a pack, bottle, via, bag, syringe, envelope, packet, blister pack, box, ampoule, or other such container.

The invention includes a method for improving the clinical status of a statistically significant number of subjects of in a population of subjects having a neurological condition, the method comprising: administering to the population of subjects a neuroprotective composition; and determining the clinical status of the subjects to establish the improved clinical status. In some embodiments, the statistically significant number is at least 5%, at least 10%, at least 20%, at least 30%, at least 40%, at least 50%, at least 60%, at least 70%, at least 80% or at least 90% of the population.

As used herein a "derivative" is: a) a chemical substance that is related structurally to a first chemical substance and theoretically derivable from it; b) a compound that is formed from a similar first compound or a compound that can be imagined to arise from another first compound, if one atom of the first compound is replaced with another atom or group of atoms; c) a compound derived or obtained from a parent compound and containing essential elements of the parent compound; or d) a chemical compound that may be produced from first compound of similar structure in one or more steps. For example, a derivative may include a deuterated form, oxidized form, dehydrated, unsaturated, polymer conjugated or glycosilated form thereof or may include an ester, amide, lactone, homolog, ether, thioether, cyano, amino, alkylamino, sulfhydryl, heterocyclic, heterocyclic ring-fused, polymerized, pegylated, benzylidenyl, triazolyl, piperazinyl or deuterated form thereof.

As used herein, the individually named triterpenes can be independently selected upon each occurrence in their native (unmodified, free acid) form, in their salt form, in derivative form, prodrug form, or a combination thereof. Compositions containing and methods employing deuterated forms of the triterpenes are also within the scope of the invention.

Oleanolic acid derivatives, prodrugs and salts are disclosed in US 20150011627 A1 to Gribble et al. which published Jan. 8, 2015, US 20140343108 A1 to Rong et al which published Nov. 20, 2014, US 20140343064 A1 to Xu et al. which published Nov. 20, 2014, US 20140179928 A1 to Anderson et al. which published Jun. 26, 2014, US 20140100227 A1 to Bender et al. which published Apr. 10, 2014, US 20140088188 A1 to Jiang et al. which published Mar. 27, 2014, US 20140088163 A1 to Jiang et al. which published Mar. 27, 2014, US 20140066408 A1 to Jiang et al. which published Mar. 6, 2014, US 20130317007 A1 to Anderson et al. which published Nov. 28, 2013, US 20130303607 A1 to Gribble et al. which published Nov. 14, 2013, US 20120245374 to Anderson et al. which published Sep. 27, 2012, US 20120238767 A1 to Jiang et al. which published Sep. 20, 2012, US 20120237629 A1 to Shode et al. which published Sep. 20, 2012, US 20120214814 A1 to Anderson et al. which published Aug. 23, 2012, US 20120165279 A1 to Lee et al. which published Jun. 28, 2012, US 20110294752 A1 to Arntzen et al. which published Dec. 1, 2011, US 20110091398 A1 to Majeed et al. which published Apr. 21, 2011, US 20100189824 A1 to Arntzen et al. which published Jul. 29, 2010, US 20100048911 A1 to Jiang et al. which published Feb. 25, 2010, and US 20060073222 A1 to Arntzen et al. which published Apr. 6, 2006, the entire disclosures of which are hereby incorporated by reference.

Ursolic acid derivatives, prodrugs and salts are disclosed in US 20150011627 A1 to Gribble et al. which published Jan. 8, 2015, US 20130303607 A1 to Gribble et al. which published Nov. 14, 2013, US 20150218206 A1 to Yoon et al. which published Aug. 6, 2015, U.S. Pat. No. 6,824,811 to Fritsche et al. which issued Nov. 30, 2004, U.S. Pat. No. 7,718,635 to Ochiai et al. which issued May 8, 2010, U.S. Pat. No. 8,729,055 to Lin et al. which issued May 20, 2014, and U.S. Pat. No. 9,120,839 to Yoon et al. which issued Sep. 1, 2015, the entire disclosures of which are hereby incorporated by reference.

Betulinic acid derivatives, prodrugs and salts are disclosed in US 20150011627 A1 to Gribble et al. which published Jan. 8, 2015, US 20130303607 A1 to Gribble et al. which published Nov. 14, 2013, US 20120237629 A1 to Shode et al. which published Sep. 20, 2012, US 20170204133 A1 to Regueiro-Ren et al. which published Jul. 20, 2017, US 20170096446 A1 to Nitz et al. which published Apr. 6, 2017, US 20150337004 A1 to Parthasaradhi Reddy et al. which published Nov. 26, 2015, US 20150119373 A1 to Parthasaradhi Reddy et al. which published Apr. 30, 2015, US 20140296546 A1 to Yan et al. which published Oct. 2, 2014, US 20140243298 A1 to Swidorski et al. which published Aug. 28, 2014, US 20140221328 A1 to Parthasaradhi Reddy et al. which published Aug. 7, 2014, US 20140066416 A1 to Leunis et al. which published Mar. 6, 2014, US 20130065868 A1 to Durst et al. which published Mar. 14, 2013, US 20130029954 A1 to Regueiro-Ren et al. which published Jan. 31, 2013, US 20120302530 A1 to Zhang et al. which published Nov. 29, 2012, US 20120214775 A1 to Power et al. which published Aug. 23, 2012, US 20120101149 A1 to Honda et al. which published Apr. 26, 2012, US 20110224182 to Bullock et al. which published Sep. 15, 2011, US 20110313191 A1 to Hemp et al. which published Dec. 22, 2011, US 20110224159 A1 to Pichette et al. which published Sep. 15, 2011, US 20110218204 to Parthasaradhi Reddy et al. which published Sep. 8, 2011, US 20090203661 A1 to Safe et al. which published Aug. 13, 2009, US 20090131714 A1 to Krasutsky et al. which published May 21, 2009, US 20090076290 to Krasutsky et al. which published Mar. 19, 2009, US 20090068257 A1 to Leunis et al. which published Mar. 12, 2009, US 20080293682 to Mukherjee et al. which published Nov. 27, 2008, US 20070072835 A1 to Pezzuto et al. which published Mar. 29, 2007, US 20060252733 A1 to Jansen et al. which published Nov. 9, 2006, and U.S. Pat. No. 2006/025274 A1 to O'Neill et al. which published Nov. 9, 2006, the entire disclosures of which are hereby incorporated by reference.

In view of the above description and the examples below, one of ordinary skill in the art will be able to practice the invention as claimed without undue experimentation. The foregoing will be better understood with reference to the following examples that detail certain procedures for the preparation of embodiments of the present invention. All references made to these examples are for the purposes of illustration. The following examples should not be considered exhaustive, but merely illustrative of only a few of the many embodiments contemplated by the present invention.

Oleandrin, oleanolic acid, ursolic acid and betulinic acid can be purchased from Sigma Chemical Co. (St. Louis, Mo.). Deuterated forms of oleandrin, oleanolic acid, ursolic acid and betulinic acid are considered derivatives of the same, respectively.

Example 1

Supercritical Fluid Extraction of Powdered Oleander Leaves

Method A. With Carbon Dioxide.

Powdered *oleander* leaves were prepared by harvesting, washing, and drying *oleander* leaf material, then passing the *oleander* leaf material through a comminuting and dehydrating apparatus such as those described in U.S. Pat. Nos. 5,236,132, 5,598,979, 6,517,015, and 6,715,705. The weight of the starting material used was 3.94 kg.

The starting material was combined with pure $CO_2$ at a pressure of 300 bar (30 MPa, 4351 psi) and a temperature of 50° C. (122° F.) in an extractor device. A total of 197 kg of $CO_2$ was used, to give a solvent to raw material ratio of 50:1. The mixture of $CO_2$ and raw material was then passed through a separator device, which changed the pressure and temperature of the mixture and separated the extract from the carbon dioxide.

The extract (65 g) was obtained as a brownish, sticky, viscous material having a nice fragrance. The color was likely caused by chlorophyll. For an exact yield determination, the tubes and separator were rinsed out with acetone and the acetone was evaporated to give an addition 9 g of extract. The total extract amount was 74 g. Based on the weight of the starting material, the yield of the extract was 1.88%. The content of oleandrin in the extract was calculated using high pressure liquid chromatography and mass spectrometry to be 560.1 mg, or a yield of 0.76%.

Method B. With Mixture of Carbon Dioxide and Ethanol

Powdered *oleander* leaves were prepared by harvesting, washing, and drying *oleander* leaf material, then passing the *oleander* leaf material through a comminuting and dehydrating apparatus such as those described in U.S. Pat. Nos. 5,236,132, 5,598,979, 6,517,015, and 6,715,705. The weight of the starting material used was 3.85 kg.

The starting material was combined with pure $CO_2$ and 5% ethanol as a modifier at a pressure of 280 bar (28 MPa, 4061 psi) and a temperature of 50° C. (122° F.) in an extractor device. A total of 160 kg of $CO_2$ and 8 kg ethanol was used, to give a solvent to raw material ratio of 43.6 to 1. The mixture of $CO_2$, ethanol, and raw material was then passed through a separator device, which changed the pressure and temperature of the mixture and separated the extract from the carbon dioxide.

The extract (207 g) was obtained after the removal of ethanol as a dark green, sticky, viscous mass obviously containing some chlorophyll. Based on the weight of the starting material, the yield of the extract was 5.38%. The content of oleandrin in the extract was calculated using high pressure liquid chromatography and mass spectrometry to be 1.89 g, or a yield of 2.1%.

Example 2

Hot-Water Extraction of Powdered Oleander Leaves

Hot water extraction is typically used to extract oleandrin and other active components from *oleander* leaves. Examples of hot water extraction processes can be found in U.S. Pat. Nos. 5,135,745 and 5,869,060.

A hot water extraction was carried out using 5 g of powdered *oleander* leaves. Ten volumes of boiling water (by weight of the *oleander* starting material) were added to the powdered *oleander* leaves and the mixture was stirred constantly for 6 hours. The mixture was then filtered and the leaf residue was collected and extracted again under the same conditions. The filtrates were combined and lyophilized. The appearance of the extract was brown. The dried extract material weighed about 1.44 g. 34.21 mg of the extract material was dissolved in water and subjected to oleandrin content analysis using high pressure liquid chromatography and mass spectrometry. The amount of oleandrin was determined to be 3.68 mg. The oleandrin yield, based on the amount of extract, was calculated to be 0.26%. The table below shows a comparison between the oleandrin yields for the two supercritical carbon dioxide extractions of Example 1 and the hot water extraction.

Comparison of Yields

| Extraction Medium | Oleandrin yield based on total extract weight |
|---|---|
| Supercritical Carbon Dioxide: Example 1, Method A | 0.76% |
| Supercritical Carbon Dioxide: Example 1, Method B | 2.1% |
| Hot Water Extraction: Example 2 | 0.26% |

Example 3

Treatment of Neurological Condition Including but not Limited to Alzheimer's Disease Method A. Neuroprotective Composition Therapy A subject presenting with Alzheimer's disease is prescribed neuroprotective composition, and therapeutically relevant doses are administered to the subject according to a prescribed dosing regimen for a period of time. The subject's level of therapeutic response is determined periodically. If the level of therapeutic response is too low at one dose, then the dose is escalated according to a predetermined dose escalation schedule until the desired level of therapeutic response in the subject is achieved. Treatment of the subject with the neuroprotective composition is continued as needed and the dose or dosing regimen can be adjusted as needed until the patient reaches the desired clinical endpoint.

Method B. Combination Therapy: Neuroprotective Composition and Another Therapeutic Agent Method A, above, is followed except that the subject is prescribed and administered one or more other therapeutic agents for the treatment of Alzheimer's disease, or symptoms thereof. Then one or more other therapeutic agents can be administered before, after or with the neuroprotective composition. Dose escalation (or de-escalation) of the one or more other therapeutic agents can also be done. Suitable one or more other therapeutic agents include Namenda™ (memantine HCl), Aricept™ (donepezil), Razadyne™ (galantamine), Exelon™ (rivastigmine), Cognex™ (tacrine), and amantadine.

Example 4

Treatment of Neurological Condition Including but not Limited to Huntington's Disease Method A. Neuroprotective Composition Therapy A subject presenting with Huntington's disease is prescribed the neuroprotective composition, and therapeutically relevant doses are administered to the subject according to a prescribed dosing regimen for a period of time. The subject's level of therapeutic response is determined periodically. If the level of therapeutic response is too low at one dose, then the dose is escalated according to a predetermined dose escalation schedule until the desired level of therapeutic response in the subject is achieved. Treatment of the subject with neuroprotective composition is continued as needed and the dose or dosing regimen can be adjusted as needed until the patient reaches the desired clinical endpoint. The doses administered can be similar to those of Example 3 or as otherwise described herein.

Method B. Combination Therapy: Neuroprotective Composition and Another Therapeutic Agent Method A, above, is followed except that the subject is prescribed and administered one or more other therapeutic agents for the treatment of Huntington's disease, or symptoms thereof. The one or more other therapeutic agents can be administered before, after or with the neuroprotective composition. Dose escalation (or de-escalation) of the one or more other therapeutic agents can also be done. Suitable one or more other therapeutic agents include Vitamin E, Baclofen (a derivative of CoQ10), Lamotrigine (an anticonvulsant), remacemide (an anesthetic which is a low affinity NMDA antagonist), and riluzole (Na channel blocker).

Example 5

Treatment of Neurological Condition Including but not Limited to Ischemic Stroke Method A. Neuroprotective Composition Therapy A subject presenting with ischemic stroke is prescribed the neuroprotective composition, and therapeutically relevant doses are administered to the subject according to a prescribed dosing regimen for a period of time. The subject's level of therapeutic response is determined periodically. If the level of therapeutic response is too low at one dose, then the dose is escalated according to a predetermined dose escalation schedule until the desired level of therapeutic response in the subject is achieved. Treatment of the subject with the neuroprotective composition is continued as needed and the dose or dosing regimen can be adjusted as needed until the patient reaches the desired clinical endpoint. The doses administered can be similar to those in Example 3 or as otherwise described herein.

Method B. Combination Therapy: Neuroprotective Composition and Another Therapeutic Agent Method A, above, is followed except that the subject is prescribed and administered one or more other therapeutic agents for the treatment of ischemic stroke, or symptoms thereof. The one or more other therapeutic agents can be administered before, after or with the neuroprotective composition. Dose escalation (or de-escalation) of the one or more other therapeutic agents can also be done.

Example 6

HPLC Analysis of Solutions Containing Oleandrin

Samples (oleandrin standard, SCF extract and hot-water extract) were analyzed on HPLC (Waters) using the following conditions: Symmetry C18 column (5.0 µm, 150×4.6 mm I.D.; Waters); Mobile phase of MeOH:water=54:46 (v/v) and flow rate at 1.0 ml/min. Detection wavelength was set at 217 nm. The samples were prepared by dissolving the compound or extract in a fixed amount of HPLC solvent to achieve an approximate target concentration of oleandrin.

Example 7

Determination of $\alpha 3$ and $\alpha 1$ Expression in Normal Neuronal Tissue The procedures set forth in PCT International Application No. PCT/US08/82641, filed Nov. 6, 2008 in the name of Phoenix Biotechnology, Inc., the entire disclosure of which is hereby incorporated by reference, can be followed.

Example 8

Evaluation of a Neuroprotective Composition in an In Vitro Assay for Stroke and Non-Stroke Method A. Stroke: Preparation of Cortical Brain Slices and OGD.

Neocortical brain slices were prepared from PND 7 Sprague-Dawley rat pups. The cerebral cortex was dissected, cut into 400-µ-thick slices and transferred into a container containing cold artificial cerebrospinal fluid with 1

μM MK-801 before plating; MK-801 was not included in any subsequent procedures. To mimic ischemic injury using transient oxygen-glucose deprivation (OGD), slices from one hemisphere of each brain were exposed to glucose-free, $N_2$-bubbled artificial cerebrospinal fluid for 7.5 min in a low $O_2$ (0.5%) environment. The OGD slices were then plated side-by-side with control slices from the contralateral hemisphere on nitrocellulose or Millicell (Millipore) permeable membranes, which were prepared identically except for no OGD. Thirty minutes after plating, the brain slice pairs were transfected, transferred to 24-well plates, and incubated at 37° C. under 5% $CO_2$ in humidified chambers. In each experiment, 5-6 minutes of oxygen-glucose deprivation (OGD) was used to induce >50% loss of healthy cortical neurons by 24 hrs. A set concentration (3 μM) of neriifolin (a cardiac glycoside) was used as the internal positive control. For oleandrin (a cardiac glycoside), all three concentrations from 0.3 to 3 μM appeared to provide neuroprotection in the first two experiments, so the oleandrin concentrations tested were lowered in the third run and suggested that the threshold concentration for neuroprotection lies between 0.1 and 0.3 μM. A neuroprotective composition can be used as described herein for oleandrin.

Method B. Non-Stroke: Brain Slice Assay.

Neuroprotective composition, oleandrin, PBI-05204 (an unfractionated SCF extract of *Nerium oleander*) or a fraction of the extract (PBI-04711) were tested on "nonstroked" brain slices; that is, ones that were sliced and transfected with YFP but not subjected to additional trauma via OGD. See experimental procedure outlined above. We have observed that a number of neuroprotective compounds, including neriifolin, can provide modest levels of neuroprotection to such brain slices, presumably by protecting against the trauma caused by the process of slicing and culturing itself. The data demonstrate that the neuroprotective composition, oleandrin, the SCF extract appeared to be able to provide neuroprotection to such "non-OGD" brain slices to similar levels as neriifolin signifying that cardiac glycosides mediate neuroprotection even in the absence of oxygen or glucose deprivation. The neuroprotective composition also provides neuroprotection under the same conditions.

Example 9

Evaluation of Neuroprotective Compositions in an In Vitro Assay for Alzheimer's Disease In the rat brain slice model for APP/Abeta-induced degeneration of cortical pyramidal neurons biolistic transfection is used not only to introduce vital markers such as YFP, but also to introduce disease gene constructs into the same neuronal populations in the brain slices. Thus, the APP/Aβ brain slice model co-transfects YFP with APP isoforms, leading to the progressive degeneration of cortical pyramidal neurons over the course of 3-4 days after brain slice preparation and transfection. The data demonstrate that neuroprotective composition, oleandrin, PBI-05204 and PBI-04711 appeared able to provide concentration-dependent neuroprotection to APP-transfected brain slices, rescuing to levels nearly to those that can be provided by BACE inhibitor drugs.

Example 10

Evaluation of Neuroprotective Composition in an In Vitro Corticostriatal Co-Culture Assay for Huntington's Disease In this assay, instead of using intact brain slices, mutant htt is introduced via electroporation into high-density, mixed co-cultures of cortical neurons, striatal neurons, and glia arrayed in 96-well plates. The goal of this assay platform is to combine the biological/clinical relevance of a complex primary culture system that recapitulates key aspects of the interconnectivity of disease-relevant neuronal populations in vivo, with the ability to conduct large-scale fully automated screening campaigns. In this assay, over the course of 1-2 weeks in vitro, transfected mutant htt constructs induce the progressive degeneration of both striatal and cortical neurons that are subsequently quantified using automated image acquisition and object detection algorithms on the Cellomics Arrayscan VTI platform. Each data point was drawn from 6 wells with 16 images in each well automatically captured, processed, and analyzed on the Cellomics Arrayscan using protocols developed during a large-scale screening campaign being conducted in association with the Cure Huntington's Disease Initiative. In a full run, some 25,000 images are collected and analyzed in each cycle, 4 cycles per week.

Cortico-Striatal Co-Culture Assay Platform.

Pure glial cultures are prepared in advance of neuronal plating to establish 96-well plates with confluent glial beds. Cortical and striatal tissue are then dissociated separately and "nucleofected" with appropriate DNA constructs and are distinguishable later by the expression of different fluorescent proteins such as YFP, CFP, and mCherry. These separately transfected cortical and striatal neurons are then mixed thoroughly and plated into the 96-well plates containing the previously plated glial monolayers.

Neuroprotective composition, oleandrin, PBI-05204 and PBI-04711 were tested in this cortico-striatal co-culture platform and preliminarily these compounds appear to be the strongest hits we have observed to date out of >400 late-stage drug molecules that have been evaluated in this assay system. For comparison, a dose-response graph for KW6002 (an adenosine 2a receptor antagonist), the compound that we routinely include as the positive control for this co-culture assay is included. Efficacy of oleandrin is on par with KW6002, while its potency appears to be some 100-fold greater (FIGS. 3A-3D).

Example 11

Evaluation of Neuroprotective Composition in an In Vitro APP Assay for Alzheimer's Disease The composition was prepared according to Example 13. This assay was conducted similar to that of Example 9. The data in FIG. 6 demonstrate that there is a concentration dependent effect of Fraction 0-4A (0-4: mixture of OA, UA and BA) in preventing the neurodegeneration associated with introduction of the APP construct. In particular, the data demonstrate neuroprotection between the concentration range of 3 to 30 ug/ml.

Example 12

Evaluation of Neuroprotective Composition in an In Vitro tau4R Assay for Alzheimer's Disease The composition was prepared according to Example 13. The data in FIG. 7 demonstrate that there is a concentration dependent effect of Fraction 0-4A (0-4) in preventing the neurodegeneration associated with introduction of the Tau construct. In particular, the data demonstrate a neuroprotection between the concentration range of 3 to 30 ug/ml. There is a significant difference between Tau construct treated cells and those exposed to solutions of Fraction 0-4A.

Example 13

Chromatographic Fractionation of SCF Extract

A supercritical extract (5 g) of *oleander* leaves (obtained as described herein by extracting a plant mass with a mixture of supercritical $CO_2$ with EtOH added as a cosolvent/modifier, Batch #270111) was suspended in water (150 mL) and partitioned three times with hexane (150 ml each time). The water layer was subjected to ODS C-18 (octadecyl-functionalized silica gel, 20-22% labeled, 200-400 mesh) open column (400 mm (L)×38 mm (ID)) fractionation by charging the water layer directly to a bed of the ODS resin equilibrated with water. The column was treated successively with mixtures of water and methanol (1000 ml of 30% methanol in water, 1000 ml of 55% methanol in water, 1000 ml of 80% methanol in water, 1000 ml of 100% methanol) and with a mixture of acetone:methanol (2 volumes: 1 volume; 1000 ml). The effluent (1000 ML) from each mixture was collected. The solvent was removed from each fraction by evaporation to yield five fractions, namely Fr-0-1, Fr-0-2, Fr-0-3, Fr-0-4 (PBI-04711), and Fr-0-5. The fractions were then analyzed by HPLC chromatography as per Example 14.

Example 14

HPLC Analysis of Fractions of SCF Extract

The purpose of this assay was to identify extract fractions (from above) containing cardiac glycoside. A sample from each fraction obtained according to Example 13 was analyzed as follows. The fraction 1-3 mg) was dissolved in 1-5 ml of aqueous methanol (80% methanol in water). The diluted sample (10-25 µl) was analyzed with an Agilent Zorbax SB-C18 column using 80% methanol in water as the mobile phase, a flow rate of 0.7 mL/min and DAD-UV effluent monitoring at the following wavelengths: 203, 210, 217, 230, 254, 280, 310 and 300 nm.

Example 15

Figure 4A:
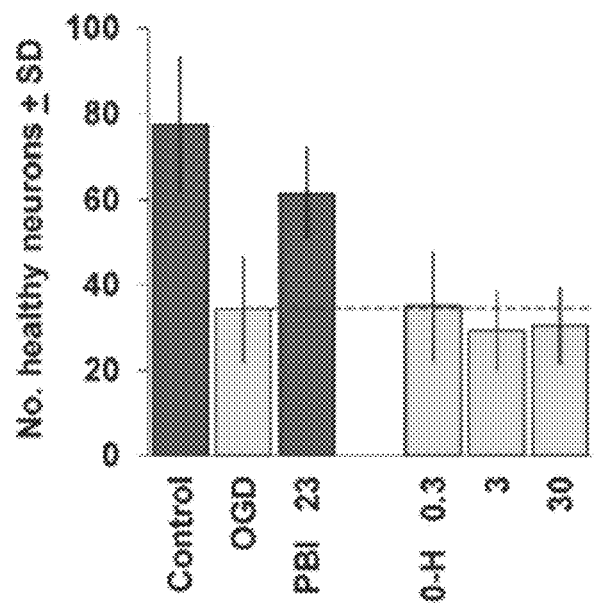
FIGS. 4A-4E depict the results of a neuroprotection brain-slice-based "stroke" assay as described herein, wherein the oleandrin-containing SCF extract has been fractionated via liquid chromatography (Example 13) and the five different fractions (described below) subjected to this assay (Examples 15 and 21): Fraction 0-H (FIG. 4A), Fraction 0-2 (FIG. 4B), Fraction 0-3 (FIG. 4C), Fraction 0-4 (also referred to as PBI-04711, FIG. 4D), Fraction 0-5 (FIG. 4E).
Figure 4B:
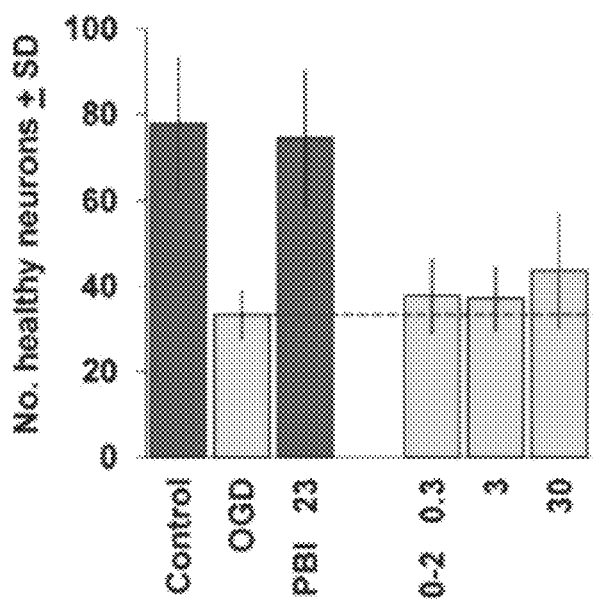
Figure 4C:
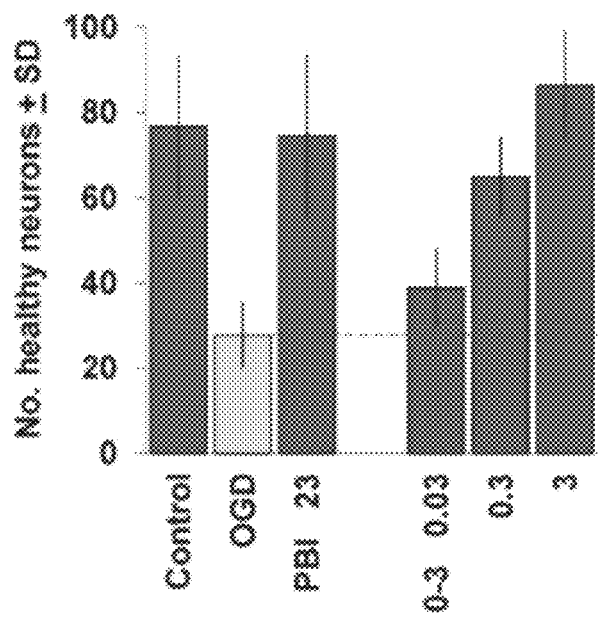
Figure 4D:
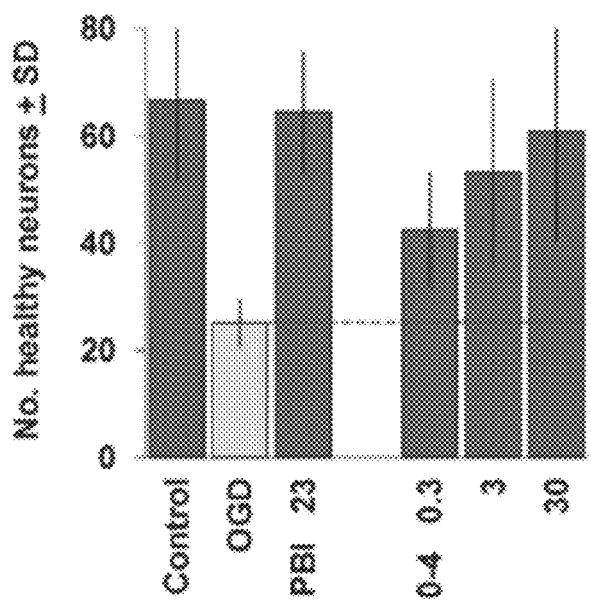
Figure 4E:
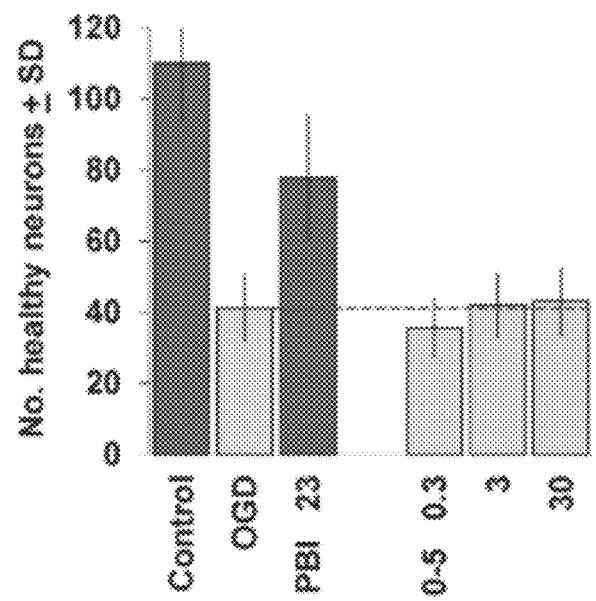

Brain-Slice Assay for Determination of Neuroprotection Provided by Fractions of Extract This assay was conducted according to Example 8. The data demonstrate that compared to untreated stroke (OGD) mediated damage to brain slice neurons PBI-05204 provides a significant level of protection. A similar level of neuroprotection was provided by Fraction 0-4A (FIGS. 4A and 5) as well as Fraction 0-3 (FIG. 4C) and Fraction 0-1 (FIG. 4D). In contrast, Fractions 0-2 (FIG. 4B) and 0-5 (FIG. 4E) demonstrated no neuroprotective effects in this OGD model of stroke mediated ischemic brain injury. A neuroprotective composition of OA, UA and BA provides neuroprotection.

Example 16

Time-Delay Brain-Slice Assay for Determination of Neuroprotection

This assay was conducted according to Example 8 except that the following changes were made. A specified length of time was allowed between OGD and introduction of the neuroprotective agent(s). The ability of PBI-05204 or PBI-04711 to provide neuroprotection to brain slices if treatment was delayed relative to the timing of the OGD treatment was determined. Data showed that a 2 hr delay of the neuroprotective composition was well tolerated, showing similar levels of neuroprotection to those attained with application of PBI-05204 immediately following OGD treatment. Neuroprotective benefit was reduced with 4 to 6 hr of delay of administration of PBI-05204, but at levels of neuroprotection that were still significantly and physiologically relevant. PBI-04711 provides neuroprotection as well.

Example 17

Identification of Compounds in a Fraction of *Nerium oleander* SCF Extract Obtained According to Example 13

The water and methanol present in the Fr-0-4 fraction were removed by evaporation under reduced pressure. The residue from the Fr-0-4 fraction of Example 13 was subjected to silica gel chromatography (below) to provide sub-fractions that were then analyzed by thin layer chromatography (TLC). Fractions having similar TLC profiles were combined and the solvents thereof removed by evaporation under reduced pressure. The remaining residues were analyzed by H'NMR.

Thin Layer Chromatography

TLC was performed on conventional analytical grade TLC plates using a mixture of hexane:ethyl acetate (7:3 v:v). The compounds were visualized with $H_2SO_4$, whereby steroids exhibit a blue color and triterpenes exhibit a purple color.

Prior to further fractionation by flash chromatography, TLC analysis of the Fr-0-4 fraction indicated the presence of one major spot and more than five small spots. The color reaction indicated that the major spot contained a mixture of steroid and triterpene and most of the small spots contained steroids. Some batches of Fr-0-4 exhibit spots for triterpenes only.

Silica Gel Flash Chromatography

Silica gel (Biotage; (10-15 g) was loaded into a column and equilibrated with a mixture of ethyl acetate (3%) and hexane (97%). The residue from the Fr-0-4 fraction was taken up in mixture 0.2-0.5 ml of ethyl acetate (3%) and hexane (97%) and charged onto the column. Flash chromatography was conducted using a solvent gradient of ethyl acetate (3%-30%) in hexane (97%-70%, respectively) followed by 100% methanol. Sub-fractions collected from the column were analyzed by TLC (above) and those fractions having similar TLC visualization profiles were combined and concentrated to remove solvent.

HNMR Spectroscopy

A sample of each of the concentrated sub-fractions obtained from flash chromatography was analyzed by HNMR using conventional methods so as to determine the structural class for the major components.

Example 18

Identification of Compounds in *Nerium oleander* SCF Extract Obtained According to Example 1 (Method B) in Unfractionated Form The SCF extract was analyzed by MS-DART TOF analysis as follows. A JEOL AccuTOF-DART mass spectrometer (Jeol U.S.A., Peobody, Mass., U.S.A.) was used.

A JEOL AccuTOF-DART mass spectrometer (Jeol USA, Peabody, Mass., USA) was used. Analyses were conducted in a positive ion mode (DART+) giving masses corresponding to the M+H+ ions generated by the DART-MS. A range of settings on the instrument was used to determine optimal conditions for *N. oleander* analyses. The general settings for DART+ included: needle voltage 3500 V; orifice 1—2-20 V; ring lens 2-5 V; orifice 2—2-5 V; and peaks voltage 1000 V. Calibrations were performed internally with each sample using a 10% solution of PEG 600 which provides mass markers throughout the required mass range of 100-1000 mass units. Other analyses were undertaken in the DART-mode and these consisted of: needle voltage 3500 V; heating element 250° C.; electrode 1—150 V; electrode 2—250 V; He gas flow rate 3.79 LPM. Mass spectrometer settings: MCP 2600 V; orifice 1—15 V; ring lens—5 V, orifice 2—5 V; and peaks voltage 1000 V. Calibrations were performed internally with each sample using a perfluorinated carboxylic acid solution that provides markers throughout the required mass range of 100-1000 mass units. The *N. oleander* samples were introduced neat into the DART helium plasma using the closed end of a borosilicate glass melting point tube. The capillary tube was held in the He plasma for approximately 3-5 s per analysis. Molecular formulas were confirmed by elemental composition and isotope matching programs provided with the JEOL AccuTOF DART-MS instrument. A searchable database of *N. oleander* constituents, developed by HerbalScience (Naples, Fla., USA) was used.

The SCF extract was found to contain at least the following components present in the indicated relative abundances (%). The relative abundance varies from batch to batch.

| Component | Relative Abundance (%) |
|---|---|
| Oleandrin | 2.99 |
| Oleandrigenin | 3.31 |
| Ursolic acid/betulinic acid | 15.29 |
| Odoroside | 0.80 |
| Oleanolic acid | 0.60 |
| Urs-12-ene-3β,28-diol/betulin | 5.44 |
| 3β,3β-hydroxy-12-olean-en-28-oic acid | 14.26 |
| 28-norurs-12-en-3β-ol | 4.94 |
| Urs-12-en-3β-ol | 4.76 |

Batch-to-batch variability in relative content of the individual components was observed. The primary pharmacologically active components of the SCF extract are oleandrin, oleanolic acid, ursolic acid and betulinic acid. The relative amounts of these four components are set forth below.

| Component | Amount (mg component per g of SCF extract) | Amount (mole of component per mole of oleandrin) |
|---|---|---|
| Oleandrin | 1-40 | 0.5-1.5 |
| Oleanolic acid | 60-80 | 4-6 |
| Ursolic acid | 60-80 | 4-6 |
| Betulinic acid | 0.1-20 | 0.1-1 |

Example 19

Fractionation of *Nerium oleander* SCF Extract (PBI-05204)

PBI-05204 was prepared as described herein or provided by Phoenix Biotechnology, Inc. (San Antonio, Tex.). Fractions thereof were prepared as follows.

The SCF extract of Example 18 was extracted with hexane. The remaining water soluble portion was further separated by reversed-phase chromatography (ODS) via sequential elution washes consisting of 30% (Fraction 0-H), 55% (Fraction 0-2), 80% (Fraction 0-3), 100% methanol (Fraction 0-4), and finally acetone-methanol (2:1 v:v; Fraction 0-5). All fractions were then subjected to analysis for relative content of oleandrin. The 100% methanol fraction was found to be free of all detectable oleandrin by HPLC analysis (Zorbax SB-18 column; Agilent). To confirm the relative abundance of its major triterpenoid components, Fraction 0-4 was separated chromatographically and quantified against triterpene standards for oleanolic acid, ursolic acid, and betulinic acid.

| Sub-fractionation of PBI-05204 | | |
|---|---|---|
| Name | Oleandrin | Other CGs |
| Fraction 0-1 | No | No |
| Fraction 0-2 | No | Yes |
| Fraction 0-3 | Yes | Yes |
| Fraction 0-4 | No | No |
| Fraction 0-5 | No | No |

Example 20

Sub-Fractionation of Fraction 0-4 (PBI-04711)

Fraction 04 (PBI-04711) was dissolved in a small quantity of methylene chloride. The insoluble part was composed mostly of triterpenoids based on the analysis of the NMR and thin-layer chromatography visualized by sulfuric acid. The insoluble part (200 mg) was then subjected to a flash silica gel chromatograph and eluted into fractions using a gradient of $CHCl_3$:MeOH (0%~8%). Fraction 42 (146 mg) was repeatedly crystallized and found to consist of pure oleanolic acid (20 mg). The supernatants of the crystallization reactions were combined. A fraction of the supernatant (16.1 mg) was further purified by preparative HPLC using a Phenomenex Luna C18(2), 5 µm, 250×21.25 mm column, eluted with a gradient of MeOH:$H_2O$ 20%~100% in 40 min, flow rate 9 mL/min to yield a mixture of oleanolic acid and ursolic acid (13.9 mg) as major components and a pure compound betulinic acid (0.3 mg) as a minor component. Another fraction of the supernatant was first separated by preparative-TLC to generate two fractions, which were further purified by preparative HPLC to yield two pure compounds uvalol (0.5 mg) and ursolic aldehyde (0.8 mg). Fraction 54 (22.6 mg) was repeatedly purified on HPLC column to obtain 3β,27-dihydroxy-12-ursen-28-oic acid (0.5 mg). Another fraction of the insoluble part (280 mg) was separated using a RediSep Rf Gold Silica Gel column (80 g). Pure ursolic acid (5.8 mg) was obtained from fraction 78 bp repeated crystallization. Fraction 105 was purified by preparative HPLC to yield a mixture of E/Z-27-(p-coumaroyl) ursolic acid (2.2 mg). Efforts to separate these two compounds were not successful because of their rapid cis-trans isomerization. Based on the isolation procedure, the content of oleanolic acid in Fraction 0-4 was estimated to be ~35%, and that for the next two most abundant triterpenoids, ursolic acid and betulinic acid, to be ~25% and ~11%, respectively. The structures of these compounds were determined by 1D and 2D NMR and comparison with data in the literature.

Example 21

Evaluation of Neuroprotective Composition in Brain Slice-Based OGD Assay

Coronal brain slices (250 µm thick) were prepared from postnatal day 10 Sprague-Dawley rat pups of either gender (Charles River) and established in organotypic culture. Animals were sacrificed in accordance with NIH guidelines and under Duke IACUC approval and oversight. Briefly, brain tissue slices were cut in ice-cold artificial cerebrospinal fluid (ACSF) and plated in interface configuration on top of culture medium (Neurobasal A medium supplemented with 15% heat-inactivated horse serum, 10 mM KCl, 10 mM HEPES, 100 U/ml penicillin/streptomycin, 1 mM sodium pyruvate, and 1 mM L-glutamine) set in 0.5% reagent-grade agarose. To model ischemic injury, brain slices were subjected to oxygen-glucose deprivation (OGD) by exposure to glucose-free, $N_2$-bubbled ACSF containing low $O_2$ (<0.5%) for 5.5 min.

One hour later, control and OGD-treated brain slices were biolistically transfected with DNAs encoding yellow fluorescent protein (YFP). For assays modeling neurodegeneration in AD or FTD, brain slices were co-transfected with YFP together with an expression construct to WT amyloid precursor protein (APP), or with YFP together with a cDNA constructed in house encoded human Tau4R0N (identical to NCBI Reference Sequence NM_016834), respectively. Brain slice explants were then incubated for 24 h under 5% $CO_2$ at 37° C. for OGD assays; or for 3 d for APP- and tau4R0N-induced neurodegeneration assays. PBI-05204, PBI-04711, triterpene mixture, and/or individual triterpene(s) were added to culture medium at the time of brain slice explantation at the indicated concentrations.

For all brain slice assays, numbers of healthy pyramidal neurons in the cortical regions of each brain slice were imaged on a Leica MZIIIFL fluorescence stereomicroscope. Cortical pyramidal neurons were readily identified by their characteristic positions and orientations in the cortical plate, and by their prominent extension of a single, apical dendrite radially towards the pial surface. Healthy cortical pyramidal neurons were deemed as those 1) presenting a stout and brightly labeled cell body located within the pyramidal neuronal layers of the cortex; 2) retaining a clear apical dendrite extending radially towards the pial surface the slice; 3) expressing ≥2 clear basal dendrites ≥2 cell body diameters long directly from the neuronal soma; and 4) showing clear and continuous cytoplasmic labeling with the YFP visual marker in the soma and throughout all neuronal processes. Statistically significant differences with respect to the negative control condition (OGD, APP-transfected, or tau4R-transfected treated with DMSO carrier only) were determined using ANOVA followed by Dunnett's post hoc comparison test at the 0.05 confidence level, with N=12 brain slices per condition. Each experiment was carried out at least 3 times.

Example 22

Evaluation of Neuroprotective Composition in Nrf2 Activation and ARE Gene Expression Nrf2 Activation Primary corticostriatal neuronal co-cultures were prepared from E18 Sprague-Dawley rat or C57Bl/6 mouse embryos of either gender. For luciferase reporter assays, the Cignal Antioxidant Response Reporter kit (Qiagen) was used. The 5×ARE luciferase reporter mixture at 40:1 luciferase:*Renilla* plasmid was transfected into cortical and striatal neurons separately using an Amaxa electroporation device (Lonza). After electroporation, neurons were pooled and immediately plated into 96-well plates containing mature glial cultures. After culturing for 96 h, neuroprotective compositions were added at the indicated concentrations for 7 or 24 h prior to harvesting using Dual-Glo Luciferase Assay System protocol and reagents (Promega). Dual-wavelength luminescence was detected using a SpectraMax L microplate reader (Molecular Devices). Luciferase values were normalized to the internal *Renilla* control and fold-expression over the DMSO-only treatment control was calculated. At least 3 independent experiments were done using 4-6 biological replicates.

ARE Gene Expression

For qPCR quantification of ARE target gene expression levels, cortical and striatal neurons were plated onto 96-well plates containing mature glial cultures and cultured for 96 h. Fraction 0-4 was added to cultures at the indicated concentrations for 6 h. At the end of the treatment period, cells were lysed and total RNA was isolated using Absolutely RNA mini-prep kits (Agilent Technologies/Stratagene). cDNA was generated using oligo dT primers and Superscript II reverse transcriptase (Invitrogen). Resulting cDNA was used for quantitative PCR of gene transcripts using SYBR Green Real-Time PCR Master Mix (Life Technologies) and the following mouse primers, for: Gclc (forward-5' TGGCCAC-TATCTGCCCAATT-3' and reverse-5'-GTCTGACACGTAGCCTCGGTAA-3'), Nqo1 (forward-5'-GCCCGCATGCAGATCCT-3' and reverse 5'-GGTCTCCTCCCAGACGGTTT3'), Srx (forward-5'-GCTTCCTCTCGGGAGTCCTT-3' and reverse-5'-CAGCAACAGCGACTACGAAGTAA-3'), and Hmox1 (forward-5'-CCTCACTGGCAGGAAATCATC-3' and reverse-5'-CCTCGTGGAGACGCTTTACATA-3') (Integrated DNA Technologies). For rat corticostriatal co-culture samples, qPCR primers used were as previously described (van Roon-Mom, W. M. et al. Mutant huntingtin activates Nrf2-responsive genes and impairs dopamine synthesis in a PC12 model of Huntington's disease. *BMC Molecular Biology* (2008), 9, 1-13, doi:10.1186/1471-2199-9-84). Each biological sample was measured in triplicate on a ViiA 7 real-time PCR instrument (Applied Biosystems); fold expression was calculated after normalization to corresponding control GAPDH levels.

Example 23

HPLC Analysis of Triterpene Components

Figure 21:
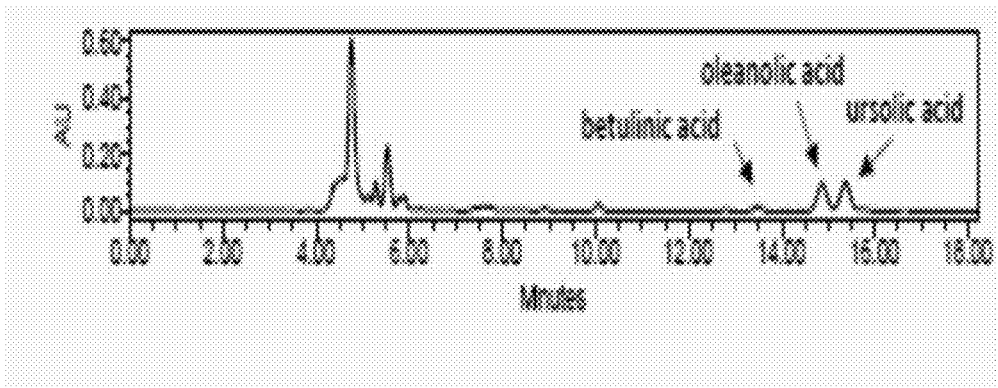
FIG. 21 depicts an HPLC chromatogram for the SCF extract (PBI-05204). HPLC analysis was conducted according to Example 23. The triterpenes OA, UA and BA are eluted after other components, e.g. oleandrin, of the SCF extract.

PBI-05204 and PBI-04711 were prepared as described herein. PBI-05204 (the SCF extract) was prepared as described herein. The triterpene components thereof were quantified by HPLC using a Gemini C18 diphenyl column and eluting the triterpenes with an isocratic mobile phase consisting of 95% MeCN with 0.1% formic acid at a flow rate of 0.6 ml/min and a detection wavelength of 220 nm. Standard curves were developed and used to calculate the relative molar ratios of oleanolic acid, ursolic acid and betulinic acid compounds in the neuroprotective compositions of the invention. FIG. 8 depicts the HPLC chromatogram of PBI-05204. FIG. 16 depicts the HPLC chromatogram for PBI-04711, and FIG. 21 depicts the HPLC chromatogram of PBI-05204

Example 24

Preparation of Neuroprotective Compositions

Synthetic neuroprotective compositions can be prepared by mixing the individual components thereof to form a mixture.
Neuroprotective Composition with Oleandrin and Triterpenes Known amounts of oleandrin, oleanolic acid, ursolic acid and optionally betulinic acid were mixed according to a predetermined molar ratio of the components as defined herein. The components were mixed in solid form or were mixed in one or more solvent(s), e.g. methanol, ethanol, chloroform, acetone, propanol, dimethyl sulfoxide (DMSO), dimethylformamide (DMF), dimethylacetamide (DMAC), N-methylpyrrolidone (NMP) or mixtures thereof. The resultant mixture contained the components in the relative molar ratios as described herein.

For a pharmaceutically acceptable neuroprotective composition, at least one pharmaceutically acceptable excipient was mixed in with the pharmacologically active agents. A neuroprotective composition is formulated for administration to a mammal.

Synthetic neuroprotective compositions containing oleandrin, oleanolic acid, ursolic acid and betulinic acid, according to the molar ratios described herein, were prepared.
Neuroprotective Composition with Triterpenes and Excluding Cardiac Glycoside (Oleandrin)

Known amounts of oleanolic acid, ursolic acid and optionally betulinic acid were mixed according to a predetermined molar ratio of the components as defined herein. The components were mixed in solid form or were mixed in solvent(s), e.g. methanol, ethanol, chloroform, acetone, propanol, dimethyl sulfoxide (DMSO), dimethylformamide (DMF), dimethylacetamide (DMAC), N-methylpyrrolidone (NMP) or mixtures thereof. The resultant mixture contained the components in the relative molar ratios as described herein.

For a pharmaceutically acceptable neuroprotective composition, at least one pharmaceutically acceptable excipient was mixed in with the pharmacologically active agents. A neuroprotective composition is formulated for administration to a mammal.

The following synthetic neuroprotective compositions containing the specified combination of triterpenes according to the molar ratios described herein were prepared: a) oleanolic acid, ursolic acid and betulinic acid; b) oleanolic acid and ursolic acid; c) oleanolic acid and betulinic acid.

Example 25

Treatment of Neurological Condition Including but not Limited to Alzheimer's Disease Method A. Neuroprotective Composition Therapy A subject presenting with Alzheimer's disease is prescribed neuroprotective composition, and therapeutically relevant doses are administered to the subject according to a prescribed dosing regimen for a period of time. The subject's level of therapeutic response is determined periodically. If the level of therapeutic response is too low at one dose, then the dose is escalated according to a predetermined dose escalation schedule until the desired level of therapeutic response in the subject is achieved. Treatment of the subject with the neuroprotective composition is continued as needed and the dose or dosing regimen can be adjusted as needed until the patient reaches the desired clinical endpoint.

Method B. Combination Therapy: Neuroprotective Composition and Another Therapeutic Agent Method A, above, is followed except that the subject is prescribed and administered one or more other therapeutic agents for the treatment of Alzheimer's disease, or symptoms thereof. Then one or more other therapeutic agents can be administered before, after or with the extract. Dose escalation (or de-escalation) of the one or more other therapeutic agents can also be done. Suitable one or more other therapeutic agents include Namenda™ (memantine HCl), Aricept™ (donepezil), Razadyne™ (galantamine), Exelon™ (rivastigmine), Cognex™ (tacrine), and amantadine.

Example 26

Treatment of Neurological Condition Including but not Limited to Huntington's Disease Method A. Neuroprotective Composition Therapy A subject presenting with Huntington's disease is prescribed the neuroprotective composition, and therapeutically relevant doses are administered to the subject according to a prescribed dosing regimen for a period of time. The subject's level of therapeutic response is determined periodically. If the level of therapeutic response is too low at one dose, then the dose is escalated according to a predetermined dose escalation schedule until the desired level of therapeutic response in the subject is achieved. Treatment of the subject with neuroprotective composition is continued as needed and the dose or dosing regimen can be adjusted as needed until the patient reaches the desired clinical endpoint. The doses administered can be similar to those described herein.

Method B. Combination Therapy: Neuroprotective Composition and Another Therapeutic Agent Method A, above, is followed except that the subject is prescribed and administered one or more other therapeutic agents for the treatment of Huntington's disease, or symptoms thereof. The one or more other therapeutic agents can be administered before, after or with the neuroprotective composition. Dose escalation (or de-escalation) of the one or more other therapeutic agents can also be done. Suitable one or more other therapeutic agents include Vitamin E, Baclofen (a derivative of CoQ10), Lamotrigine (an anticonvulsant), remacemide (an anesthetic which is a low affinity NMDA antagonist), and riluzole (Na channel blocker).

Example 27

Treatment of Neurological Condition Including but not Limited to Ischemic Stroke Method A. Neuroprotective Composition Therapy A subject presenting with ischemic stroke is prescribed the neuroprotective composition, and therapeutically relevant doses are administered to the subject according to a prescribed dosing regimen for a period of time. The subject's level of therapeutic response is determined periodically. If the level of therapeutic response is too low at one dose, then the dose is escalated according to a predetermined dose escalation schedule until the desired level of therapeutic response in the subject is achieved. Treatment of the subject with the neuroprotective composition is continued as needed and the dose or dosing regimen can be adjusted as needed until the patient reaches the desired clinical endpoint. The doses administered can be similar to those described herein.

Method B. Combination Therapy: Neuroprotective Composition and Another Therapeutic Agent Method A, above, is followed except that the subject is prescribed and administered one or more other therapeutic agents for the treatment of ischemic stroke, or symptoms thereof. The one or more other therapeutic agents can be administered before, after or with the neuroprotective composition. Dose escalation (or de-escalation) of the one or more other therapeutic agents can also be done.

Example 28

Treatment of Neurological Condition Including but not Limited to Parkinson's Disease Method A. Neuroprotective Composition Therapy A subject presenting with Parkinson's disease is prescribed the neuroprotective composition, and therapeutically relevant doses are administered to the subject according to a prescribed dosing regimen for a period of time. The subject's level of therapeutic response is determined periodically. If the level of therapeutic response is too low at one dose, then the dose is escalated according to a predetermined dose escalation schedule until the desired level of therapeutic response in the subject is achieved. Treatment of the subject with neuroprotective composition is continued as needed and the dose or dosing regimen can be adjusted as needed until the patient reaches the desired clinical endpoint. The doses administered can be similar to those described herein.

Method B. Combination Therapy: Neuroprotective Composition and Another Therapeutic Agent Method A, above, is followed except that the subject is prescribed and administered one or more other therapeutic agents for the treatment of Parkinson's disease, or symptoms thereof. The one or more other therapeutic agents can be administered before, after or with the neuroprotective composition. Dose escalation (or de-escalation) of the one or more other therapeutic agents can also be done. Suitable one or more other therapeutic agents include a combination of carbidopa and levodopa, rasagiline, pramipexole, ropinrole, amantadine, memantine, entacapone, rotigotine, benztropine, selegiline, biperiden, a combination of carbidopa and levodopa and entacapone, trihexylphenidyl, rivastigmine, apomorphine, levodopa, carbidopa, bromocriptine, belladonna, tolcapone, or a combination thereof.

As used herein and unless otherwise specified, the term "about" or "approximately" are taken to mean±10%, ±5%, ±2.5% or ±1% of a specified valued. As used herein and unless otherwise specified, the term "substantially" is taken to mean "to a large degree", "at least a majority of", greater than 70%, greater than 85%, greater than 90%, greater than 95%, greater than 98% or greater than 99%.

When a range is specified herein, the range includes all numbers therein.

As used herein, the term "and/or", when included in a list is taken to mean the invention includes embodiments including each of the listed items individually or in any combination of any two or more of the listed items.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

The invention claimed is:

1. A neuroprotective pharmaceutical composition consisting essentially of oleanolic acid (O), ursolic acid (U) and betulinic acid (B) as the primary or sole pharmacologically active ingredients, wherein:
    a) the neuroprotective composition excludes cardiac glycoside, and excludes pharmacologically active polysaccharide obtained from *Nerium* species or of *Thevetia* species;
    b) the O, U and B are independently selected upon each occurrence from the free acid form, salt form, derivative form, prodrug form or a combination thereof; and
    c) the molar ratio of the O:U:B is about 4-2 O:3-1 U:0.1-1.5 B.

2. The composition of claim 1, wherein the molar amount of O exceeds the molar amount of U.

3. The composition of claim 2, wherein the molar amount of U exceeds the molar amount of B.

4. The composition of claim 1, wherein the molar ratio of O:U is about 3.2 O:about 2.3 U, about 4-2 O:0.1-1.5 U, 3-3.5 O:about 0.8-1.2 U, about 3 O 1 U, or about 3.2 O:about 1 U.

5. The composition of claim 1, wherein the molar ratio of O:B is 3-3.5 O:about 0.8-1.2 B, or about 3:O 1 B, or about 3.2 O:about 1 B.

6. The composition of claim 1, wherein the molar ratio of O:U:B is about 3-3.5 O:about 2-2.5 U:about 0.8-1.2 B, about 3 O: 2 U:1 B, or about 3.2 O:about 2.3 U:about 1 B.

7. A pharmaceutical dosage form comprising at least one pharmaceutical excipient and said neuroprotective composition of claim 1.

8. The dosage form of claim 7 comprising 0.1-100 micrograms or 0.1 to 500 mg of said neuroprotective composition.

9. The dosage form of claim 7, wherein said at least one pharmaceutical excipient is independently selected upon each occurrence from the group consisting of surfactant, solubilizer, solvent, liquid carrier, chelating agent, preservative, antioxidant, adsorbent, acidifying agent, alkalizing agent, antifoaming agent, buffering agent, colorant, electrolyte, salt, stabilizer, tonicity modifier, diluent, filler, and a combination thereof.

10. The dosage form of claim 7, wherein said dosage form is a parenteral, otic, ophthalmic, nasal, inhalable, buccal, sublingual, enteral, topical, oral, peroral, intravenously administrable, intramuscularly administrable, intraperitoneally administrable, or injectable dosage form.

11. The dosage form of claim 7, wherein said dosage form is a tablet, capsule, pill, caplet, troche, sache, solution, suspension, dispersion, vial, bag, bottle, or injectable liquid.

12. A neuroprotective composition consisting essentially of oleanolic acid (O), ursolic acid (U), betulinic acid (B), and one or more other therapeutic agents, wherein:
    a) the neuroprotective composition excludes cardiac glycoside, and excludes pharmacologically active polysaccharide obtained from *Nerium* species or of *Thevetia* species;
    b) the O, U and B are independently selected upon each occurrence from the free acid form, salt form, derivative form, prodrug form or a combination thereof; and
    c) the molar ratio of the O:U:B is about 4-2 O:3-1 U:0.1-1.5 B.

13. The composition of claim 12, wherein the molar amount of O exceeds the molar amount of U.

14. The composition of claim 13, wherein the molar amount of U exceeds the molar amount of B.

15. The composition of claim 12, wherein the molar ratio of O:U is about 3-3.5 O:about 2-2.5 U, about 3 O:about 2 U, about 3.2 O:about 2.3 U, about 3 O: 1 U, or aobut 3.2 O about 1 U.

16. The composition of claim 12, wherein the molar ratio of O:B is 3-3.5 O:about 0.8-1.2 B, about 3 O: 1 B, or about 3.2 O:about 1 B.

17. The composition of claim 12, wherein the molar ratio of O:U:B is about 3-3.5 O:about 2-2.5 U:about 0.8-1.2 B, about 3 O: 2 U:1 B, or about 3.2 O:about 2.3 U:about 1 B.

18. The composition of claim 12, wherein said one or more other therapeutic agents is selected from the group consisting of BACE inhibitor, acetylcholinesterase inhibitor, memantine HCl, donepezil, galantamine, rivastigmine, tacrine, NMDA (n-methyl d-aspartate) receptor antagonist, sodium channel blockers, Vitamin E, baclofen, a derivative of CoQ10, lamotrigine, anticonvulsant, remacemide, anesthetic, a low affinity NMDA antagonist, riluzole, Na channel blocker, alteplase, thrombolytic agent, combination of carbidopa and levodopa, rasagiline, pramipexole, ropinrole, amantadine, memantine, entacapone, rotigotine, benztropine, selegiline, biperiden, a combination of carbidopa and levodopa and entacapone, trihexylphenidyl, rivastigmine, apomorphine, levodopa, carbidopa, bromocriptine, *belladonna*, and tolcapone.

19. A pharmaceutical dosage form comprising at least one pharmaceutical excipient and said neuroprotective composition of claim 12.

20. The dosage form of claim 19 comprising 0.1-100 micrograms or 0.1 to 500 mg of said neuroprotective composition.

21. The dosage form of claim 19, wherein said at least one pharmaceutical excipient is independently selected upon each occurrence from the group consisting of surfactant, solubilizer, solvent, liquid carrier, chelating agent, preservative, antioxidant, adsorbent, acidifying agent, alkalizing agent, antifoaming agent, buffering agent, colorant, electrolyte, salt, stabilizer, tonicity modifier, diluent, filler, and a combination thereof.

22. The dosage form of claim 19, wherein said dosage form is a parenteral, otic, ophthalmic, nasal, inhalable, buccal, sublingual, enteral, topical, oral, peroral, intravenously administrable, intramuscularly administrable, intraperitoneally administrable, or injectable dosage form.

23. The dosage form of claim 19, wherein said dosage form is a tablet, capsule, pill, caplet, troche, sache, solution, suspension, dispersion, vial, bag, bottle, or injectable liquid.

* * * * *